(12) United States Patent
Brenner et al.

(10) Patent No.: US 9,644,215 B2
(45) Date of Patent: May 9, 2017

(54) AAV1-CASPASE GENE THERAPY INDUCED PYROPTOSIS FOR THE TREATMENT OF TUMORS

(71) Applicant: THE GENERAL HOSPITAL CORPORATION, Boston, MA (US)

(72) Inventors: Gary J. Brenner, Winchester, MA (US); Xandra O. Breakefield, Newton, MA (US); Giulia Fulci, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 178 days.

(21) Appl. No.: 14/169,112

(22) Filed: Jan. 30, 2014

(65) Prior Publication Data

US 2014/0309288 A1 Oct. 16, 2014

Related U.S. Application Data

(60) Provisional application No. 61/811,200, filed on Apr. 12, 2013.

(51) Int. Cl.
*C12N 15/00* (2006.01)
*A61K 48/00* (2006.01)
*C12N 15/86* (2006.01)
*C12N 9/16* (2006.01)

(52) U.S. Cl.
CPC ............ *C12N 15/86* (2013.01); *A61K 48/005* (2013.01); *C12N 9/16* (2013.01); *C12N 2750/14143* (2013.01); *C12N 2830/008* (2013.01); *C12Y 304/22036* (2013.01)

(58) Field of Classification Search
CPC ......... C12N 2750/00033; C12N 2750/114011; C12N 2750/14311; C12N 15/86; C12N 2740/15043; C12N 5/0622; C12N 2740/15045; C12N 2506/08; C12N 2750/14143; C12N 2830/008; C12N 15/85; C12N 9/16; C12N 2740/16043; C12N 2830/85; C12N 2840/007; C12N 2710/10043; C12N 2710/10332; C12N 2710/10343; A61K 48/00; A61K 2121/00; A61K 38/1709; A61K 38/1761; A61K 35/30; A61K 38/18; A61K 48/0058; A61K 48/0075; A61K 9/0019; A61K 2039/572; A61K 35/76; A61K 38/17; A61K 48/005
See application file for complete search history.

(56) References Cited

U.S. PATENT DOCUMENTS 5,139,941 A 8/1992 Muzyczka et al.
5,173,414 A 12/1992 Lebkowski et al.
5,399,346 A 3/1995 Anderson et al.
2010/0129357 A1 5/2010 Garcia-Martinez et al.
2011/0033419 A1 2/2011 Aurellan et al.

FOREIGN PATENT DOCUMENTS

WO 92/01070 A1 1/1992
WO 93/03769 A1 3/1993
WO 2007/124573 A1 11/2007
WO 2013/138463 A1 9/2013

OTHER PUBLICATIONS

Prabhakar et al. Imaging and therapy of experimental schwannomas using HSV amplicon vector-encoding apoptotic protein under Schwann cell promoter. Cancer Gene Therapy, 2010, vol. 17, pp. 266-274.*
Homs et al. Schwann cell targeting via intrasciatic injection of AAV8 as gene therapy strategy for peripheral nerve regeneration. Gene Therapy, 2011, vol. 18, pp. 622-630.*
McCarty, Self-complementary AAV Vectors; Advances and Applications. Molecular Therapy, 2008, vol. 10, pp. 1648-1656.*
Sarkar et al., "Monocyte derived microvesicles deliver a cell death message via encapsulated caspase-1", PLoS One, 4: e7140 (2009).
Saydam et al., "A novel imaging-compatible sciatic nerve schwannoma model", J. Neurosci. Methods, 195: 75-77 (2011).
Shen et al., "Age-related changes in myelin morphology, electrophysiological property and myelin-associated protein expression of mouse sciatic nerves", Neurosci. Lett., 502: 162-167 (2011).
Tamai et al., "AAV-8 vector expressing IL-24 efficiently suppresses tumor growth mediated by specific mechanisms in MLL/AF4-positive ALL model mice", Blood 119: 64-71 (2012).
Taylor et al., "MicroRNA signatures of tumor-derived exosomes as diagnostic biomarkers of ovarian cancer", Gynecol. Oncol., 110:13-21 (2008).
Teschendorf et al., "Efficacy of recombinant adeno-associated viral vectors serotypes 1, 2, and 5 for the transduction of pancreatic and colon carcinoma cells", Anticancer Res., 30:1931-1935 (2010).
Vincent et al., "Replication and packaging of HIV envelope genes in a novel adeno-associated virus vector system" Vaccines 90: 353-359 (1990).
Worgall et al., "Treatment of late infantile neuronal ceroid lipofuscinosis by CNS administration of a serotype 2 adeno-associated virus expressing CLN2 cDNA", Hum. Gene Ther., 19: 463-474 (2008).
Agarwal et al., "Cannbinoids mediate analgesia largely via peripheral type 1 cannabinoid receptors in nociceptors", Nat Neurosci, 10(7): 870-879 (2007).

(Continued)

*Primary Examiner* — Marcia S Noble
(74) *Attorney, Agent, or Firm* — Nixon Peabody LLP

(57) ABSTRACT

Described herein are compositions and methods for treating, inhibiting, preventing, reducing the severity of and/or reducing the progression of schwannoma, as well as any disease or physiological disease-state in which schwannoma plays a role. The compositions comprise an rAAV vector that includes a caspase-1 gene or a variant thereof and a Schwann cell specific promoter.

20 Claims, 16 Drawing Sheets

(56) References Cited

OTHER PUBLICATIONS

Antinheimo et al., "Population-based analysis of sporadic and type 2 neurofibromatosis-associated meningiomas and schwannomas." Neurology 54: 71-76 (2000).
Balaj et al., "Tumour microvesicles contain retrotransposon elements and amplified oncogene sequences." Nat Commun. 2: 180 (2011).
Baser et al., "Increasing the specificity of diagnostic criteria for schwannomatosis." Neurology 66: 730-732 (2006).
Bowers et al., "Genetic therapy for the nervous system." Hum. Mol. Genet. 20: R28-R41 (2011).
Broekman et al., "Adeno-associated virus vectors serotyped with AAV8 capsid are more efficient than AAV-1 or -2 serotypes for widespread gene delivery to the neonatal mouse brain", Neuroscience, 138: 501-510 (2006).
Brown et al., "Multiple regulatory elements control transcription of the peripheral myelin protein zero gene", J. Biol. Chem., 272: 28939-28947 (1997).
Carter, "Adeno-associated virus vectors", Current Opinion in Biotechnology, 3: 533-539 (1992).
Chen et al., "Loss of modifier of cell adhesion reveals a pathway leading to axonal degeneration", J. Neurosci., 29: 118-130 (2009).
Chiorini et al., "Cloning of adeno-associated virus type 4 (AAV4) and generation of recombinant AAV4 particles," J. Virol., vol. 71: 6823-6833 (1997).
Colunga et al., "The HSV-2 mutant PK induces melanoma oncolysis vis non-redundant death programs and associated with autophagy and pyroptosis protein", Gene Ther., 17(3): 315-327 (2010).
Di Stasi et al., "Inducible apoptosis as a safety switch for adoptive cell therapy", N. Engl. J. Med., 365: 1673-1683 (2011).
Eberling et al., "Results from a phase I safety trial of hAADC gene therapy for Parkinson disease", Neurology ,70: 1980-1983 (2008).
Friedlander, "Role of caspase 1 in neurologic disease", Arch. Neurol., 57: 1273-1276 (2000).
Furlan et al., "Caspase-1 regulates the inflammatory process leading to autoimmune de-myelination." J. Immunol. 163, 2403-2409. (1999).
Gao et al., "Novel adeno-associated viruses from rhesus monkeys as vectors for human gene therapy", Proc Natl Acad Sci USA, 99: 11854-11859 (2002).
Gao et al., "Clades of Adeno-associated viruses are widely disseminated in human tissues", J. Virol., 78(12): 6381-6388 (2004).
Gray et al., "Optimizing promoters for recombinant adeno-associated virus-mediated gene expression in the peripheral and central nervous system using self-complementary vectors", Hum. Gene Ther., 22: 1143-1153 (2011).
Hadfield et al., "Molecular characterisation of SMARCB1 and NF2 in familial and sporadic schwannomatosis", J. Med. Genet., 45: 332-339 (2008).
Hauck et al., "Characterization of tissue tropism determinants of adeno-associated virus type 1", Journal of Virology 77(4): 2768-2774 (2003).
Huang et al., "Management of patients with schwannomatosis: Report of six cases and review of the literature", Surg. Neurol., 62: 353-361 (2004).
Hulsebos et al., "Germline mutation of INI1/SMARCB1 in familial schwanno-matosis", Am. J. Hum. Genet., 80: 805-810 (2007).
Hung et al., "Establishment and characterization of a schwannoma cell line from a patient with neurofibromatosis 2", Int. J. Oncol., 20: 475-482 (2002).
Jacoby et al., "Molecular analysis of the NF2 tumor-suppressor gene in schwannomatosis", Am. J. Hum. Genet. 61: 1293-1302 (1997).
Jessen et al., "The origin and development of glial cells in peripheral nerves", Nat. Rev. Neurosci., 6: 671-682 (2005).
Juan et al., "Molecular characterization of mouse and rat CPP32 f3 gene encoding a cysteine protease resembling interleukin-1 f 3 converting enzyme and CED-3", Oncogene, 13: 749-755 (1996).
Kaplitt et al., "Safety and tolerability of gene therapy with an adeno-associated virus (AAV) borne GAD gene for Parkinson's disease: An open label, phase I trial", Lancet, 369: 2097-2105 (2007).
Kirschbaum et al., "Rotarod impairment: Catalepsy-like screening test for antipsychotic side effects", Int. J. Neurosci., 119: 1509-1522 (2009).
Kotin, "Prospects for the use of adeno-associated virus as a vector for human gene therapy", Human Gene Therapy, 5: 793-801 (1994).
Lamkanfi et al., "Inflammasomes: Guardians of cytosolic sanctity", Immunol. Rev., 227: 95-105 (2009).
Lebkowski et al., "Adeno-associated virus: a vector system for efficient introduction and integration of DNA into a variety of mammalian cell types", Molec. Cell. Biol., 8(10): 3988-3996 (1988).
Lee et al., "P0 is constitutively expressed in the rat neural crest and embryonic nerves and is negatively and positively regulated by axons to generate non-myelin-forming and myelin-forming Schwann cells, respectively", Mol. Cell. Neurosci., 8: 336-350 (1997).
Lentz et al., "Viral vectors for gene delivery to the central nervous system", Neurobiol. Dis., 48: 179-188 (2012).
Lu-Emerson et al., "The neurofibromatosis. 2. NF2 and schwannomatosis", Rev. Neurol. Dis., 6: E81-E86 (2009).
Maitituoheti et al., "Adeno-associated virus-mediated local delivery of LIGHT suppresses tumori-genesis in a murine cervical cancer model", J. Immunother., 34: 581-587 (2011).
McCarty et al., "Adeno-associated virus terminal repeat (TR) mutant generates self-complementary vectors to overcome the rate-limiting step to transduction in vivo", Gene Ther., 10: 2112-2118 (2003).
McClatchey et al., "Membrane organization and tumorigenesis—the NF2 tumor suppressor, Merlin", Genes Dev., 19: 2265-2277 (2005).
McCown, "Adeno-associated virus (AAV) vectors in the CNS", Curr. Gene Ther., 11: 181-188 (2011).
McPhee et al., "Immune responses to AAV in a phase I study for Canavan disease", J. Gene Med., 8: 577-588 (2006).
Meijer et al., "Controlling brain tumor growth by intraventricular administration of an AAV vector encoding IFN-f3", Cancer Gene Ther., 16: 664-671 (2009).
Miao et al., "Caspase-1-induced pyroptotic cell death", Immunol. Rev., 243: 206-214 (2011).
Muramatsu et al., "Nucleotide sequenci).ng and generation of an infectious clone of adeno-associated virus 3", Virology, 221: 208-217 (1996).
Murphy et al., "Classification and nomenclature of viruses: sixth report of the International Committee on Taxonomy of Viruses", Arch. Virol., 1995: 169-175 (1995).
Muzyczka, "Use of adeno-associated virus as a general transduction vector for mammalian cells," Curr Top Microbiol Immunol, 158: 97-129 (1992).
Parks et al., "Seroepidemiological and ecological studies of the adenovirus-associated satellite viruses", J. Virol., 2: 716-722 (1970).
Prabhakar et al., "Treatment of implantable NF2 schwannoma tumor models with oncolytic herpes simplex virus G47D." Cancer Gene Ther., 14: 460-467 (2007).
Prabhakar et al., "Regression of Schwannoman Induced by Adeno-Associated Virus-Mediated delivery of Caspase-1", Human Gene Therapy, 24:1-11 (2013).
Rutledge et al., "Infectious clones and vectors derived from adeno-associated virus (AAV) serotypes other than AAV type 2," J. Virol., 72: 309-319 (1998).
Samulski et al., "Cloning of adeno-associated virus into pBR322: rescue of intact virus from the recombinant plasmid in human cells," Proc. Natl. Acad. Sci. USA, 79: 2077-2081 (1982).
Samulski, "Adeno-associated virus: integration at a specific chromosomal locus," Curr. Opin. Genet. Dev., 3: 74-80 (1993).
Li et al., "Adeno-Associated Virus Vectors: Potential Applications for Cancer Gene Therapy", Cancer Gene Ther. 12(12): 913-925 (2005).
Rouleau et al., "Alteration in a new gene encoding a putative membrane-organizing protein causes neuro-fibromatosis type 2", Nature 363: 515-521 (1993).
Tanaka et al., "Therapeutic Potential of HSP90 Inhibition for Neurofibromatosis Type 2", Clinical Cancer Research, 19(14): 3856-3870 (2013).

* cited by examiner

B

C

A  1 day post-implantation

B  1 week post-implantation

AAV1-CASPASE GENE THERAPY INDUCED PYROPTOSIS FOR THE TREATMENT OF TUMORS

CROSS-REFERENCE TO RELATED APPLICATION

This application claims the benefit under 35 U.S.C. §119 (e) of U.S. Provisional Patent Application No. 61/811,200 filed on Apr. 12, 2013, which is incorporated herein by reference in its entirety.

STATEMENT REGARDING FEDERALLY-SPONSORED RESEARCH

This invention was made with government support under Grant Nos. NS081146 and NS24279 awarded by the National Institutes of Health and Grant No. NF060106 awarded by the Department of Defense. The government has certain rights in the invention.

SEQUENCE LISTING

The instant application contains a Sequence Listing which has been submitted in ASCII format via EFS-Web and is hereby incorporated by reference in its entirety. Said ASCII copy, created on Jan. 30, 2014, is named 030258-077722-US_SL.txt and is 38,977 bytes in size.

TECHNICAL FIELD

The invention relates to gene therapies and tumor treatments.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Gene delivery is a promising method for the treatment of acquired and inherited diseases. A number of viral-based systems for gene transfer purposes have been described, such as retroviral systems, which are currently the most widely used viral vector systems for gene transfer. For descriptions of various retroviral systems, see, e.g., U.S. Pat. No. 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109. However, the recent description of retrovirus vector-associated leukemogenesis in two patients has underscored potential limitations of this vector system.

A number of adenovirus-based gene delivery systems have also been developed. Human adenoviruses are double-stranded DNA viruses which enter cells by receptor-mediated endocytosis. These viruses are particularly well suited for gene transfer because they are easy to grow and manipulate and they exhibit a broad host range both in vivo and in vitro. Adenovirus is easily produced at high titers and is stable so that it can be purified and stored. For descriptions of various adenovirus-based gene delivery systems, see, e.g., Haj-Ahmad and Graham (1986) J. Virol. 57:267-274; Bett et al. (1993) J. Virol. 67:5911-5921; Mittereder et al. (1994) Human Gene Therapy 5:717-729; Seth et al. (1994) J. Virol. 68:933-940; Barr et al. (1994) Gene Therapy 1:51-58; Berkner, K. L. (1988) BioTechniques 6:616-629; and Rich et al. (1993) Human Gene Therapy 4:461-476. However adenovirus virus vectors, including the newer helper-dependant adenovirus vectors are associated with triggering host innate immunity that can be highly toxic.

Eukaryotic vectors based upon the nonpathogenic parvovirus, adeno-associated virus ("AAV"), have recently emerged as promising vehicles for efficient gene transfer (Muzyczka, N., "Use of adeno-associated virus as a general transduction vector for mammalian cells," Curr Top Microbiol Immunol, Vol. 158, pp. 97-129 (1992)). AAV is a replication-defective DNA virus with a 4.7 kb genome with palindromic inverted terminal repeats ("ITR"). Coinfection with a helper virus, typically adenovirus or herpes simplex virus, is required for productive infection. In the absence of helper virus coinfection, AAV stably integrates via the ITRs into chromosomal DNA, or may persist in an episomal state. Wild type AAV is unique in the capacity for integration into a specific region of human DNA termed "AAVS1" on human chromosome 19.

AAV have been found in many animal species, including nonhuman primates, canines, fowl, and humans (Murphy, F. A. et al., "Classification and nomenclature of viruses: sixth report of the International Committee on Taxonomy of Viruses," Arch. Virol., Vol. 1995, pp. 169-175 (1995)). There are more than 100 serotypes of AAV, including AAV type 1 (AAV-1), isolated from primates, AAV-2, AAV-3, and AAV-5, isolated from humans, and AAV-6, isolated from a human adenovirus preparation; other serotypes are being intensively evaluated for use in gene therapy. See, e.g. Gao, P. (2004) J Virol. 78(12):6381-6388. AAV-2 is the most characterized primate serotype, since its infectious clone was the first one made (Samulski, R. J. et al., "Cloning of adeno-associated virus into pBR322: rescue of intact virus from the recombinant plasmid in human cells," Proc. Natl. Acad. Sci. USA, Vol. 79, pp. 2077-2081 (1982)). The full sequences for AAV-3A, AAV-3B, AAV-4, and AAV-6 recently were determined (Chiorini, J. A. et al., "Cloning of adeno-associated virus type 4 (AAV4) and generation of recombinant AAV4 particles," J. Virol., Vol. 71, pp. 6823-6833 (1997); Muramatsu, S. et al., "Nucleotide sequencing and generation of an infectious clone of adeno-associated virus 3," Virology, Vol. 221, pp. 208-217 (1996); and Rutledge, E. A. et al., "Infectious clones and vectors derived from adeno-associated virus (AAV) serotypes other than AAV type 2," J. Virol., Vol. 72, pp. 309-319 (1998)). Generally, all primate AAV show more than 80% homology in nucleotide sequence. AAV vectors have been based primarily on serotype 2, a human-derived parvovirus (Parks, W. P. et al., "Seroepidemiological and ecological studies of the adenovirus-associated satellite viruses," J. Virol., Vol. 2, pp. 716-722 (1970); and Samulski, R. J., "Adeno-associated virus: integration at a specific chromosomal locus," Curr. Opin. Genet. Dev., Vol. 3, pp. 74-80 (1993)).

The early availability of an infectious clone of AAV-2 stimulated work on the development of replication-defective vectors. The AAV2 genome has two major open reading frames ("ORFs"); the left encodes functions necessary for AAV ori mediated replication and site specific integration (Rep), while the right encodes functions necessary for encapsidation (Cap). AAV vectors transduce many different types of cells. Multiple studies have amply demonstrated that rAAV vectors can transduce quiescent, nonproliferating targets. rAAV vectors do not encode any viral encoded genes, reducing their intrinsic immunogenicity. In addition, prolonged in vivo transgene expression following rAAV transduction has been documented in animal models. Finally, since its discovery in the mid-1960s, wild type AAV has yet to be definitively identified as a pathogen in either animals or humans.

The construction of recombinant adeno-associated virus ("rAAV") vectors has been described. See, e.g., U.S. Pat. Nos. 5,173,414 and 5,139,941; International Patent Publication Numbers WO 92/01070 (published Jan. 23, 1992) and WO 93/03769 (published Mar. 4, 1993); Lebkowski et al. (1988) Molec. Cell. Biol. 8:3988-3996; Vincent et al. (1990) Vaccines 90 (Cold Spring Harbor Laboratory Press); Carter, B. J. (1992) Current Opinion in Biotechnology 3:533-539; Muzyczka, N. (1992) Current Topics in Microbiol. and Immunol. 158:97-129; Kotin, R. M. (1994) Human Gene Therapy 5:793-801; Gao, G. (2002) Proc Natl Acad Sci USA 99:11854-11859; Hauck, B. (2003) Journal of Virology 77(4):2768-2774; and Gao, G. (2004) Journal of Virology 78(12):6381-6388.

Multiple schwannomas in peripheral distal and intracranial nerves are the hallmark of neurofibromatosis 1 and 2 (NF1 and NF2), and schwannomatosis, three types of nerve sheath tumors, classified as neurocutaneous syndromes, with incidences of about 1 in 3,200, 1 in 32,000 and 1 in 1,000,000, respectively (Antinheimo et al., 2000; Baser et al., 2006). Schwannomas are benign tumors composed of neoplastic dedifferentiated Schwann cells. Although typically nonmalignant and slow growing, these tumors can have devastating consequences for patients. They can cause extreme pain and compromise sensory/motor functions, including hearing and vision. Schwannomas in NF2 are frequently associated with neurological deficits, such as paresthesias, weakness, or hearing loss, and similar tumors in schwannomatosis often cause excruciating pain (Huang et al., 2004; Lu-Emerson and Plotkin, 2009). Some schwannomas become very large, causing compression of adjacent organs or structures, and can lead to paralysis or death due to progressive spinal cord or brainstem compression. Schwannomas may arise sporadically, without presenting any genetic features of NF1, NF2 and schwannomatosis. Most of vestibular schwannomas are sporadic schwannomas, so their incidence is very significant. Vestibular schwannomas usually occur as single tumors, not as multiple tumors throughout the body.

The underlying molecular abnormality in NF2 is a germline mutation of the NF2 gene. Somatic loss of the normal remaining NF2 allele in Schwann cells leads to deregulated growth of neoplastic Schwann cells with schwannoma formation (Rouleau et al., 1993). The timing of loss of the second wild-type allele may occur during development, as Schwann cells move out along axons and begin myelination, or in response to injury when Schwann cells dedifferentiate and commence proliferation (Jessen and Mirsky, 2005; McClatchey and Giovannini, 2005). In schwannomatosis some patients have a germline mutation in the SMARCB/IN11 gene with a second hit in Schwann cells leading to schwannoma formation (Hulsebos et al., 2007); in addition, the majority of these tumors harbor additional mutations in the NF2 gene (Jacoby et al., 1997; Hadfield et al., 2008). NF1, NF2 and schwannomatosis have three different genetic mutations, NF1, NF2 and INI, whereas no specific genetic mutation has been identified for sporadic schwannomas. The table below summarizes the features of these diseases that are all composed of Schwann cells and therefore amenable to various treatment methods described herein. In addition, their standard of care (as detailed below) is the same, and they all present the same need for new therapies.

| Disease | USA Prevalence | Cell composition | Genetic Mutation |
| --- | --- | --- | --- |
| Neurofibromatosis type 1 | 100,000 | Schwann & fibroblasts | NF1 |
| Sporadic Schwannoma | 30,000 | Schwann | Unknown |
| Neurofibromatosis type 2 | 10,000 | Schwann | Merlin (NF2) |
| Schwannomatosis | 6,000 | Schwann | INI 1 |

The standard of care for patients with NF2 and schwannomatosis is surgical resection or radiosurgery of symptomatic tumors to reduce tumor size. Unlike in the case of sporadic schwannomas, in which typically only a single tumor is present and surgery is generally an efficacious treatment strategy as long as the lesion is accessible for resection (Lu-Emerson and Plotkin, 2009), in schwannomatosis and NF2, which present with multiple tumors, resection is confounded by both the inaccessibility of many tumors and by risk of nerve damage, including major motor dysfunction, significant sensory loss (including deafness in the case of NF2 vestibular schwannomas), and neuropathic pain. Thus, for most individuals there is substantial morbidity associated with schwannomas in both NF2 and schwannomatosis, as well as with the current therapies. This suffering and debility, in combination with the paucity of therapeutic options, makes the treatment of schwannomas a major unmet medical need.

Of the caspases family of genes, caspases-3 is the most common target for therapeutic modulation. Unlike caspases-3, caspases-1 has a strong pro-inflammatory component in addition to induction of apoptosis. Caspase-1 activates pro-IL-1b and pro-IL-18, which in turn trigger immune responses mediated by neutrophils and monocytes, or NK cells. In addition, caspases-1 has been associated with both innate and adaptive immunity and is activated by several chemotherapeutic drugs which can sensitize tumors cells to chemotherapy and radiation.

In this invention, we provide gene therapies for treating tumors, particularly schwannomas and related conditions. As a non-limiting example, direct injection of an adeno-associated virus (AAV) serotype 1 vector encoding caspase-1 (ICE) under the Schwann cell specific promoter, P0, leads to regression of these tumors with essentially no vector-mediated neuropathology, and no changes in sensory or motor function. In a related NF2 xenograft model designed to cause measurable pain behavior, the same gene therapy leads to tumor regression and concordant resolution of tumor-associated pain. Gene therapies based on various AAV-P0-ICE vectors provide clinical treatment of schwannomas by direct intratumoral injection to achieve reduction in tumor size and normalization of neuronal function. Our gene therapies effectively reduce the tumor size and pain associated with single schwannomas without causing the neurological damage typically associated with surgery. It is a much less invasive technique than surgery. Also, because our gene therapies do not deliver the gene that is mutated in the specific diseases but a pyroptotic gene, any Schwann-cell derived tumor, independent from its tumorigenic mutation, can be treated by the approaches described herein.

SUMMARY

The following embodiments and aspects thereof are described and illustrated in conjunction with systems, compositions and methods which are meant to be exemplary and illustrative, not limiting in scope.

Various embodiments of the present invention provide a recombinant adeno-associated virus (rAAV) vector comprising a caspase-1 gene or a variant thereof and a Schwann cell specific promoter. In some embodiments, the vector may further comprise any one or more of human Caspase-4, human Caspase-5, and mouse Caspase-11, or variants thereof. Human Caspase-4, human Caspase-5 and mouse Caspase-11 are elements of the inflammasome and as such play a role in the induction of pyroptosis, and thus may have efficacy for use in conjunction with caspase-1. In some embodiments, the vector may further comprise genes or variants thereof involved in or associated with inflammasome activation (e.g., NLRP1, Nlrp3, NRLC4, NALP, AIM2, PYCARD-derived adaptor proteins CARD or ASC, IL-1B and/or IL-18). In accordance with the present invention, an additional gene (e.g., human Caspase-4, human Caspase-5, mouse Caspase-11, NLRP1, Nlrp3, NRLC4, NALP, AIM2, PYCARD-derived adaptor proteins CARD or ASC, IL-1B and IL-18) may be delivered by the same rAAV vector delivering the caspases-1 gene or a separate vector.

Various embodiments of the present invention provide a cell transfected with a rAAV vector comprising a caspase-1 gene or a variant thereof and a Schwann cell specific promoter. In some embodiments, the vector may further comprise any one or more of human Caspase-4, human Caspase-5, mouse Caspase-11, NLRP1, Nlrp3, NRLC4, NALP, AIM2, PYCARD-derived adaptor proteins CARD or ASC, IL-1B, and/or IL-18, or variants thereof. In some embodiments, the transfected cell may be co-transfected with vectors (for example AAV vectors) comprising any one or more of human Caspase-4, human Caspase-5, mouse Caspase-11, NLRP1, Nlrp3, NRLC4, NALP, AIM2, PYCARD-derived adaptor proteins CARD or ASC, IL-1B, and/or IL-18, or variants thereof.

Various embodiments of the present invention provide a supernatant obtained from a culture of a cell transfected with a rAAV vector comprising a caspase-1 gene or a variant thereof and a Schwann cell specific promoter. In some embodiments, the vector may further comprise any one or more of human Caspase-4, human Caspase-5, mouse Caspase-11, NLRP1, Nlrp3, NRLC4, NALP, AIM2, PYCARD-derived adaptor proteins CARD or ASC, IL-1B, and/or IL-18, or variants thereof. In some embodiments, the transfected cell may be co-transfected with vectors (for example AAV vectors) comprising any one or more of human Caspase-4, human Caspase-5, mouse Caspase-11, NLRP1, Nlrp3, NRLC4, NALP, AIM2, PYCARD-derived adaptor proteins CARD or ASC, IL-1B, and/or IL-18, or variants thereof.

Various embodiments of the present invention provide an extracellular vesicle isolated from a cell transfected with an rAAV vector comprising a caspase-1 gene or a variant thereof and a promoter. In accordance with the present invention, the promoter can be a Schwann cell specific promoter or a ubiquitous promoter. In some embodiments, the vector may further comprise any one or more of human Caspase-4, human Caspase-5, mouse Caspase-11, NLRP1, Nlrp3, NRLC4, NALP, AIM2, PYCARD-derived adaptor proteins CARD or ASC, IL-1B, and/or IL-18, or variants thereof. In some embodiments, the transfected cell may be co-transfected with vectors (for example AAV vectors) comprising any one or more of human Caspase-4, human Caspase-5, mouse Caspase-11, NLRP1, Nlrp3, NRLC4, NALP, AIM2, PYCARD-derived adaptor proteins CARD or ASC, IL-1B, and/or IL-18, or variants thereof.

Various embodiments of the present invention provide a pharmaceutical composition. The pharmaceutical composition comprises a rAAV vector comprising a caspase-1 gene or a variant thereof and a Schwann cell specific promoter, or a cell transfected with the rAAV vector, or supernatant conditioned with the transfected cell, or a extracellular vesicle isolated from the transfected cell, each of which as described herein. The pharmaceutical composition may also comprise a pharmaceutically acceptable carrier. In accordance with the present invention, the pharmaceutical composition may further comprise a chemotherapeutic agent.

Various embodiments of the present invention provide a method of treating, inhibiting, preventing, reducing the severity of and/or reducing the progression of a disease-state in a subject. The method comprises: providing a composition comprising a rAAV vector comprising a caspase-1 gene or a variant thereof and a Schwann cell specific promoter, or a composition comprising a cell transfected with the rAAV vector, or a composition comprising a supernatant conditioned with the transfected cell, or a composition comprising an extracellular vesicle isolated from the transfected cell; and administering a therapeutically effective amount of the composition to the subject, thereby treating, inhibiting, preventing, reducing the severity of and/or reducing the progression of the disease-state in the subject. In accordance with the present invention, an additional gene (e.g., human Caspase-4, human Caspase-5, mouse Caspase-11, NLRP1, Nlrp3, NRLC4, NALP, AIM2, PYCARD-derived adaptor proteins CARD or ASC, IL-1B and IL-18) may be delivered to the subject by the same rAAV vector, cell, supernatant or extracellular vesicle delivering the caspases-1 gene as described herein or a separate vector, cell, supernatant or extracellular vesicle.

Various embodiments of the present invention provide a method of treating, inhibiting, preventing, reducing the severity of and/or reducing the progression of a disease-state in a subject. The method comprises: providing an rAAV vector comprising a caspase-1 gene or a variant thereof and a Schwann cell specific promoter, or a cell transfected with the rAAV vector, or a supernatant conditioned with the transfected cell, or an extracellular vesicle isolated from the transfected cell; and administering a therapeutically effective amount of the rAAV vector, or the transfected cell, or the supernatant, or the extracellular vesicle to the subject, thereby treating, inhibiting, preventing, reducing the severity of and/or reducing the progression of the disease-state in the subject. In accordance with the present invention, an additional gene (e.g., human Caspase-4, human Caspase-5, mouse Caspase-11, NLRP1, Nlrp3, NRLC4, NALP, AIM2, PYCARD-derived adaptor proteins CARD or ASC, IL-1B and IL-18) may be delivered to the subject by the same rAAV vector, cell, supernatant or extracellular vesicle delivering the caspases-1 gene or a separate vector, cell, supernatant or extracellular vesicle.

Various treatment method of the present invention may further comprise treating the subject with surgery, radiation therapy, or chemotherapy, or a combination thereof.

Various embodiments of the present invention provide a kit for treating, inhibiting, preventing, reducing the severity of and/or reducing the progression of a disease-state in a subject. In some embodiments, the kit comprises: a composition comprising an rAAV vector comprising a caspase-1 gene or a variant thereof and a Schwann cell specific promoter, or a composition comprising a cell transfected with the rAAV vector, or a composition comprising a supernatant conditioned with the transfected cell, or a composition comprising an extracellular vesicle isolated from the transfected cell; and instructions for using the composition for treating, inhibiting, preventing, reducing the severity of and/or reducing the progression of a disease-state in a subject. In other embodiments, the kit comprises an rAAV vector comprising a caspase-1 gene or a variant thereof and a Schwann cell specific promoter, or a cell transfected with the rAAV vector, or a supernatant conditioned with the transfected cell, or an extracellular vesicle isolated from the transfected cell; and instructions for using the rAAV vector, or the transfected cell, or the supernatant, or the extracellular vesicle for treating, inhibiting, preventing, reducing the severity of and/or reducing the progression of a disease-state in a subject. In accordance with the present invention, the kit may further comprise a chemotherapeutic agent and instructions for the use of the chemotherapeutic agent together with the components described above for treating, inhibiting, preventing, reducing the severity of and/or reducing the progression of a disease-state in a subject.

BRIEF DESCRIPTION OF THE DRAWINGS

Exemplary embodiments are illustrated in referenced figures. It is intended that the embodiments and figures disclosed herein are to be considered illustrative rather than restrictive.

DETAILED DESCRIPTION

Figure 1:
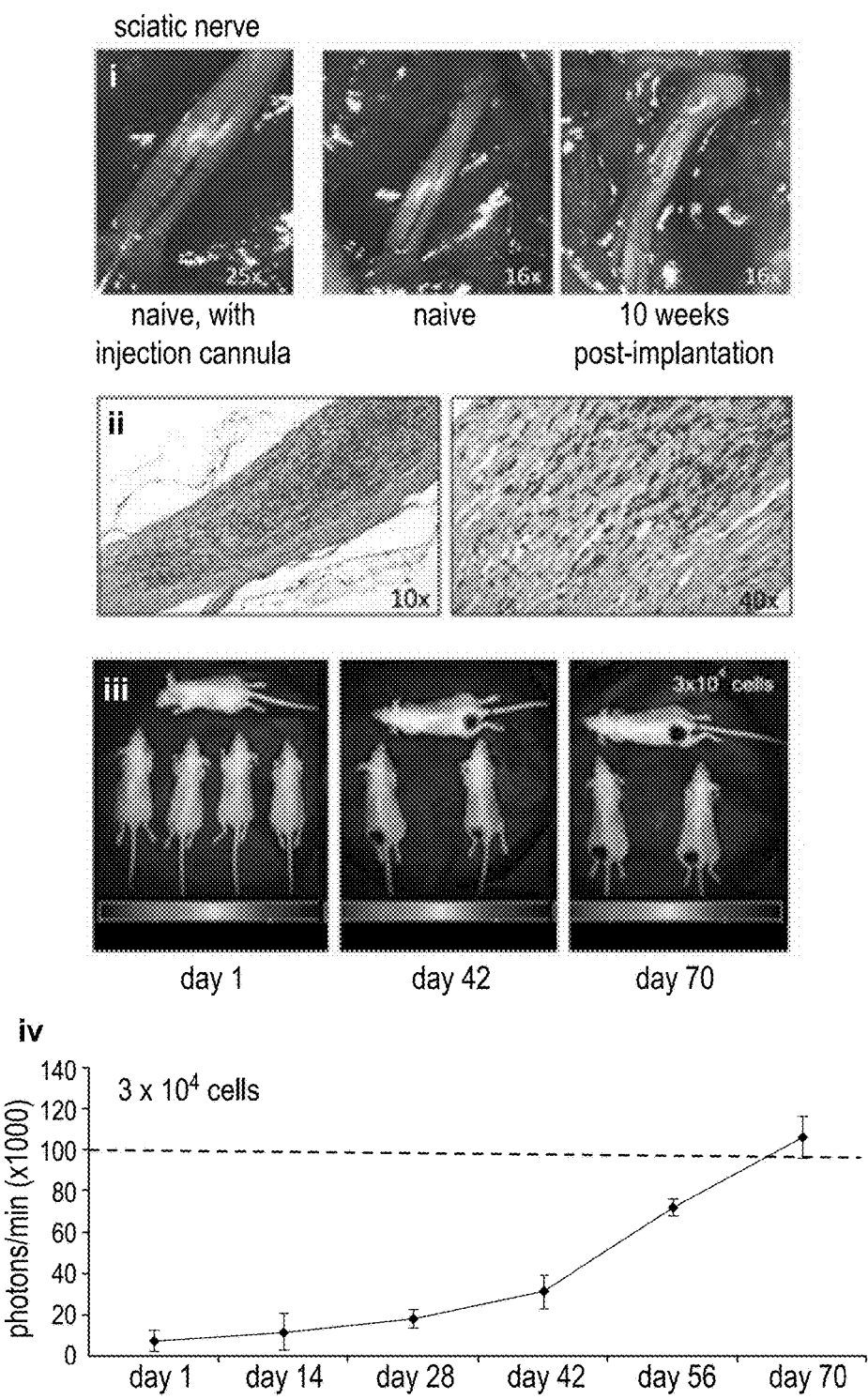
FIG. 1 depicts in accordance with various embodiments of the invention the sciatic nerve schwannoma model, NF2S-1 sciatic implantation model in immune-competent mice and the AAV vector encoding caspase-1 (interleukin-fl-converting enzyme; ICE) under the control of the P0 promoter. (A) i. HEI-193FC schwannoma cells were injected into the sciatic nerve using a glass micropipette and the tumor allowed to grow for 10 weeks. left panel, pipette next to an uninjected nerve; center panel, uninjected nerve; right panel, swollen nerve containing the tumor. ii. H&E staining of longitudinal section of sciatic nerve containing schwannoma tumor. iii. Following injection of schwannoma cells (30,000 in 1 µl), tumor progression was monitored using in vivo bioluminescence imaging. Images from five mice are shown with pseudocolor bar to indicate the degree of bioluminescence at 1, 42 and 70 days after tumor cell implantation. iv. Photon counts for tumors over time, quantified from bioluminescent images; mean+SD, N=5; (B) Thirty thousand NF2S-1 mouse schwannoma cells were implanted into the sciatic nerves of Swiss mice. Animals were sacrificed either 5 or 12 weeks later and sciatic nerves in the region of NF2S-1 cell implantation were processed for H&E staining. Histology demonstrates growth of NF2S-1 schwannoma cells (high cell density) within the implanted nerves; and (C) Shown is a schematic diagram of the self-complementary AAV1-P0-ICE vector carrying the expression cassette for mouse ICE (caspase-1) under the control of the rat Schwann cell-specific P0 promoter (P0), and the bovine growth hormone polyadenylation signal (pA). One AAV2 inverted terminal repeat (ITRd) carries a deletion of the terminal resolution site that allows it to be packaged as a double-stranded DNA molecule.
Figure 1:
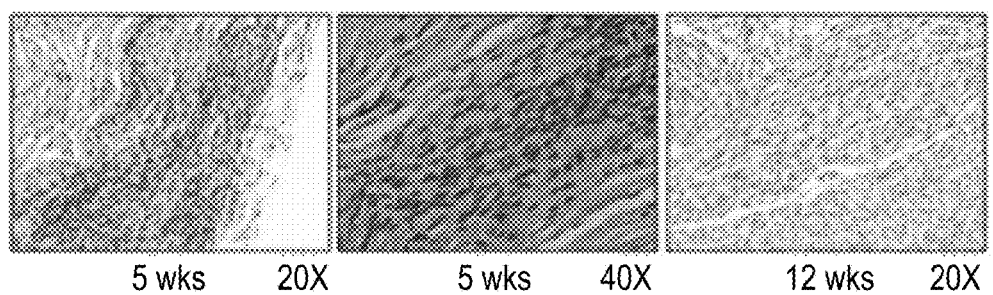
Figure 1:
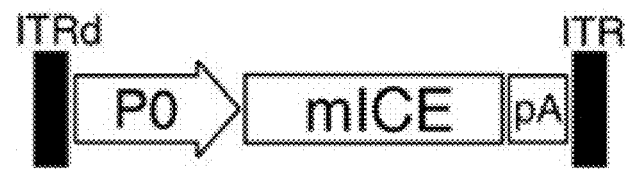

All references cited herein, including the references cited therein, are incorporated by reference in their entirety as though fully set forth. Unless defined otherwise, technical and scientific terms used herein have the same meaning as commonly understood by one of ordinary skill in the art to which this invention belongs. The practice of the present invention will employ, unless indicated specifically to the contrary, conventional methods of molecular biology and recombinant DNA techniques within the skill of the art, many of which are described below for the purpose of illustration. Such techniques are fully explained in the literature. See, e.g., Singleton et al., *Dictionary of Microbiology and Molecular Biology* $3^{rd}$ ed., J. Wiley & Sons (New York, N.Y. 2001); March, *Advanced Organic Chemistry Reactions, Mechanisms and Structure* $5^{th}$ ed., J. Wiley & Sons (New York, N.Y. 2001), Sambrook, et al., Molecular Cloning: A Laboratory Manual (3rd Edition, 2000); Sambrook and Russel, *Molecular Cloning: A Laboratory Manual* 3rd ed., Cold Spring Harbor Laboratory Press (Cold Spring Harbor, N.Y. 2001), DNA Cloning: A Practical Approach, vol. I & II (D. Glover, ed.); Oligonucleotide Synthesis (N. Gait, ed., 1984); Oligonucleotide Synthesis: Methods and Applications (P. Herdewijn, ed., 2004); Nucleic Acid Hybridization (B. Hames & S. Higgins, eds., 1985); Nucleic Acid Hybridization: Modern Applications (Buzdin and Lukyanov, eds., 2009); Transcription and Translation (B. Hames & S. Higgins, eds., 1984); Animal Cell Culture (R. Freshney, ed., 1986); Freshney, R. I. (2005) Culture of Animal Cells, a Manual of Basic Technique, 5th Ed. Hoboken N.J., John Wiley & Sons; B. Perbal, A Practical Guide to Molecular Cloning (3rd Edition 2010); Farrell, R., RNA Methodologies: A Laboratory Guide for Isolation and Characterization (3rd Edition 2005), Methods of Enzymology: DNA Structure Part A: Synthesis and Physical Analysis of DNA Methods in Enzymology, Academic Press; Using Antibodies: A Laboratory Manual: Portable Protocol NO. I by Edward Harlow, David Lane, Ed Harlow (1999, Cold Spring Harbor Laboratory Press, ISBN 0-87969-544-7); Antibodies: A Laboratory Manual by Ed Harlow (Editor), David Lane (Editor) (1988, Cold Spring Harbor Laboratory Press, ISBN 0-87969-3, 4-2), 1855. Handbook of Drug Screening, edited by Ramakrishna Seethala, Prabhavathi B. Fernandes (2001, New York, N.Y., Marcel Dekker, ISBN 0-8247-0562-9); and Lab Ref: A Handbook of Recipes, Reagents, and Other Reference Tools for Use at the Bench, Edited Jane Roskams and Linda Rodgers, (2002, Cold Spring Harbor Laboratory, ISBN 0-87969-630-3) provide one skilled in the art with a general guide to many of the terms used in the present application.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

As used herein, the terms "treat," "treatment," "treating," or "amelioration" when used in reference to a disease, disorder or medical condition, refer to therapeutic treatments for a condition, wherein the object is to reverse, alleviate, ameliorate, inhibit, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a disease-state is reduced or halted. That is, "treatment" includes not just the improvement of symptoms or markers, but also a cessation or at least slowing of progress or worsening of symptoms that would be expected in the absence of treatment.

Beneficial or desired clinical results include, but are not limited to, alleviation of one or more symptom(s), diminishment of extent of the deficit, stabilized (i.e., not worsening) state of cancer progression, delay or slowing of metastasis or invasiveness, and amelioration or palliation of symptoms associated with the cancer. Treatment also includes a decrease in mortality or an increase in the lifespan of a subject as compared to one not receiving the treatment.

As used herein, the term "administering," refers to the placement an agent as disclosed herein into a subject by a method or route which results in at least partial localization of the agents at a desired site.

A "cancer" or "tumor" as used herein refers to an uncontrolled growth of cells which interferes with the normal functioning of the bodily organs and systems. A subject that has a cancer or a tumor is a subject having objectively measurable cancer cells present in the subject's body. Included in this definition are benign and malignant cancers, as well as dormant tumors or micrometastatses. Cancers which migrate from their original location and seed vital organs can eventually lead to the death of the subject through the functional deterioration of the affected organs. As used herein, the term "carcinoma" refers to a cancer arising from epithelial cells. As used herein, the term "invasive" refers to the ability to infiltrate and destroy surrounding tissue. Melanoma is an invasive form of skin tumor.

The term "sample" or "biological sample" as used herein denotes a sample taken or isolated from a biological organism, e.g., a tumor sample from a subject. Exemplary biological samples include, but are not limited to, a biofluid sample; serum; plasma; urine; saliva; a tumor sample; a tumor biopsy and/or tissue sample etc. The term also includes a mixture of the above-mentioned samples. The term "sample" also includes untreated or pretreated (or pre-processed) biological samples. In some embodiments, a sample can comprise one or more cells from the subject. In some embodiments, a sample can be a tumor cell sample, e.g. the sample can comprise cancerous cells, cells from a tumor, and/or a tumor biopsy.

The term "functional" when used in conjunction with "derivative" or "variant" or "fragment" refers to a polypeptide which possess a biological activity that is substantially similar to a biological activity of the entity or molecule of which it is a derivative or variant or fragment thereof. By "substantially similar" in this context is meant that at least 25%, at least 35%, at least 50% of the relevant or desired biological activity of a corresponding Gal-1hFc fusion protein is retained.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. The mammal can be a human, non-human primate, mouse, rat, dog, cat, horse, or cow, but are not limited to these examples. In addition, the methods described herein can be used to treat domesticated animals and/or pets.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

A subject can be one who has been previously diagnosed with or identified as suffering from or having a disease-state in need of monitoring (e.g., schwannoma) or one or more complications related to such a disease-state, and optionally, have already undergone treatment for the disease-state or the one or more complications related to the disease/condition. Alternatively, a subject can also be one who has not been previously diagnosed as having a disease-state or one or more complications related to the disease/condition. For example, a subject can be one who exhibits one or more risk factors for a disease-state or one or more complications related to a disease-state or a subject who does not exhibit risk factors. A "subject in need" of treatment for a particular disease-state can be a subject having that disease/condition, diagnosed as having that condition, or at risk of developing that disease.

As used herein, the word "toxic" means effects on cells (e.g., tumor cells) that result in cell death, reduced ability to divide, or cell population reduction.

The term "statistically significant" or "significantly" refers to statistical evidence that there is a difference. It is defined as the probability of making a decision to reject the null hypothesis when the null hypothesis is actually true. The decision is often made using the p-value.

As used herein, "variants" can include, but are not limited to, those that include conservative amino acid mutations, SNP variants, splicing variants, degenerate variants, and biologically active portions of a gene. A "degenerate variant" as used herein refers to a variant that has a mutated nucleotide sequence, but still encodes the same polypeptide due to the redundancy of the genetic code. In accordance with the present invention, the caspase-1 gene may be modified, for example, to facilitate identification and/or improve expression, so long as such modifications do not reduce caspase-1's function to unacceptable level. In various embodiments, a variant of the caspases-1 gene encodes a protein that has at least 10%, 20%, 30%, 40%, 50%, 60%, 70%, 80%, 90%, or 95% of the function of a wild-type caspases-1 protein.

"Gene transfer" or "gene delivery" refers to methods or systems for reliably inserting foreign DNA into host cells. Such methods can result in transient expression of non-integrated transferred DNA, extrachromosomal replication and expression of transferred replicons (e.g., episomes), or integration of transferred genetic material into the genomic DNA of host cells. Gene transfer provides a unique approach for the treatment of acquired and inherited diseases. A number of systems have been developed for gene transfer into mammalian cells. See, e.g., U.S. Pat. No. 5,399,346.

"Vector" refers to any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

"rAAV vector" refers to any vector derived from any adeno-associated virus serotype, including, without limitation, AAV-1, AAV-2, AAV-3, AAV-4, AAV-5, AAV-7 and AAV-8, and the like. rAAV vectors can have one or more of the AAV wild-type genes deleted in whole or in part, preferably the Rep and/or Cap genes, but retain functional flanking ITR sequences. Functional ITR sequences are generally necessary for the rescue, replication, packaging and potential chromosomal integration of the AAV genome. Thus, a rAAV vector is defined herein to include at least those sequences required in cis for replication and packaging (e.g., functional ITRs) of the virus. The ITRs need not be the wild-type nucleotide sequences, and may be altered (e.g., by the insertion, deletion or substitution of nucleotides) so long as the sequences provide for functional rescue, replication and packaging.

"Recombinant virus" refers to a virus that has been genetically altered (e.g., by the addition or insertion of a heterologous nucleic acid construct into the particle).

"AAV virion" refers to a complete virus particle, such as a wild-type ("wt") AAV virus particle (i.e., including a linear, single-stranded AAV nucleic acid genome associated with an AAV capsid protein coat). In this regard, single-stranded AAV nucleic acid molecules of either complementary sense (i.e., "sense" or "antisense" strands) can be packaged into any one AAV virion; both strands are equally infectious. In addition, the AAV capsid protein coat can be from any of the various AAV serotypes depending on the target of the AAV virion.

A "recombinant AAV virion" or "rAAV virion" is defined herein as an infectious, replication-defective virus composed of an AAV protein shell, encapsidating a heterologous DNA molecule of interest (e.g., genes encoding caspase-1) which is flanked on both sides by AAV ITRs. A rAAV virion may be produced in a suitable host cell which has had an rAAV vector, AAV Rep and Cap functions and helper virus functions introduced therein. In this manner, the host cell is rendered capable of producing AAV replication and capsid proteins that are required for replicating and packaging the rAAV vector (i.e., containing a recombinant nucleotide sequence of interest) into recombinant virion particles for subsequent gene delivery. The complete transgene may consist of a promoter, the coding sequences, usually a cDNA and a polyadenylation signal. A transgene may also include regulatory sequences and intron regions. Promoters that would regulate transgene expression may include constitutive, inducible and tissue-specific promoters.

The term "transfection" is used herein to refer to the uptake of foreign DNA by a cell. A cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous DNA moieties, such as a plasmid vector and other nucleic acid molecules, into suitable host cells. The term refers to both stable and transient uptake of the genetic material.

The term "transduction" denotes the delivery of a DNA molecule to a recipient cell either in vivo or in vitro, via any method of gene delivery, including replication-defective viral vectors, such as via a rAAV. For example, transduction could mean uptake of a virus, part of which is DNA.

The term "heterologous," as it relates to nucleic acid sequences such as gene sequences and control sequences, denotes sequences that are not normally joined together and/or are not normally associated with a particular virus. Allelic variation or naturally occurring mutational events do not give rise to heterologous DNA, as used herein.

"DNA" is meant to refer to a polymeric form of deoxyribonucleotides (i.e., adenine, guanine, thymine and cytosine) in double-stranded or single-stranded form, either relaxed or supercoiled. This term refers only to the primary and secondary structure of the molecule, and does not limit it to any particular tertiary forms. Thus, this term includes single- and double-stranded DNA found, inter alia, in linear DNA molecules (e.g., restriction fragments), viruses, plasmids, and chromosomes. In discussing the structure of particular DNA molecules, sequences may be described herein according to the normal convention of giving only the sequence in the 5' to 3' direction along the non-transcribed strand of DNA (i.e., the strand having the sequence homologous to the mRNA). The term captures molecules that include the four bases adenine, guanine, thymine and cytosine, as well as molecules that include base analogues which are known in the art.

A "gene" or "coding sequence" or a sequence which "encodes" a particular protein is a nucleic acid molecule that is transcribed (in the case of DNA) and translated (in the case of mRNA) into a polypeptide in vitro or in vivo when placed under the control of appropriate regulatory sequences; although one of skill in the art will readily appreciate that various polynucleotides do not operate in this fashion (e.g., antisense RNA, siRNA, ribozymes, wherein the RNA transcript is the product). With respect to protein products (i.e., not RNA products), the boundaries of the coding sequence are determined by a start codon at the 5' (i.e., amino) terminus and a translation stop codon at the 3' (i.e., carboxy) terminus. A gene can include, but is not limited to, cDNA from prokaryotic or eukaryotic mRNA, genomic DNA sequences from prokaryotic or eukaryotic DNA, and even synthetic DNA sequences. A transcription termination sequence will usually be located 3' to the gene sequence. Moreover, a "gene" (i) starts with a promoter region containing multiple regulatory elements, possibly including enhancers, for directing transcription of the coding region sequences; (ii) includes coding sequences, which start at the transcriptional start site that is located upstream of the translational start site and ends at the transcriptional stop site, which may be quite a bit downstream of the stop codon (a polyadenylation signal is usually associated with the transcriptional stop site and is located upstream of the transcriptional stop); and (iii) may contain introns and other regulatory sequences to modulate expression and improve stability of the RNA transcript. Still in accordance with the present invention, a "gene" may refers to a sequence encoding a protein, such as caspase-1.

The term "control elements" refers collectively to promoter regions, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control elements need always be present, so long as the selected coding sequence is capable of being replicated, transcribed and translated in an appropriate host cell.

The term "promoter region" is used herein in its ordinary sense to refer to a nucleotide region including a DNA regulatory sequence, wherein the regulatory sequence is derived from a gene which is capable of binding RNA polymerase and initiating transcription of a downstream (3'-direction) coding sequence.

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

For the purpose of describing the relative position of nucleotide sequences in a particular nucleic acid molecule throughout the instant application, such as when a particular nucleotide sequence is described as being situated "upstream," "downstream," "5'," or "3'" relative to another sequence, it is to be understood that it is the position of the sequences in the non-transcribed strand of a DNA molecule that is being referred to as is conventional in the art.

"Homology" and "homologous" as used herein refer to the percent of identity between two polynucleotide or two polypeptide moieties. The correspondence between the sequence from one moiety to another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions which form stable duplexes between homologous regions, followed by digestion with single-stranded-specific nuclease(s), and size determination of the digested fragments. Two DNA or two polypeptide sequences are "substantially homologous" to each other when at least about 80%, preferably at least about 90%, and most preferably at least about 95% of the nucleotides or amino acids, respectively, match over a defined length of the molecules, as determined using the methods above.

"Isolated" as used herein when referring to a nucleotide sequence, vector, etc., refers to the fact that the indicated molecule is present in the substantial absence of other biological macromolecules of the same type. Thus, an "isolated nucleic acid molecule which encodes a particular polypeptide" refers to a nucleic acid molecule that is substantially free of other nucleic acid molecules that do not encode the subject polypeptide. Likewise, an "isolated vector" refers to a vector that is substantially free of other vectors that differ from the subject vector. However, the subject molecule or vector may include some additional bases or moieties that do not deleteriously affect the basic characteristics of the composition.

"Purified" as used herein when referring to a vector, refers to a quantity of the indicated vector that is present in the substantial absence of other biological macromolecules. Thus, a "purified vector" refers to a composition that includes at least 80% subject vector, preferably at least 90% subject vector, most preferably at least 95% subject vector with respect to other components of the composition.

Extracellular vesicles (EVs, including but are not limited to exosomes, microvesicles, microparticles, circulating microvesicles, shedding microvesicles, nanovesicles, nanoparticles, apoptotic bodies, and membrane vesicles) are fragments of plasma membrane ranging from for example, 20 nm to 10 µm, shed from almost all cell types. Microvesicles play a role in intercellular communication and can transport mRNA, miRNA, and proteins between cells. As will be apparent to a person of skill in the art, there are various EV isolation and purification protocols based on filtration, differential centrifugation, ultracentrifugation, flotation of vesicles in gradients (sucrose, OptiPrep™), and immunoaffinity capture utilizing antibodies against membrane proteins. Exemplary information for isolating extracelluar vesicles may be found in Simpson R J, Mathivanan S (2012) Extracellular Microvesicles: The Need for Internationally Recognised Nomenclature and Stringent Purification Criteria. J Proteomics Bioinform 5: ii-ii; van der Pol et al., Classification, functions, and clinical relevance of extracellular vesicles, Pharmacol Rev. 2012 July; 64(3):676-705; Raposo and Stoorvogel, Extracellular vesicles: exosomes, microvesicles, and friends, J Cell Biol. 2013 Feb. 18; 200(4):373-83; and Witwer et al., Standardization of sample collection, isolation and analysis methods in extracellular vesicle research, J Extracell Vesicles. 2013 May 27; 2, which are incorporated herein by reference in their entirety. Also, see Sarkar el al., 2009, Taylor and Gercel-Taylor, 2008, and Balaj et al., 2011, which are incorporated herein by reference in their entirety.

As a non-limiting example, a filtration-based method may be used and the type and size of filters and columns will be apparent to a person of skill in the art. For example centrifugal ultracentrifugation devices covering sample volumes from 500 µl to 2 ml with any type of low-protein retentions and wide pH-range (e.g. 2-12 pH) filter membranes, such as polyethersulfone (PES) can be used. The nominal size of the pores can range between any one or more of 0.1 µm to 1 µm, 0.2 µm to 1 µm, 0.3 µm to 1 µm, 0.4 µm to 1 µm, 0.5 µm to 1 µm, 0.6 µm to 1 µm, 0.7 µm to 1 µm, 0.8 µm to 1 µm or 0.9 µm to 1 µm. In comparison with an ultracentrifugation based protocol, in which extracellular vesicles (EV) are recovered from the supernatant after centrifugation at 10,000 g/30 min or 100,000 g/60 min, a filtration protocol can filter supernatant at 8,000 g/30 sec using Vivaspin ultrafiltration spin columns.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

Schwannoma tumors are composed of Schwann-lineage cells and form along peripheral, spinal and cranial nerves. These tumors can cause pain, sensory/motor dysfunction, and death through compression of peripheral nerves, the spinal cord, and/or the brain stem. In initial studies, we used a mouse schwannoma model in which an immortalized cell line derived from human NF2 schwannoma cells (HEI-193) (Hung et al., 2002) was genetically modified to express firefly luciferase (Fluc) and the fluorescent protein, mCherry (designated HEI-193FC), and implanted subcutaneously in nude mice. Using this model, we demonstrated that intratumoral injection of a herpes simplex virus-1 (HSV-1) amplicon vector expressing the apoptotic protein caspase-1 (interleukin-β-converting enzyme; IL1-converting enzyme; ICE) under the Schwann cell specific P0 promoter led to tumor regression (Prabhakar et al., 2010). This gene therapy approach had two limitations; the subcutaneous location used was not clinically relevant and the HSV amplicon vector employed has never been used in clinical trials.

In the present invention, we used a tumor model in which human HEI-193FC schwannoma cells are implanted into the sciatic nerve of nude mice (Saydam et al., 2011). We used recombinant adeno-associated viral (AAV) vectors, which are well established as safe in clinical trials, and found that among the serotypes tested by direct injection into the mouse sciatic nerve (AAV1, AAVrh8, AAVrh10), AAV1 proved to be the most efficient in transducing Schwann cells (M.S.E. and G.J.B.). Here, we demonstrate that direct injection of an AAV1-P0-ICE vector into intrasciatic distal schwannomas both prevented tumor development and led to regression of well-established tumors, as assessed by in vivo bioluminescence imaging and correlative histopathology. Tumors injected with a control vector, AAV1-P0-GFP, continued to grow. In a proximal sciatic nerve reimplantation model, designed to cause pain-like behavior as assessed by plantar von Frey withdrawal threshold (i.e., mechanical sensitization), intratumoral AAV1-P0-ICE injection alleviated pain sensitivity in parallel with regression of tumors. Neuropathological evaluation of Epon and paraffin sections of sciatic nerves of both nude and immunocompetent mice injected with AAV1-P0-ICE showed no evidence of inflammation or axonal degeneration, and only rare macrophages, consistent with the absence of behavioral changes in pain sensitivity or motor skills in these vector-injected animals.

Our data indicate that AAV1-P0-ICE not only induces apoptosis of infected caspase-1-expressing HEI-193 schwannoma cells, but also kills non-infected tumor cells through a bystander effect mediated by both tumor- and host-specific mechanisms. Supernatants derived from HEI-193 cells transfected with AAV1-P0-ICE DNA kill non-transfected tumor cells in vitro. Similarly, peripheral nerve implantation of a 1:1 mixture of AAV-P0-ICE DNA-transfected and non-transfected HEI-193 cells prevented tumor growth. This bystander killing effect induced by AAV1-P0-ICE was also observed when established intra-sciatic HEI-193 tumors were injected with AAV1-P0-ICE transfected cells. Interestingly, intra-sciatic implantation of HEI-193 cells 2 weeks after injection at the same location of AAV1-P0-ICE DNA-transfected cells, i.e. long after all of the originally implanted caspase-1 expressing HEI-193 cells should be dead, also prevents formation of a tumor. These data suggest that caspase-1-induced death of HEI-193 cells in vivo leads to local changes in the region of the tumor capable of preventing formation of a subsequent tumor.

AAV1-P0-ICE-induced bystander killing of tumor cells could be utilized as new therapeutics for the neurofibromatoses, as well as, for other benign neoplasms. Not only can caspase-1 induce apoptosis, but the resulting tumor killing and associated activation of host immune responses may generate a vaccination effect that could control the development and growth of subsequent schwannomas.

rAAV Vectors, Cells, Supernatants and Extracellular Vesicles

In various embodiments, the present invention provides a recombinant adeno-associated virus (rAAV) vector comprising a caspase-1 gene or a variant thereof and a Schwann cell specific promoter. In some embodiments, the vector may further comprise any one or more of human Caspase-4, human Caspase-5, and mouse Caspase-11, or variants thereof. Human Caspase-4, human Caspase-5 and mouse Caspase-11 are elements of the inflammasome and as such play a role in the induction of pyroptosis, and thus may have efficacy for use in conjunction with caspase-1. In some embodiments, the vector may further comprise genes or variants thereof involved in or associated with inflammasome activation (e.g., NLRP1, Nlrp3, NRLC4, NALP, AIM2, PYCARD-derived adaptor proteins CARD or ASC, IL-1B and/or IL-18). In accordance with the present invention, an additional gene (e.g., human Caspase-4, human Caspase-5, mouse Caspase-11, NLRP1, Nlrp3, NRLC4, NALP, AIM2, PYCARD-derived adaptor proteins CARD or ASC, IL-1B and IL-18) may be delivered by the same rAAV vector delivering the caspases-1 gene or a separate vector.

In various embodiments, the present invention provides a cell transfected with an rAAV vector comprising a caspase-1 gene or a variant thereof and a Schwann cell specific promoter. In various embodiments, the cell is a schwannoma cell or a Schwann cell. In some embodiments, the vector may further comprise any one or more of human Caspase-4, human Caspase-5, mouse Caspase-11, NLRP1, Nlrp3, NRLC4, NALP, AIM2, PYCARD-derived adaptor proteins CARD or ASC, IL-1B, and/or IL-18, or variants thereof. In some embodiments, the transfected cell may be co-transfected with vectors (for example AAV vectors) comprising any one or more of human Caspase-4, human Caspase-5, mouse Caspase-11, NLRP1, Nlrp3, NRLC4, NALP, AIM2, PYCARD-derived adaptor proteins CARD or ASC, IL-1B, and/or IL-18, or variants thereof.

In various embodiments, the present invention provides a supernatant obtained from a culture of a cell transfected with an rAAV vector comprising a caspase-1 gene or a variant thereof and a Schwann cell specific promoter. In various embodiments, the cell is a schwannoma cell or a Schwann cell. In various embodiments, the transfected cell is cultured for about 12-24, 24-48, or 48-73 hours. In various embodiments, the supernatant comprises extracellular vesicles released from the transfected cell. In some embodiments, the vector may further comprise any one or more of human Caspase-4, human Caspase-5, mouse Caspase-11, NLRP1, Nlrp3, NRLC4, NALP, AIM2, PYCARD-derived adaptor proteins CARD or ASC, IL-1B, and/or IL-18, or variants thereof. In some embodiments, the transfected cell may be co-transfected with vectors (for example AAV vectors) comprising any one or more of human Caspase-4, human Caspase-5, mouse Caspase-11, NLRP1, Nlrp3, NRLC4, NALP, AIM2, PYCARD-derived adaptor proteins CARD or ASC, IL-1B, and/or IL-18, or variants thereof.

In various embodiments, the present invention provides an extracellular vesicle isolated from a cell transfected with an rAAV vector comprising a caspase-1 gene or a variant thereof and a promoter. In accordance with the present invention, the promoter can be a Schwann cell specific promoter (e.g., a P0 promoter and a PMP22 promoter) or a ubiquitous promoter (e.g., CMV, CBA/CAG, and EF1a promoters). In various embodiments, the cell is a schwannoma cell or a Schwann cell. In various embodiments, the transfected cell is cultured for about 12-24, 24-48, or 48-73 hours. In some embodiments, the vector may further comprise any one or more of human Caspase-4, human Caspase-5, mouse Caspase-11, NLRP1, Nlrp3, NRLC4, NALP, AIM2, PYCARD-derived adaptor proteins CARD or ASC, IL-1B, and/or IL-18, or variants thereof. In some embodiments, the transfected cell may be co-transfected with vectors (for example AAV vectors) comprising any one or more of human Caspase-4, human Caspase-5, mouse Caspase-11, NLRP1, Nlrp3, NRLC4, NALP, AIM2, PYCARD-derived adaptor proteins CARD or ASC, IL-1B, and/or IL-18, or variants thereof.

In various embodiments, the caspase-1 gene can be a human, mouse, or rat caspase-1, but is not limited to these examples. In various embodiments, the variant of a caspase-1 gene can be a variant of a human, mouse, or rat caspase-1, but is not limited to these examples. An exemplar sequence of a human caspase-1 gene is set forth in SEQ ID NO. 1; an exemplar sequence of a mouse caspase-1 gene is set forth in SEQ ID NO. 2; and an exemplar sequence of a rat caspase-1 gene is set forth in SEQ ID NO. 3.

In various embodiments, the Schwann cell specific promoter comprises a P0 promoter or a peripheral myelin protein 22 (PMP22) promoter. In various embodiments, the Schwann cell specific promoter is upstream of the caspase-1 gene or the variant thereof. In accordance with the present invention, the caspase-1 gene or the variant thereof and the Schwann cell specific promoter are operably linked. In various embodiments, the Schwann cell specific promoter can be a human, mouse, or rat promoter (e.g., human P0 promoter, human PMP22 promoter, mouse P0 promoter, mouse PMP22 promoter, rat P0 promoter, and rat PMP22 promoter, or hybrids thereof). An exemplar sequence of a rat P0 promoter is set forth in SEQ ID NO.: 8. An exemplar sequence of a mouse P0 promoter is set forth in SEQ ID NO.: 16. An exemplar sequence of a human P0 promoter is set forth in SEQ ID NO.: 17. Exemplar sequences of human, mouse, and rat P0 genes are set forth in SEQ ID NO.: 9-11, respectively.

In various embodiments, the rAAV vector further includes a polyadenylation signal. In various embodiments, the polyadenylation signal is downstream of the caspase-1 gene or the variant thereof. In various embodiments, the polyadenylation signal includes a bovine growth hormone polyadenylation signal, a SV40 polyadenylation signal or a rabbit beta-globin polyadenylation signal. In accordance with the present invention, the caspase-1 gene or the variant thereof and the polyadenylation signal are operably linked.

In various embodiments, the rAAV vector further includes a first AAV inverted terminal repeat (ITR) located upstream of the Schwann cell specific promoter and a second AAV ITR located downstream of the polyadenylation signal. In accordance with the present invention, the first or second AAV inverted terminal repeat can include a deletion of the terminal resolution site. In accordance with the present invention, the first and second ITRs, the Schwann cell specific promoter, the caspase-1 gene or the variant thereof, and the polyadenylation signal are operably linked to constitute a functional rAAV vector capable of delivering caspase-1 or a variant thereof to Schwannomas.

In various embodiments, the rAAV vector includes a sequence as set forth in SEQ ID NO.4 (P0-humanICE) or a variant thereof. In various embodiments, the rAAV vector includes a sequence as set forth in SEQ ID NO.5 (P0-mouseICE) or a variant thereof. In various embodiments, the rAAV vector includes a sequence as set forth in SEQ ID NO.6 or a variant thereof. In various embodiments, the rAAV vector includes a sequence as set forth in SEQ ID NO.7 or a variant thereof.

In various embodiments, the rAAV vector is a polynucleotide. In various embodiments, the rAAV vector is a single-stranded or double-stranded AAV. In various embodiments, the rAAV vector is a self-complementary AAV (scAAV).

In various embodiments, the rAAV vector is a virus particle. In accordance with the present invention, the serotype of the virus particle is AAV1, AAV2, AAV3, AAV4, AAV5, AAV6, AAV7, AAV8, AAV9, AAV10, AAV11, or AAV12, or a hybrid serotype thereof.

Pharmaceutical Composition

In various embodiments, the present invention provides a pharmaceutical composition. The pharmaceutical composition includes an rAAV vector comprising a caspase-1 gene or a variant thereof and a Schwann cell specific promoter; and a pharmaceutically acceptable carrier. In various embodiments, the concentration of the rAAV vector is about $1\times10^{7}$-$1\times10^{12}$, $1\times10^{7}$-$1\times10^{10}$, $1\times10^{10}$-$1\times10^{12}$, $1\times10^{12}$-$1\times10^{15}$, or $1\times10^{15}$-$1\times10^{18}$ genome copies (gc) per µl of the pharmaceutical composition.

In various embodiments, the present invention provides a pharmaceutical composition. The pharmaceutical composition includes a cell transfected with an rAAV vector comprising a caspase-1 gene or a variant thereof and a Schwann cell specific promoter; and a pharmaceutically acceptable carrier. In various embodiments, the cell is a schwannoma cell or a Schwann cell.

In various embodiments, the present invention provides a pharmaceutical composition. The pharmaceutical composition includes supernatant obtained from a culture of a cell transfected with an rAAV vector comprising a caspase-1 gene or a variant thereof and a Schwann cell specific promoter; and a pharmaceutically acceptable carrier. In various embodiments, the cell is a schwannoma cell or a Schwann cell. In various embodiments, the transfected cell is cultured for about 12-24, 24-48, or 48-73 hours. In various embodiments, the supernatant comprises extracellular vesicles released from the transfected cell.

In various embodiments, the present invention provides a pharmaceutical composition. The pharmaceutical composition includes an extracellular vesicle isolated from a cell transfected with an rAAV vector comprising a caspase-1 gene or a variant thereof and a promoter; and a pharmaceutically acceptable carrier. In accordance with the present invention, the promoter can be a Schwann cell specific promoter (e.g., a P0 promoter and a PMP22 promoter) or a ubiquitous promoter (e.g., CMV, CBA/CAG, and EF1a promoters). In various embodiments, the cell is a schwannoma cell or a Schwann cell. In various embodiments, the transfected cell is cultured for about 12-24, 24-48, or 48-73 hours.

In various embodiments, the pharmaceutical composition may further include a chemotherapeutic agent. Examples of chemotherapeutic agents include but are not limited to any one or more of cyclophosphamide, vincristine, imidazole carboxamide, cisplatin, carboplatin, etoposide, gemcitabine, docetaxel, trabectedin, anthracycline, doxorubicin, ifosfamide, cycloxygenase inhibitors, non-steroidal anti-inflammatory agents or combinations thereof.

In various embodiments, the caspase-1 gene can be a human, mouse, or rat caspase-1, but is not limited to these examples. In various embodiments, the variant of a caspase-1 gene can be a variant of a human, mouse, or rat caspase-1, but is not limited to these examples.

In various embodiments, the caspase-1 gene can be a human, mouse, or rat caspase-1, but is not limited to these examples. In various embodiments, the variant of a caspase-1 gene can be a variant of a human, mouse, or rat caspase-1, but is not limited to these examples. An exemplar sequence of a human caspase-1 gene is set forth in SEQ ID NO. 1; an exemplar sequence of a mouse caspase-1 gene is set forth in SEQ ID NO. 2; and an exemplar sequence of a rat caspase-1 gene is set forth in SEQ ID NO. 3.

In various embodiments, the Schwann cell specific promoter comprises a P0 promoter or a peripheral myelin protein 22 (PMP22) promoter. In various embodiments, the Schwann cell specific promoter is upstream of the caspase-1 gene or the variant thereof. In accordance with the present invention, the caspase-1 gene or the variant thereof and the Schwann cell specific promoter are operably linked. In various embodiments, the Schwann cell specific promoter can be a human, mouse, or rat promoter (e.g., human P0 promoter, human PMP22 promoter, mouse P0 promoter, mouse PMP22 promoter, rat P0 promoter, and rat PMP22 promoter, or hybrids thereof). An exemplar sequence of a rat P0 promoter is set forth in SEQ ID NO.: 8. An exemplar sequence of a mouse P0 promoter is set forth in SEQ ID NO.: 16. An exemplar sequence of a human P0 promoter is set forth in SEQ ID NO.: 17. Exemplar sequences of human, mouse, and rat P0 genes are set forth in SEQ ID NOs.: 9-11, respectively.

In various embodiments, the rAAV vector further includes a polyadenylation signal. In various embodiments, the polyadenylation signal is downstream of the caspase-1 gene or the variant thereof. In various embodiments, the polyadenylation signal includes a bovine growth hormone polyadenylation signal, a SV40 polyadenylation signal or a rabbit beta-globin polyadenylation signal. In accordance with the present invention, the caspase-1 gene or the variant thereof and the polyadenylation signal are operably linked.

In various embodiments, the rAAV vector further comprises a first AAV inverted terminal repeat (ITR) located upstream of the Schwann cell specific promoter and a second AAV ITR located downstream of the polyadenylation signal. In accordance with the present invention, the first or second AAV inverted terminal repeat can comprise a deletion of the terminal resolution site. In accordance with the present invention, the first and second ITRs, the Schwann cell specific promoter, the caspase-1 gene or the variant thereof, and the polyadenylation signal are operably linked to constitute a functional rAAV vector capable of delivering caspase-1 or a variant thereof to Schwannomas.

In various embodiments, the rAAV vector comprises a sequence as set forth in SEQ ID NO.:4 (P0-humanICE) or a variant thereof. In various embodiments, the rAAV vector comprises a sequence as set forth in SEQ ID NO.: 5 (P0-mouseICE) or a variant thereof. In various embodiments, the rAAV vector comprises a sequence as set forth in SEQ ID NO.: 6 or a variant thereof. In various embodiments, the rAAV vector comprises a sequence as set forth in SEQ ID NO.: 7 or a variant thereof.

In various embodiments, the rAAV vector is a polynucleotide. In various embodiments, the rAAV vector is a single-stranded or double-stranded AAV. In various embodiments, the rAAV vector is a self-complementary AAV (scAAV).

In various embodiments, the rAAV vector is a virus particle. In accordance with the present invention, the serotype of the virus particle is AAV1, AAV2, AAV3, AAV4, AAV5, AAV6, AAV7, AAV8, AAV9, AAV10, AAV11, or AAV12, or a hybrid serotype thereof.

The pharmaceutical compositions according to the invention can contain any pharmaceutically acceptable excipient. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous. Examples of excipients include but are not limited to starches, sugars, microcrystalline cellulose, diluents, granulating agents, lubricants, binders, disintegrating agents, wetting agents, emulsifiers, coloring agents, release agents, coating agents, sweetening agents, flavoring agents, perfuming agents, preservatives, antioxidants, plasticizers, gelling agents, thickeners, hardeners, setting agents, suspending agents, surfactants, humectants, carriers, stabilizers, and combinations thereof.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal, parenteral or enteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the parenteral route, the compositions may be in the form of solutions or suspensions for infusion or for injection. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Typically, the compositions are administered by injection. Methods for these administrations are known to one skilled in the art.

The pharmaceutical compositions according to the invention can contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins PA, USA) (2000).

Before administration to patients, formulants may be added to the rAAV vector, the cell transfected with the rAAV vector, or the supernatant conditioned with the transfected cell. A liquid formulation may be preferred. For example, these formulants may include oils, polymers, vitamins, carbohydrates, amino acids, salts, buffers, albumin, surfactants, bulking agents or combinations thereof.

Carbohydrate formulants include sugar or sugar alcohols such as monosaccharides, disaccharides, or polysaccharides, or water soluble glucans. The saccharides or glucans can include fructose, dextrose, lactose, glucose, mannose, sorbose, xylose, maltose, sucrose, dextran, pullulan, dextrin, alpha and beta cyclodextrin, soluble starch, hydroxyethyl starch and carboxymethylcellulose, or mixtures thereof. "Sugar alcohol" is defined as a C4 to C8 hydrocarbon having an —OH group and includes galactitol, inositol, mannitol, xylitol, sorbitol, glycerol, and arabitol. These sugars or sugar alcohols mentioned above may be used individually or in combination. There is no fixed limit to amount used as long as the sugar or sugar alcohol is soluble in the aqueous preparation. In one embodiment, the sugar or sugar alcohol concentration is between 1.0 w/v % and 7.0 w/v %, more preferable between 2.0 and 6.0 w/v %.

Amino acids formulants include levorotary (L) forms of carnitine, arginine, and betaine; however, other amino acids may be added.

In some embodiments, polymers as formulants include polyvinylpyrrolidone (PVP) with an average molecular weight between 2,000 and 3,000, or polyethylene glycol (PEG) with an average molecular weight between 3,000 and 5,000.

It is also preferred to use a buffer in the composition to minimize pH changes in the solution before lyophilization or after reconstitution. Most any physiological buffer may be used including but not limited to citrate, phosphate, succinate, and glutamate buffers or mixtures thereof. In some embodiments, the concentration is from 0.01 to 0.3 molar. Surfactants that can be added to the formulation are shown in EP Nos. 270,799 and 268,110.

Another drug delivery system for increasing circulatory half-life is the liposome. Methods of preparing liposome delivery systems are discussed in Gabizon et al., Cancer Research (1982) 42:4734; Cafiso, Biochem Biophys Acta (1981) 649:129; and Szoka, Ann Rev Biophys Eng (1980) 9:467. Other drug delivery systems are known in the art and are described in, e.g., Poznansky et al., DRUG DELIVERY SYSTEMS (R. L. Juliano, ed., Oxford, N.Y. 1980), pp. 253-315; M. L. Poznansky, Pharm Revs (1984) 36:277.

After the liquid pharmaceutical composition is prepared, it may be lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is administered to subjects using those methods that are known to those skilled in the art.

Treatment Methods

In various embodiments, the present invention provides a method of treating, inhibiting, preventing, reducing the severity of and/or reducing the progression of a disease-state in a subject. The method includes providing a composition comprising an rAAV vector comprising a caspase-1 gene or a variant thereof and a Schwann cell specific promoter; and administering a therapeutically effective amount of the composition to the subject, thereby treating, inhibiting, preventing, reducing the severity of and/or reducing the progression of the disease-state in the subject. In various embodiments, the composition may further comprise a chemotherapeutic agent. Examples of chemotherapeutic agents include but are not limited to any one or more of cyclophosphamide, vincristine, imidazole carboxamide, cisplatin, carboplatin, etoposide, gemcitabine, docetaxel, trabectedin, anthracycline, doxorubicin, ifosfamide, cycloxygenase inhibitors, non-steroidal anti-inflammatory agents or combinations thereof.

In accordance with the present invention, the disease-state can be nerve sheath tumor, schwannoma, vestibular schwannoma, sporadic schwannoma, neurofibrosarcoma, neurofibroma, neurofibromatosis (NF), neurofibromatosis type 1 (NF1), neurofibromatosis type 2 (NF2), or schwannomatosis, or a combination thereof. In various embodiments, the subject is a human. In other embodiments, the subject is an animal.

In various embodiments, the composition is administrated to the subject before, during, or after the subject develops the condition. In various embodiments, the composition is administrated to the subject intranervously, intracranially, intratumorally, intramuscularly, intravenously, intradermally, or subcutaneously, or a combination thereof.

In various embodiments, the therapeutically effective amount of the composition comprises about $1\times10^9$-$1\times10^{14}$, $1\times10^9$-$1\times10^{12}$, $1\times10^{10}$-$1\times10^{12}$, $1\times10^{12}$-$1\times10^{14}$, $1\times10^{12}$-$1\times10^{15}$ or $1\times10^{15}$-$1\times10^{18}$ genome copies (gc) of the rAAV vector per kg of body weight of the subject. In various embodiments, the composition is administrated to the subject 1-3 times per day or 1-7 times per week. In various embodiments, the composition is administrated to the subject for 1-5 days, 1-5 weeks, 1-5 months, 1-5 years or throughout the life time of the subject as deemed necessary and would be apparent to a person of skill in the art.

In various embodiments, the method further comprises treating the subject with surgery, radiation therapy, or chemotherapy, or a combination thereof. The surgery, radiation therapy, or chemotherapy, or a combination thereof may be conducted before, during or after administering a therapeutically effective amount of the composition to the subject.

Examples of surgeries include but are not limited to limb sparing surgery, amputation, and plastic surgery. Examples of radiation therapies include but are not limited to stereoatic radiotherapy. In this procedure, a large, precise, external dose of radiation is delivered to the area where the schwannoma is located. It can be given once or over the course of several treatment sessions. Examples of chemotherapeutic agents used for chemotherapy include but are not limited to any one or more of cyclophosphamide, vincristine, imidazole carboxamide, cisplatin, carboplatin, etoposide, gemcitabine, docetaxel, trabectedin, anthracycline, doxorubicin, ifosfamide, cycloxygenase inhibitors, non-steroidal anti-inflammatory agents or combinations thereof.

In various embodiments, the present invention provides a method of treating, inhibiting, preventing, reducing the severity of and/or reducing the progression of a disease-state in a subject. The method includes providing a composition comprising a cell transfected with an rAAV vector comprising a caspase-1 gene or a variant thereof and a Schwann cell specific promoter; and administering a therapeutically effective amount of the composition to the subject, thereby treating, inhibiting, preventing, reducing the severity of and/or reducing the progression of the disease-state in the subject. In various embodiments, the therapeutically effective amount of the composition includes about $10^4$-$10^8$ cells per kg of body weight of the subject. In various embodiments, the composition is administered to the subject 1-3 times per day or 1-7 times per week. In various embodiments, the composition is administered to the subject for 1-5 days, 1-5 weeks, 1-5 months, 1-5 years, or throughout the life time of the subject as deemed necessary and would be apparent to a person of skill in the art. In various embodiments, the method further comprises treating the subject with surgery, radiation therapy, or chemotherapy, or a combination thereof. The surgery, radiation therapy, or chemotherapy, or a combination thereof may be conducted before, during or after administering a therapeutically effective amount of the cell to the subject.

In various embodiments, the present invention provides a method of treating, inhibiting, preventing, reducing the severity of and/or reducing the progression of a disease-state in a subject. The method includes providing a composition comprising a supernatant obtained from a culture of a cell transfected with an rAAV vector comprising a caspase-1 gene or a variant thereof and a Schwann cell specific promoter; and administering a therapeutically effective amount of the composition to the subject, thereby treating, inhibiting, preventing, reducing the severity of and/or reducing the progression of the disease-state in the subject. In various embodiments, the therapeutically effective amount of the composition includes, for example 1 µl to 100 µl, 100 µl to 500 µl, 500 µl to 1 ml, 1 ml to 5 ml, 5 ml to 10 ml or 10 ml to 50 ml or more supernatant per kg of body weight of the subject. In various embodiments, the composition is administered to the subject 1-3 times per day or 1-7 times per week. In various embodiments, the composition is administered to the subject for 1-5 days, 1-5 weeks, 1-5 months, 1-5 years or throughout the life time of the subject as deemed necessary and would be apparent to a person of skill in the art. In various embodiments, the method further comprises treating the subject with surgery, radiation therapy, or chemotherapy, or a combination thereof. The surgery, radiation therapy, or chemotherapy, or a combination thereof may be conducted before, during or after administering a therapeutically effective amount of the supernatant to the subject.

In various embodiments, the present invention provides a method of treating, inhibiting, preventing, reducing the severity of and/or reducing the progression of a disease-state in a subject. The method includes providing a composition comprising an extracellular vesicle isolated from a cell transfected with an rAAV vector comprising a caspase-1 gene or a variant thereof and a promoter; and administering a therapeutically effective amount of the composition to the subject, thereby treating, inhibiting, preventing, reducing the severity of and/or reducing the progression of the disease-state in the subject. In accordance with the present invention, the promoter can be a Schwann cell specific promoter (e.g., a P0 promoter and a PMP22 promoter) or a ubiquitous promoter (e.g., CMV, CBA/CAG, and EF1a promoters). In various embodiments, the composition is administered to the subject 1-3 times per day or 1-7 times per week. In various embodiments, the composition is administered to the subject for 1-5 days, 1-5 weeks, 1-5 months, 1-5 years or throughout the life time of the subject as deemed necessary and would be apparent to a person of skill in the art. In various embodiments, the method further comprises treating the subject with surgery, radiation therapy, or chemotherapy, or a combination thereof. The surgery, radiation therapy, or chemotherapy, or a combination thereof may be conducted before, during or after administering a therapeutically effective amount of the supernatant to the subject.

In various embodiments, in combination with the various treatment methods described above for delivering a caspases-1 gene to a subject, an additional gene (e.g., human Caspase-4, human Caspase-5, mouse Caspase-11, NLRP1, Nlrp3, NRLC4, NALP, AIM2, PYCARD-derived adaptor proteins CARD or ASC, IL-1B and IL-18) may be delivered to the subject by the same rAAV vector, cell, supernatant or extracellular vesicle delivering the caspases-1 gene or a separate vector, cell, supernatant or extracellular vesicle.

Kits

In various embodiments, the present invention provides a kit for treating, inhibiting, preventing, reducing the severity of and/or reducing the progression of a disease-state in a subject. In accordance with the present invention, the disease-state can be nerve sheath tumor, schwannoma, vestibular schwannoma, sporadic schwannoma, neurofibrosarcoma, neurofibroma, neurofibromatosis (NF), neurofibromatosis type 1 (NF1), neurofibromatosis type 2 (NF2), or schwannomatosis, or a combination thereof. In various embodiments, the subject is a human. In other embodiments, the subject is an animal.

In various embodiments, the kit comprises: a composition comprising an rAAV vector comprising a caspase-1 gene or a variant thereof and a Schwann cell specific promoter, or a composition comprising a cell transfected with the rAAV vector, or a composition comprising a supernatant conditioned with the transfected cell, or a composition comprising an extracellular vesicle isolated from the transfected cell; and instructions for using the composition for treating, inhibiting, preventing, reducing the severity of and/or reducing the progression of a disease-state in a subject.

In some embodiments, the kit comprises a rAAV vector comprising a caspase-1 gene or a variant thereof and a Schwann cell specific promoter; and instructions for using the rAAV vector for treating, inhibiting, preventing, reducing the severity of and/or reducing the progression of a disease-state in a subject. In other embodiments, the kit comprises a cell transfected with an rAAV vector comprising a caspase-1 gene or a variant thereof and a Schwann cell specific promoter; and instructions for using the cell for treating, inhibiting, preventing, reducing the severity of and/or reducing the progression of a disease-state in a subject. In still other embodiments, the kit comprises a supernatant obtained from a culture of a cell transfected with an rAAV vector comprising a caspase-1 gene or a variant thereof and a Schwann cell specific promoter; and instructions for using the supernatant for treating, inhibiting, preventing, reducing the severity of and/or reducing the progression of a disease-state in a subject.

In various embodiments, the kit comprises an extracellular vesicle isolated from a cell transfected with an rAAV vector comprising a caspase-1 gene or a variant thereof and a promoter; and instructions for using the extracellular vesicle for treating, inhibiting, preventing, reducing the severity of and/or reducing the progression of a disease-state in a subject. In various embodiments, the kit comprises a composition comprising an extracellular vesicle isolated from a cell transfected with an rAAV vector comprising a caspase-1 gene or a variant thereof and a promoter; and instructions for using the composition for treating, inhibiting, preventing, reducing the severity of and/or reducing the progression of a disease-state in a subject. In accordance with the present invention, the promoter can be a Schwann cell specific promoter (e.g., a P0 promoter and a PMP22 promoter) or a ubiquitous promoter (e.g., CMV, CBA/CAG, and EF1a promoters).

In various embodiments, the kit may further comprise a chemotherapeutic agent and instructions for the use of the chemotherapeutic agent together with the components described above for treating, inhibiting, preventing, reducing the severity of and/or reducing the progression of a disease-state in a subject. Examples of chemotherapeutic agents include but are not limited to any one or more of cyclophosphamide, vincristine, imidazole carboxamide, cisplatin, carboplatin, etoposide, gemcitabine, docetaxel, trabectedin, anthracycline, doxorubicin, ifosfamide, cyclooxygenase inhibitors, non-steroidal anti-inflammatory agents or combinations thereof.

The kit is an assemblage of materials or components, including at least one of the inventive vectors and compositions. Thus, in some embodiments the kit contains a composition including a drug delivery molecule complexed with a therapeutic agent, as described above.

The exact nature of the components configured in the inventive kit depends on its intended purpose. In one embodiment, the kit is configured particularly for human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to treat, reduce the severity of, inhibit or prevent schwannoma in a subject. Still in accordance with the present invention, "instructions for use" may include a tangible expression describing the preparation of virions and/or at least one method parameter, such as the relative amounts of rAAV vector genome, dosage requirements and administration instructions, and the like, typically for an intended purpose. Optionally, the kit also contains other useful components, such as, measuring tools, diluents, buffers, pharmaceutically acceptable carriers, syringes or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. As used herein, the term "package" refers to a suitable solid matrix or material such as glass, plastic, paper, foil, and the like, capable of holding the individual kit components. Thus, for example, a package can be a glass vial used to contain suitable quantities of a composition containing a volume of the AAV1-P0-ICE vector. The packaging material generally has an external label which indicates the contents and/or purpose of the kit and/or its components.

Nerve sheath tumors, the neurofibromatoses, tend to be slow growing, non-malignant neoplasms that lead to persistent pain and to sensory and motor dysfunction. Unfortunately, the current therapy is of limited efficacy and surgical resection, when possible, is often the only option. However, nerve sheath tumors are technically difficult for surgical resection due the location and/or number of tumors, and surgical resection could lead to significant functional impairment. Thus, treatment of nerve sheath tumors as well as other non-malignant tumors of the nervous system represents a major unmet clinical need. The neurofibromatoses—NF1, NF2, and schwannomatosis—together affect approximately 1 in 3000 births. Frequently, these diseases are initially expressed during childhood and the related burden continues throughout life.

This invention provides a novel strategy for treating these tumors: a gene therapy is utilized to deliver a pyroptosis-inducing transgene to tumor cells, and pyroptosis is induced for generating a therapeutic cascade that leads to tumor cell killing and induction of host immune responses capable of killing distal and subsequently arising tumors. Pyroptosis refers to a biological intracellular cascade that results in cell death and release of biological mediators that induce host immune responses, both innate and adaptive. These secondary host immune responses have the capacity to kill remaining local and distant tumor cells and to establish a vaccine effect.

The treatment based on gene therapy induced pyroptosis is especially applicable to benign tumors of the nervous system (e.g., nerve sheath tumors), which are not suitable for surgical resection due to the location and/or number of tumors, can develop in multiple locations over time, and are otherwise currently untreatable. This approach, however, may also be applicable to non-neural benign tumors, as well as, malignant neoplasms.

Further embodiments of the present invention include the following numbered paragraphs:

1. A recombinant adeno-associated virus (rAAV) vector comprising a caspase-1 gene or a variant thereof and a Schwann cell specific promoter.

2. The rAAV vector of paragraph 1, wherein the caspase-1 gene is a human, mouse, or rat caspase-1 gene.

3. The rAAV vector of paragraph 1, wherein the Schwann cell specific promoter comprises a P0 promoter or a peripheral myelin protein 22 (PMP22) promoter.

4. The rAAV vector of paragraph 1, wherein the Schwann cell specific promoter is upstream of the caspase-1 gene or the variant thereof.

5. The rAAV vector of paragraph 1, further comprising a polyadenylation signal.

6. The rAAV vector of paragraph 5, wherein the polyadenylation signal is downstream of the caspase-1 gene or the variant thereof.

7. The rAAV vector of paragraph 5, wherein the polyadenylation signal comprises a bovine growth hormone polyadenylation signal (BGHpA), a SV40 polyadenylation signal or a rabbit beta-globin polyadenylation signal.

8. The rAAV vector of paragraph 1, comprising a sequence as set forth in SEQ ID NO.: 4 or a variant thereof.

9. The rAAV vector of paragraph 1, comprising a sequence as set forth in SEQ ID NO.: 5 or a variant thereof.

10. The rAAV vector of paragraph 1, comprising a sequence as set forth in SEQ ID NO.: 6 or a variant thereof.

11. The rAAV vector of paragraph 1, comprising a sequence as set forth in SEQ ID NO.: 7 or a variant thereof.

12. The rAAV vector of paragraph 1, wherein the rAAV vector is a polynucleotide.

13. The rAAV vector of paragraph 1, wherein the rAAV vector is a single-stranded or double-stranded AAV.

14. The rAAV vector of paragraph 1, wherein the rAAV vector is a self-complementary AAV (scAAV).

15. The rAAV vector of paragraph 5, further comprising a first AAV inverted terminal repeat (ITR) located upstream of the Schwann cell specific promoter and a second AAV ITR located downstream of the polyadenylation signal.

16. The rAAV vector of paragraph 15, wherein the first or second AAV inverted terminal repeat comprises a deletion of the terminal resolution site.

17. The rAAV vector of paragraph 1, wherein the rAAV vector is a virus particle.

18. The rAAV vector of paragraph 17, wherein the serotype of the virus particle is AAV1, AAV2, AAV3, AAV4, AAV5, AAV6, AAV7, AAV8, AAV9, AAV10, AAV11, or AAV12, or a hybrid serotype thereof.

19. A method of treating, inhibiting, preventing, reducing the severity of and/or reducing the progression of a disease-state in a subject, comprising:
providing a composition comprising an rAAV vector comprising a caspase-1 gene or a variant thereof and a Schwann cell specific promoter; and
administering a therapeutically effective amount of the composition to the subject, thereby treating, inhibiting, preventing, reducing the severity of and/or reducing the progression of the disease-state in the subject.

20. The method of paragraph 19, wherein the disease-state is nerve sheath tumor, schwannoma, vestibular schwannoma, sporadic schwannoma, neurofibrosarcoma, neurofibroma, neurofibromatosis (NF), neurofibromatosis type 1 (NF1), neurofibromatosis type 2 (NF2), or schwannomatosis, or a combination thereof.

21. The method of paragraph 19, wherein the subject is a human or animal.

22. The method of paragraph 19, wherein the composition is administered to the subject before, during, or after the subject develops the condition.

23. The method of paragraph 19, wherein the composition is administered to the subject intranervously, intracranially, intratumorally, intramuscularly, intravenously, intradermally, or subcutaneously, or a combination thereof.

24. The method of paragraph 19, wherein the therapeutically effective amount of the composition comprises about $1 \times 10^9$-$1 \times 10^{14}$ genome copies (gc) of the rAAV vector per kg of body weight of the subject.

25. The method of paragraph 19, wherein the composition is administered to the subject 1-3 times per day or 1-7 times per week.

26. The method of paragraph 19, wherein the composition is administered to the subject for 1-5 days, 1-5 weeks, 1-5 months, 1-5 years or throughout the subject's lifetime.

27. The method of paragraph 19, further comprising treating the subject with surgery, radiation therapy, or chemotherapy, or a combination thereof.

28. The method of paragraph 19, wherein the composition further comprises a chemotherapeutic agent.

29. A pharmaceutical composition comprising:
an rAAV vector comprising a caspase-1 gene or a variant thereof and a Schwann cell specific promoter; and
a pharmaceutically acceptable carrier.

30. The pharmaceutical composition of paragraph 29, further comprising a chemotherapeutic agent.

31. The pharmaceutical composition of paragraph 29, wherein the caspase-1 gene is a human, mouse, or rat caspase-1 gene.

32. The pharmaceutical composition of paragraph 29, wherein the concentration of the rAAV vector is about $1 \times 10^7$-$1 \times 10^{12}$ gc per μl of the pharmaceutical composition.

33. The pharmaceutical composition of paragraph 29, wherein the Schwann cell specific promoter comprises a P0 promoter or a peripheral myelin protein 22 (PMP22) promoter.

34. The pharmaceutical composition of paragraph 29, wherein the Schwann cell specific promoter is upstream of the caspase-1 gene or the variant thereof.

35. The pharmaceutical composition of paragraph 29, wherein the vector further comprises a polyadenylation signal.

36. The pharmaceutical composition of paragraph 35, wherein the polyadenylations signal is downstream of the caspase-1 gene or the variant thereof.

37. The pharmaceutical composition of paragraph 35, wherein the polyadenylation signal comprises a bovine growth hormone polyadenylation signal, a SV40 polyadenylation signal or a rabbit beta-globin polyadenylation signal.

38. The pharmaceutical composition of paragraph 29, wherein the rAAV vector comprises a sequence as set forth in SEQ ID NO.: 4 or a variant thereof.

39. The pharmaceutical composition of paragraph 29, wherein the rAAV vector comprises a sequence as set forth in SEQ ID NO.: 5 or a variant thereof.

40. The pharmaceutical composition of paragraph 29, wherein the rAAV vector comprises a sequence as set forth in SEQ ID NO.: 6 or a variant thereof.

41. The pharmaceutical composition of paragraph 29, wherein the rAAV vector comprises a sequence as set forth in SEQ ID NO.: 7 or a variant thereof.

42. The pharmaceutical composition of paragraph 29, wherein the rAAV vector is a single-stranded or double-stranded AAV.

43. The pharmaceutical composition of paragraph 29, wherein the rAAV vector is a self-complementary AAV (scAAV).

44. The pharmaceutical composition of paragraph 35, further comprising a first AAV inverted terminal repeat (ITR) located upstream of the Schwann cell specific promoter and a second AAV ITR located downstream of the polyadenylation signal.

45. The pharmaceutical composition of paragraph 44, wherein the first or second AAV inverted terminal repeat comprises a deletion of the terminal resolution site.

46. The pharmaceutical composition of paragraph 29, wherein the rAAV vector is a virus particle.

47. The pharmaceutical composition of paragraph 46, wherein the serotype of the virus particle is AAV1, AAV2, AAV3, AAV4, AAV5, AAV6, AAV7, AAV8, AAV9, AAV10, AAV11, or AAV12, or a hybrid serotype thereof.

48. A kit comprising:
an rAAV vector comprising a caspase-1 gene or a variant thereof and a Schwann cell specific promoter; and
instructions for using the rAAV vector treating, inhibiting, preventing, reducing the severity of and/or reducing the progression of a disease-state in a subject.

49. A kit comprising:
a composition comprising an rAAV vector comprising a caspase-1 gene or a variant thereof and a Schwann cell specific promoter; and
instructions for using the composition for treating, inhibiting, preventing, reducing the severity of and/or reducing the progression of a disease-state in a subject.

50. A cell transfected with an rAAV vector comprising a caspase-1 gene or a variant thereof and a Schwann cell specific promoter.

51. The cell of paragraph 50, wherein the cell is a schwannoma cell or a Schwann cell.

52. A method of treating, inhibiting, preventing, reducing the severity of and/or reducing the progression of a disease-state in a subject, comprising:

providing a composition comprising a cell transfected with an rAAV vector comprising a caspase-1 gene or a variant thereof and a Schwann cell specific promoter; and administering a therapeutically effective amount of the composition to the subject, thereby treating, inhibiting, preventing, reducing the severity of and/or reducing the progression of the disease-state in the subject.

53. The method of 52, wherein the therapeutically effective amount of the composition comprises $10^4$-$10^8$ transfected cells per kg of body weight of the subject.

54. The method of 52, wherein the composition is administrated to the subject 1-3 times per day or 1-7 times per week.

55. The method of 52, wherein the composition is administrated to the subject for 1-5 days, 1-5 weeks, 1-5 months, 1-5 years or throughout the subject's lifetime.

56. A kit comprising:

a composition comprising a cell transfected with an rAAV vector comprising a caspase-1 gene or a variant thereof and a Schwann cell specific promoter; and instructions for using the composition for treating, inhibiting, preventing, reducing the severity of and/or reducing the progression of a disease-state in a subject.

57. A supernatant obtained from a culture of a cell transfected with an rAAV vector comprising a caspase-1 gene or a variant thereof and a Schwann cell specific promoter.

58. The supernatant of paragraph 57, wherein the cell is a schwannoma cell or a Schwann cell.

59. The supernatant of paragraph 57, wherein the transfected cell is cultured for about 12-24, 24-48, or 48-73 hours.

60. The supernatant of paragraph 57, wherein the supernatant comprises extracellular vesicles released from the transfected cell.

61. A method of treating, inhibiting, preventing, reducing the severity of and/or reducing the progression of a disease-state in a subject, comprising:

providing a composition comprising a supernatant obtained from a culture of a cell transfected with an rAAV vector comprising a caspase-1 gene or a variant thereof and a Schwann cell specific promoter; and administering a therapeutically effective amount of the composition to the subject, thereby treating, inhibiting, preventing, reducing the severity of and/or reducing the progression of the disease-state in the subject.

62. The method of 61, wherein the therapeutically effective amount of the composition comprises about 1 μl to 1000 μl supernatant per kg of body weight of the subject.

63. The method of 61, wherein the composition is administrated to the subject 1-3 times per day or 1-7 times per week.

64. The method of 61, wherein the composition is administrated to the subject for 1-5 days, 1-5 weeks, 1-5 months, 1-5 years or throughout the lifetime of the subject.

65. A kit comprising:

a composition comprising a supernatant obtained from a culture of a cell transfected with an rAAV vector comprising a caspase-1 gene or a variant thereof and a Schwann cell specific promoter; and instructions for using the composition for treating, inhibiting, preventing, reducing the severity of and/or reducing the progression of a disease-state in a subject.

66. An extracellular vesicle isolated from a cell transfected with an rAAV vector comprising a caspase-1 gene or a variant thereof and a promoter.

67. The extracellular vesicle of paragraph 66, wherein the promoter is a Schwann cell specific promoter or a ubiquitous promoter.

68. The extracellular vesicle of paragraph 66, wherein the cell is a schwannoma cell or a Schwann cell.

69. The extracellular vesicle of paragraph 66, wherein the transfected cell is cultured for about 12-24, 24-48, or 48-73 hours.

70. A method of treating, inhibiting, preventing, reducing the severity of and/or reducing the progression of a disease-state in a subject, comprising:

providing a composition comprising an extracellular vesicle isolated from a cell transfected with an rAAV vector comprising a caspase-1 gene or a variant thereof and a promoter; and administering a therapeutically effective amount of the composition to the subject, thereby treating, inhibiting, preventing, reducing the severity of and/or reducing the progression of the disease-state in the subject.

71. The method of 61, wherein the composition is administrated to the subject 1-3 times per day or 1-7 times per week.

72. The method of 70, wherein the composition is administrated to the subject for 1-5 days, 1-5 weeks, 1-5 months, 1-5 years or throughout the lifetime of the subject.

73. A kit comprising:

a composition comprising an extracellular vesicle isolated from a cell transfected with an rAAV vector comprising a caspase-1 gene or a variant thereof and a promoter; and instructions for using the composition for treating, inhibiting, preventing, reducing the severity of and/or reducing the progression of a disease-state in a subject.

EXAMPLES

The following examples are not intended to limit the scope of the claims to the invention, but are rather intended to be exemplary of certain embodiments. Any variations in the exemplified methods which occur to the skilled artisan are intended to fall within the scope of the present invention.

Example 1

Experimental Materials and Methods

Cell Culture

The HEI-193 human schwannoma cell line was established from a schwannoma in a patient with NF2, immortalized with human papillomavirus E6/E7 genes (Hung et al., 2002) and maintained in Dulbecco's modified Eagle's medium (DMEM) with 2 μM forskolin (Calbiochem, San Diego, Calif.), recombinant glial growth factor (14 ng/ml; Sigma-Aldrich, St. Louis, Mo.), and G418 disulfate salt (50 μg/ml; Sigma-Aldrich). To obtain the HEI-193FC cell line, HEI-193 cells were infected with lentivirus encoding Fluc and mCherry (Prabhakar et al., 2010). Human neuroblastoma cell line SH-SY5Y (American Type Culture Collection [ATCC], Manassas, Va.) was grown in DMEM-F12 (1:1) (GIBCO-BRL, Rockville, Md.). HEK-293T human embryonic kidney cells (from M. Calos, Stanford University, Stanford, Calif.) were grown in DMEM. For all cell types, growth media were supplemented with 10% fetal bovine serum (FBS; Sigma-Aldrich) and 1% penicillin-streptomycin (Cellgro, Herndon, Va.) and cells were maintained at 37° C. in a humidified atmosphere of 5% CO2 and 95% air.

AAV Vector Design and Packaging

AAV vector plasmids dsAAV-P0-ICE and dsAAV-P0-GFP were derived from the plasmid dsAAV-CBA-GFP-BGHpA (Sena-Esteves laboratory). This plasmid carries two AAV2 inverted terminal repeat (ITR) elements, one wild type and one in which the terminal resolution site was deleted, as described (McCarty et al., 2003), generating a vector that is packaged as a double-stranded molecule. The dsAAV-P0-ICE plasmid was generated by replacing the CBA-GFP cassette in the parent plasmid with the PCR-amplified rat P0 promoter (1.1 kb; for full details of the P0 promoter see Brown and Lemke, 1997) and cDNA, using the plasmid HSV-P0-ICE (Prabhakar et al., 2010) as a template and the following primers: P0-1 (SEQ ID NO.:12), AAAGGTAC Cacgagcattctcgaactctccaaa; P0-2 (SEQ ID NO.: 13), AAAACTAGTtctgcagaattcg atatcaagcttgg; mCaspase-1.1 (SEQ ID NO.: 14), aaaactagtgccaccatggctgtgagggc aaagaggaaG; mCaspase-1.2 (SEQ ID NO.: 15), AAAGCG-GCCGCttaatgtcccggg aagaggtagAAA. The dsAAV-P0-GFP plasmid was generated by replacing the chicken β-actin (CBA) promoter in the parent plasmid with the PCR-amplified rat P0 promoter. Both AAV vectors carry the bovine growth hormone polyadenylation signal. The identity of all PCR-amplified sequences was confirmed by sequencing.

AAV1 serotype vectors were produced by transient co-transfection of 293T cells by calcium phosphate precipitation of vector plasmid (dsAAV-P0-ICE or dsAAV-P0-GFP), adenoviral helper plasmid pFD6, and a plasmid encoding the AAV1 cap gene (pXR1), as previously described (Broekman et al., 2006). Briefly, AAV vectors were purified by iodixanol gradient centrifugation followed by column chromatography with HiTrap Q anion-exchange columns (GE Healthcare, Piscataway, N.J.). The virus-containing fractions were concentrated with Centricon 100-10a molecular weight cutoff (MWCO) centrifugal devices (Millipore, Billerica, Mass.) and the titer (genome copies [GC]/ml) was determined by real-time PCR amplification with primers and probe specific for the bovine growth hormone polyadenylation signal.

Luminescence Cell Viability Assay

The CellTiter-Glo luminescent cell viability assay (Promega, Madison, Wis.) was used to determine the number of viable cells in culture on the basis of quantitation of ATP levels, an indicator of metabolically active cells. The system detects as few as 15 cells per well 10 min after adding reagent and mixing, resulting in cell lysis and the generation of a luminescent signal proportional to the amount of ATP present. Ten thousand HEI-193, 293T, or SH-SY5Y cells were plated into the wells of 96-well plates and infected in triplicate with the AAV1-P0-ICE or AAV1-P0-GFP vector at a multiplicity of infection (MOI) of 10,000 GC/cell to achieve >90% infection. After 72 hr, medium was aspirated off and cells were incubated in 100 μl of fresh medium containing 25 μl of CellTiter-Glo reagent for 10 min at room temperature. The luminescence was measured with a luminometer (Dynex Technologies, Chantilly, Va.).

Animals

All animal experimentation was approved by and conducted under the oversight of the Massachusetts General Hospital (Boston, Mass.) Institutional Animal Care and Use Committee. Animals, nu/nu and C57BL/6 mice, were kept on a 12:12 light-to-dark cycle with ad libitum access to food and water. Animals were checked daily to evaluate health.

Generation of Tumors and Vector Injection

Figure 7:
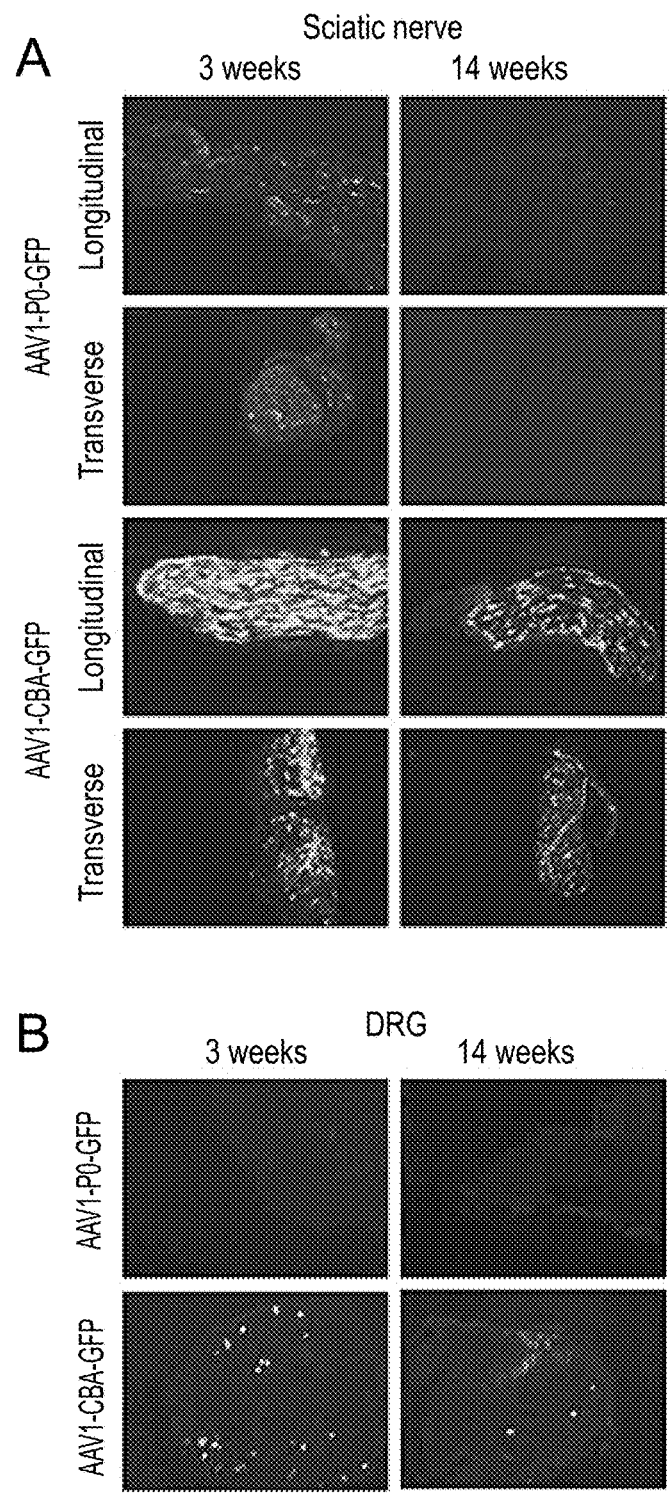
FIG. 7 depicts in accordance with various embodiments of the invention the GFP expression after injection of AAV1-P0-GFP or AAV1-CBA-GFP into the sciatic nerve of young (postnatal day 21 [P21]) and adult (14 week) C57BL/6 mice. Naive sciatic nerves of immune-competent (C57BL/6) mice (n=3/age group/vector, 12 total) were injected with AAV1-P0-GFP or AAV1-CBA-GFP vector ($10^{13}$ GC in 1 μl) in P21 and 14-week-old mice. After 10 days, the (A) sciatic nerves (both longitudinal and transverse sections shown) and (B) dorsal root ganglia (DRG) were collected, frozen serial sections were obtained, and GFP immunofluorescence was determined. Representative images are shown. Original magnification: ×10.

Sciatic nerve schwannomas were generated by direct injection of schwannoma cells into the left sciatic nerve of isoflurane-anesthetized mice, as described (Saydam et al., 2011). Specifically, cells were implanted approximately 4 mm distal to the sciatic notch at a point midway between the sciatic notch and the trifurcation of the sciatic nerve into the common peroneal, tibial, and sural branches. For all experiments other than the experiment shown in FIG. 7, HEI-193FC cells were trypsinized and rinsed, and 30,000 cells in a volume of 1 μl of culture medium were injected into the distal sciatic nerve of athymic nude mice (nu/nu, 5-week-old females; National Cancer Institute [NCI]), using a glass micropipette and a gas-powered microinjector (IM-300; Narishige, Tokyo, Japan). For the data shown in FIG. 7, a similar implantation procedure was performed, differing only in that cells (60,000 in 1 μl) were implanted more proximally in the sciatic nerve. Tumor growth was monitored by in vivo bioluminescence imaging at weekly intervals, using the CMIR Image program (an image display and analysis suite developed in the Interactive Data Language [IDL; Research Systems/Exelis Visual Information Solutions, Boulder, Colo.]) as described (Prabhakar et al., 2010). Briefly, mice were injected intraperitoneally with the Fluc substrate D-luciferin, and, 5 min later, signal was acquired with a high-efficiency IVIS Spectrum (Caliper Life Sciences, Hopkinton, Mass.) with an XGI-8 gas anesthesia system (Caliper Life Sciences) for FIG. 3A and a cryogenically cooled, high-efficiency charge-coupled device (CCD) camera system (Roper Scientific, Trenton, N.J.) for FIG. 3B.

After 4 weeks, tumors that grew progressively were treated with AAV1-P0-ICE or AAV1-P0-GFP. The schwannomas were injected twice, 1 week apart, with $10^{10}$ vector GC in 1 using either AAV1-P0-ICE or AAV1-P0-GFP (over approximately 10 sec), under direct visualization as described for injection of tumor cells (Saydam et al., 2011), targeting the enlarged part of the nerve where tumor cells were implanted. Volumetric changes in tumors were tracked by in vivo bioluminescence imaging out to 18-19 weeks.

Histology

After treatment with vectors, the animals were killed with isoflurane (3%) followed by decapitation. Sciatic nerves were taken out and fixed in 10% formalin for hematoxylin and eosin (H&E) staining (Messerli et al., 2002). The sciatic nerve was removed; one-third of each of these biopsies was fixed in glutaraldehyde for Epon embedding, one-third was fixed in 10% buffered formalin for paraffin embedding, and the remaining third was fresh-frozen at −80° C. for PCR analysis of biodistribution of vector. Myelin integrity of sciatic nerves injected with AAV1-P0-ICE vector was assessed in toluidine blue-stained ultrathin sections prepared as follows: nerves were placed into a modified Karnovsky fixative (2.5% glutaraldehyde, 2.0% paraformaldehyde, and 0.025 calcium chloride in 0.1 M sodium cacodylate buffer), pH 7.4, and fixed overnight at 4° C. Further processing was done with a Leica Lynx automatic tissue processor. Briefly, the nerves were post-fixed in aqueous 1.3% osmium tetroxide, dehydrated in graded ethanol solutions, en bloc stained with 3.0% uranyl acetate in the 70% ethanol step, infiltrated with epoxy and propylene oxide mixtures, and embedded in pure epoxy. The nerves were flat embedded (to maintain orientation) and allowed to polymerize overnight at 60° C. One-micron sections were cut with a DuPont-Sorvall MT-1 ultramicrotome and glass knives. The sections were then stained on a warm hotplate with a solution of 0.5% toluidine blue in 0.5% sodium borate, rinsed with water, dried, and coverslipped (Eichler et al., 2009). The formalin-fixed tissue was processed and embedded in paraffin. Sections were stained with H&E in accordance with routine protocols.

Behavioral Analysis

The mice were tested by the von Frey method for pain/mechanical sensitivity and by rotarod for gross motor function according to published methods (Agarwal et al., 2007; Kirschbaum et al., 2009). Both nu/nu and C57BL/6 mice were used for the behavioral experiments. One microliter ($10^{13}$ GC/ml) of the vector AAV1-P0-ICE, 1 µl of AAV1-P0-GFP, or 1 µl of phosphate-buffered saline (PBS) was injected into the sciatic nerve twice, with injections spaced 1 week apart (n=12 per group). All animals were allowed to habituate to the behavioral apparatus for 1 week before testing for baseline. Three baseline measurements on three separate days preceded the first injection. Mice were then tested the day after each injection and twice per week for 8 weeks.

Mechanical sensitivity of the hind paw was measured by determining withdrawal thresholds assessed with von Frey filaments employed to determine mechanical sensitivity of the plantar surface of both hind paws (only data for the hind paw ipsilateral to the experimental schwannoma is shown). A set of 20 von Frey filaments (North Coast Medical, Gilroy, Calif.), generating bending forces ranging from 0.008 to 300 grams, were used. Mice were "rested" in the test cages for 30 min before establishment of withdrawal threshold. All tests were performed on the right (control) and left (injected) hind paws. The middle plantar surface of the paw was stimulated with a series of ascending force von Frey monofilaments. The 50% threshold for each paw withdrawal was calculated, as previously described (Chen et al., 2009).

A rotating rod apparatus (Columbus Instruments, Columbus, Ohio) was used to assess motor performance.

Mice were placed on the elevated accelerating rod beginning at 1 rpm/min for two trials per day twice per week. Each trial lasted 3 min, during which time the rotating rod underwent a linear acceleration from 1 to 40 rpm. Animals were scored for their latency (in seconds) to fall in each trial and the average of two trials is reported. Animals rested a minimum of 10 min between trials to avoid fatigue (Chen et al., 2009).

Data Analysis

All data are presented as group averages±SEM. The baseline value for all tests before injection used the average of all measurements before injection. Data were analyzed with SPSS 19 (IBM, Armonk, N.Y.). Repeated-measure analysis of variance (ANOVA) was used when data were collected in multiple trials (Harris et al., 2012). $p<0.05$ was accepted as significant.

Genomic DNA Extraction and Real-Time PCR: Biodistribution

At necropsy, tissues were harvested, snap frozen in liquid nitrogen, and stored at −80° C. until genomic DNA was extracted. Genomic DNA (gDNA) was isolated from the spinal cord, ipsilateral and contralateral dorsal root ganglia (DRG), and ipsilateral and contralateral sciatic nerves, using a DNeasy blood and tissue kit (Qiagen, Valencia, Calif.) according to the manufacturer's instructions. gDNA concentrations were determined with a biophotometer (Eppendorf, Hamburg, Germany). AAV GCs in the gDNA were quantified by real-time PCR with an ABI 7900 HT sequence detection system (Applied Biosystems, Foster City, Calif.), according to the manufacturer's instructions, and results were analyzed with the SDS 2.3 software. Briefly, primer pairs and probe were designed to the bovine growth hormone (BGH) poly(A) region of the scAAV1-P0-GFP vector, using ABI Primer Express software version 2.0. A standard curve was created, using scAAV1-P0-GFP plasmid DNA containing the BGH poly(A) region. The PCRs contained a total volume of 100 µl and were run under the following conditions: 50° C. for 2 min, 95° C. for 10 min, and 45 cycles of 95° C. for 15 sec and 60° C. for 1 min.

DNA samples were assayed in triplicate. To control for false negatives due to endogenous tissue-related PCR inhibition, the third replicate was spiked with plasmid DNA at a ratio of 100 copies/µg gDNA. If this replicate was greater than 40 copies/µg gDNA then the results were considered acceptable. If a sample contained ~100 copies/µg gDNA it was considered positive for vector genomes. If a sample contained fewer than 100 copies/µg gDNA it was considered negative for vector genomes. If less than 1 µs of gDNA was analyzed, the vector copy number reported was normalized per microgram of gDNA and the plasmid spike-in was reduced to maintain the ratio of 100 copies/µg gDNA.

Example 2

Effects of Delivery of AAV1-P0-ICE Vectors to Schwannomas

We have developed two mouse models which are relevant to clinical schwannomas. In one model, immortalized human schwannoma cells from an NF2 patient stably transduced with firefly luciferase (Fluc) and mCherry, termed HEI-193FC (Prabhakar et al., 2010) are injected into the sciatic nerve of nu/nu mice where they form tumors (typically in 80% of implanted animals). These tumors grow at reproducible rates as monitored by in vivo bioluminescence imaging with correlative histopathology (FIG. 1A).

In prior studies we generated and characterized a mouse schwannoma line, NFS2-1 (Prabhakar et al., Cancer Gene Therapy, 2007). We have now shown that these cells form a tumor when implanted in the sciatic nerve of the mouse strain of origin (FIG. 1B), thus, providing us with a syngeneic mouse model to assess potential inflammatory and immune responses to this therapy.

Figure 2:
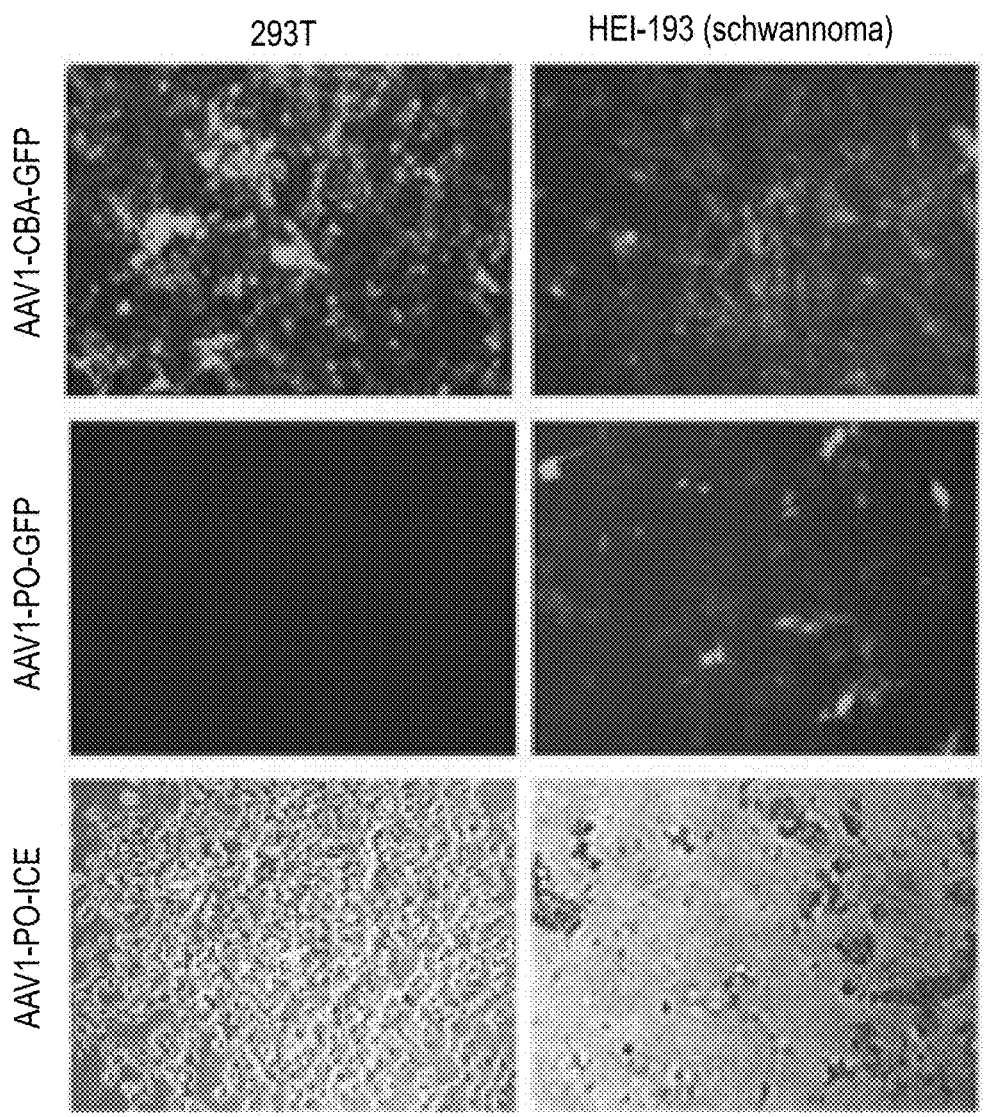
FIG. 2 depicts in accordance with various embodiment of the invention, that the P0 promoter is selectively expressed in schwannoma cells and P0-ICE constructs selectively kill schwannoma cells. (A) 293T cells and HEI-193 schwannoma cells were infected with AAV1-CBA-GFP, AAV1-P0-GFP, or AAV1-P0-ICE vector in culture at a multiplicity of infection (MOI) of 10,000 GC/cell and, after 48 hr, were evaluated microscopically for GFP fluorescence and cell morphology at an original magnification of ×10. (B) Cell viability was assessed by Fluc bioluminescence in 293T, SH-SY5Y (neuroblastoma), and HEI-193 cells 72 hr after infection with AAV1-P0-ICE or AAV1-P0-GFP, or no infection, at the same MOI as in (A). Values for each cell line are normalized to viability of uninfected cells. *Significant difference compared with the control group (p=0.00006). (C) P0-ICE constructs selectively kill schwannoma cells. Human 293T fi broblastic, human SH-SY5Y neuroblastoma, human HEI-193FC schwannoma and mouse NF2S-1 schwannoma cells were transfected with AAV-P0-hICE, AAV-P0-mICE, or AAV-P0-GFP, or non-transfected. After 72 hr, cell viability was assessed by bioluminescence. AAV-P0-ICE vectors killed schwannomas compared to GFP or untransfected controls (*$p<0.001$; **$p<0.003$).
Figure 2:
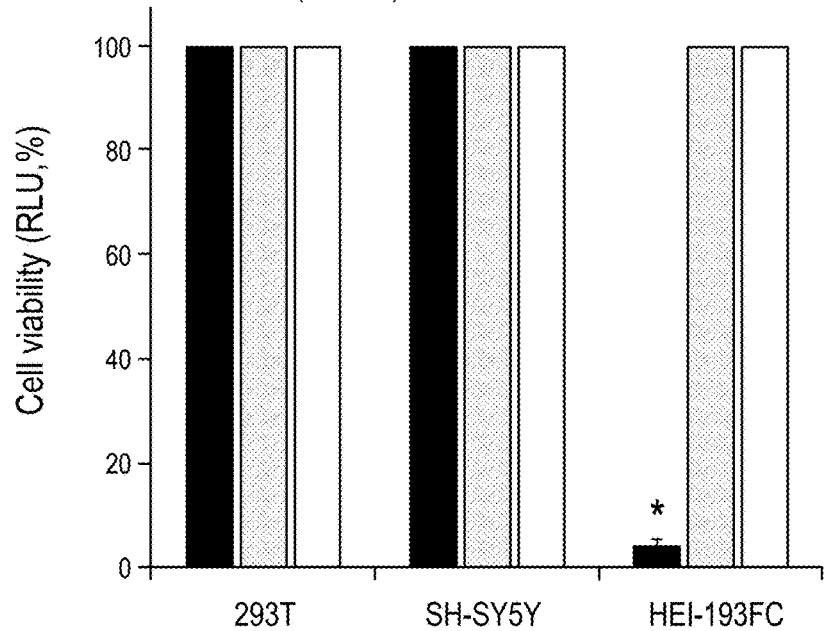
Figure 2:
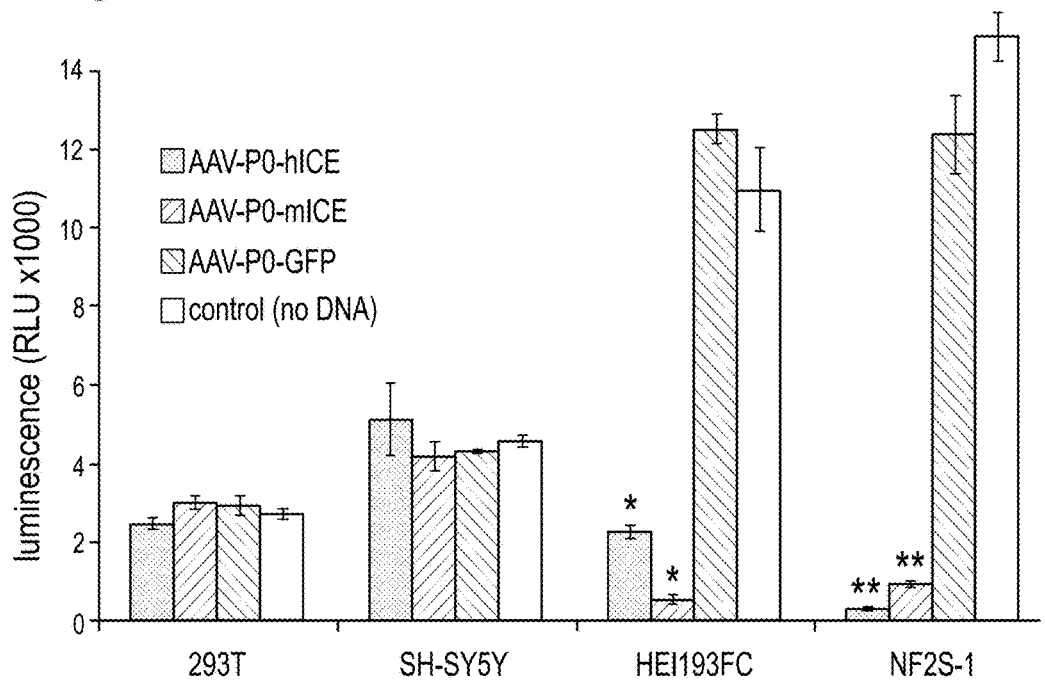
Figure 14:
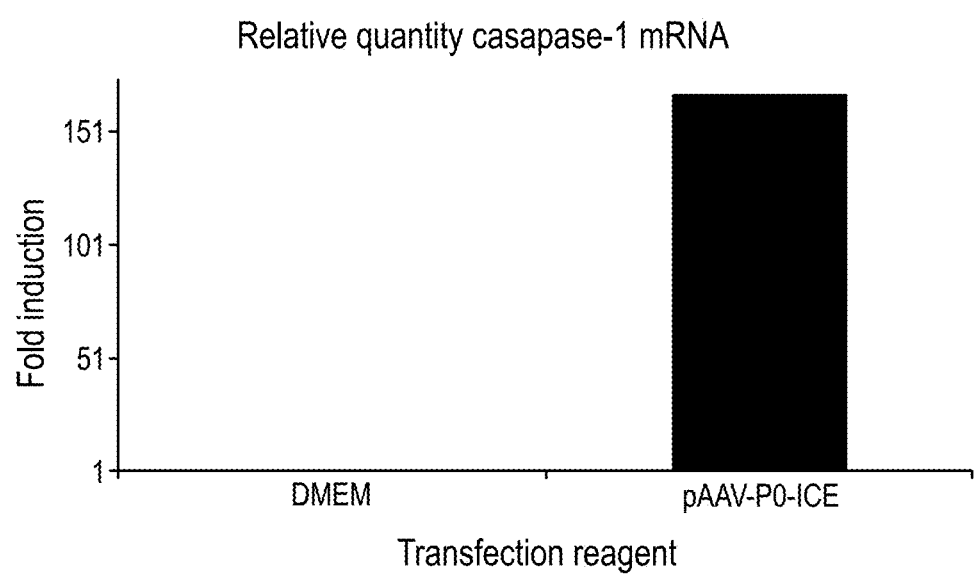
FIG. 14 depicts in accordance with various embodiments of the invention the induction of capase-1 mRNA.

To assess the ability of AAV1 vectors to kill schwannoma cells, we generated AAV1 vectors encoding ICE (Juan et al., 1996) or GFP under the control of the rat P0 promoter (shown for AAV1-P0-ICE in FIG. 1C). In initial evaluation, AAV1-CBA-GFP, AAV1-P0-GFP, and AAV1-P0-ICE vectors were used to infect human 293T cells and schwannoma HEI-193 cells. Using the constitutive promoter, CBA, both cell types showed a high degree of infectivity, that is, GFP-positive cells (FIG. 2A). When the P0 promoter (Brown and Lemke, 1997) was used, expression of GFP was seen only in HEI-193 cells, and not in 293T cells. Cell viability after infection with AAV1-P0-ICE and AAV1-P0-GFP vectors (or no vector) was assessed by CellTiter-Glo assay in 293T, human neuroblastoma SH-SY5Y, and HEI-193 cells. Infection with the AAV1-P0-ICE vector did not lead to any death of 293T or SH-SY5Y cells, whereas more than 90% of HEI-193 cells were dead by 72 hr postinfection (FIG. 2B). As an added control, we used TaqMan real-time RT-PCR to evaluate induction of the caspase-1 transgene after in vitro transduction of cultured HEI-193 cells with pAAV-P0-ICE. There was a 161-fold induction of caspase-1 mRNA (FIG. 14).

We have demonstrated that expression of mouse and human ICE (mICE and hICE, respectively) under the P0 promoter are selectively toxic to schwannoma cells in culture, as compared to other cell types (FIG. 2C). While both human schwannoma line HEI-193 and mouse schwannoma line NF2S-1 showed over 80% death within 72 hr after transfection with the vector construct, the viability of human fibroblastic line, 293T and human neuroblastoma line, SH-SY5Y was not significantly affected, with parallel transfection with a GFP plasmid under a strong ubiquitous CBA promoter showing equivalent transfection efficiencies among lines.

Example 3

AAV1-P0-ICE Causes Regression of HEI-193FC Schwannomas

The therapeutic efficacy of the AAV1-P0-ICE vector was tested in a mouse model in which schwannomas are generated via implantation of HEI-193FC cells in the distal region of the sciatic nerve of nude mice. Vector injections were carried out according to two paradigms early in tumor growth and after establishment of schwannomas. The AAV1-P0-GFP vector was used for the control group. Two intratumoral injections of the AAV1-P0-ICE or AAV1-P0-GFP vector ($10^{10}$ GC in 1 µl), spaced 1 week apart, at the site of early HEI-193FC tumor formation prevented further growth as assessed by in vivo bioluminescence imaging over a 14-week period after vector injections (FIG. 3A); one-way ANOVA revealing a significant effect of AAV1-P0-ICE treatment [$F(1,11)=6.04$, $p=0.03$]. In contrast, the majority of tumors (five of six) injected with the AAV1-P0-GFP vector continued to grow for the 9 weeks of post-injection evaluation. When intratumoral injections of AAV1-P0-ICE were carried out in larger, more established HEI-193FC tumors, AAV1-P0-ICE injections caused essentially complete regression of these tumors out to 12 weeks after vector injections [FIG. 3B; ANOVA: $F(1,16)=8.27$, $p=0.01$], whereas most of the AAV1-P0-GFP-injected tumors (five of six) continued to grow. In both panels of FIGS. 3A and B the relatively large SEM in the AAV1-P0-GFP control group reflects the spontaneous tumor regression in one of six animals in each group. To avoid bias in our data, we used an intention-to-treat approach that included data from all vector-injected animals for statistical analysis.

Figure 3:
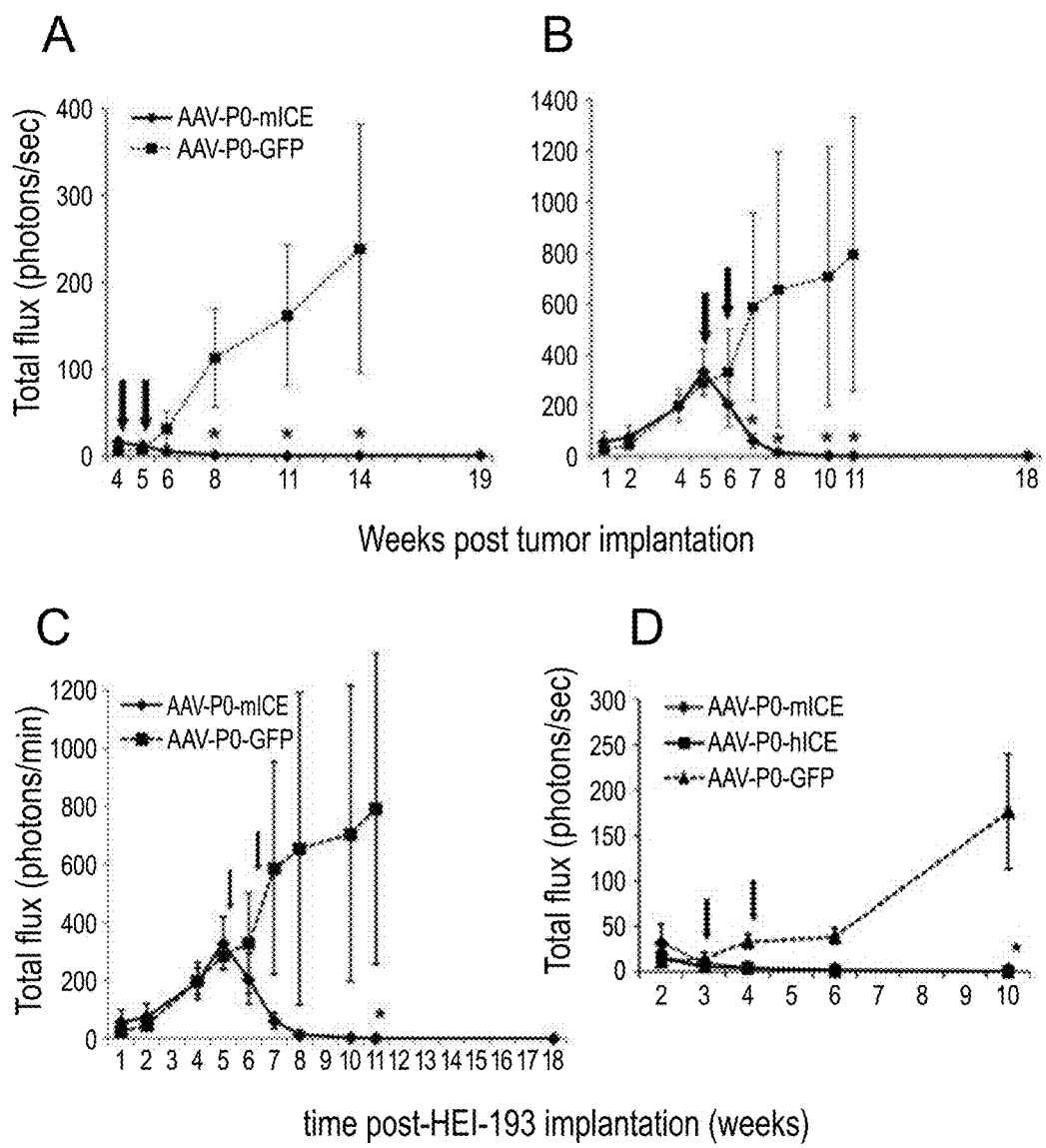
FIG. 3 depicts in an accordance with various embodiment of the invention the monitoring of schwannoma volumes in vivo by bioluminescence imaging. Thirty thousand HEI-193FC cells were implanted into the distal sciatic nerve of nude mice and tumor volume was monitored at weekly intervals by in vivo bioluminescence imaging. At the time points indicated [arrows; weeks 4 and 5 (A) and weeks 5 and 6 (B)] after tumors were established, they were injected twice (i.e., two separate injections 1 week apart) with either AAV1-P0-ICE or AAV1-P0-GFP vector ($1\times10^{10}$ GC in 1 ll per injection). Graphs in (A) and (B) were obtained with different bioluminescence imaging systems, and thus the luciferase signal (ordinate data) is different in scale. Data points are shown as mean values-SEM=6 per group for each experiment). *Significant difference (by post-hoc analysis) between AAV1-P0-ICE and control groups at $p<0.002$ (A) and $p<0.001$ (B). In both (A) and (B), one in the control group out of six tumors regressed spontaneously, and all animals were taken into consideration in data analysis. (C)-(D) HEI-193-FC cells (30,000 in C or 60,000 in D) were implanted into the sciatic nerves of nude mice and tumor volumes monitored by in vivo bioluminescence imaging. At times indicated by arrows, tumors were injected twice (two separate injections one week apart) with AAV1-P0mICE, AAV1-P0-hICE or AAV1-P0-GFP vectors. Bioluminescence (flux) in panels C and D is expressed in different units as they were obtained using different bioluminescence imaging systems. Data shown as mean±S.E.M. (N=6 per group except N=4 in panel B for AAV1-P0-mICE and AAV1-P0-GFP); *$p<0.001$ between AAV1-P0-ICE and controls. In C, 1 out of 6 control group tumors regressed spontaneously, but 0 of 6 in D. All animals were included in data analysis.
Figure 4:
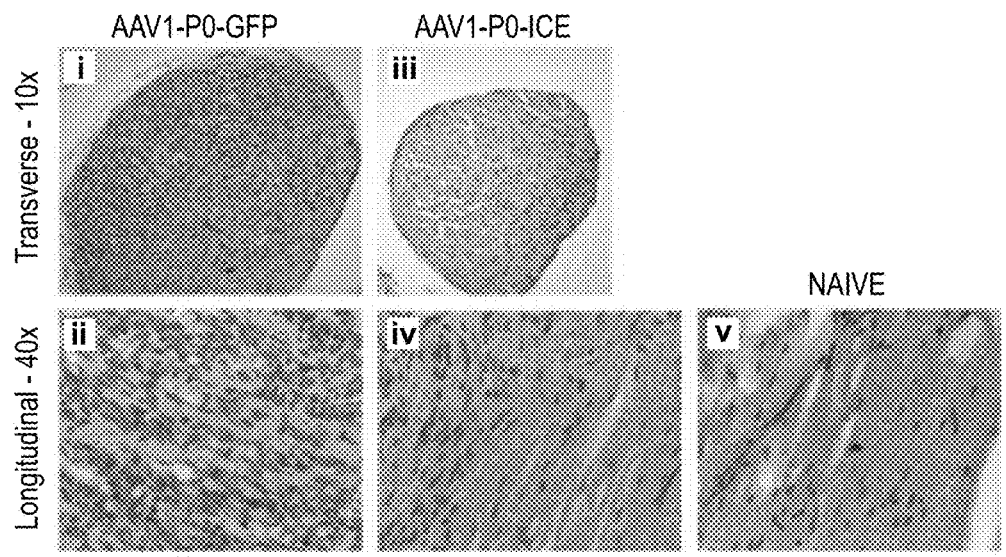
FIG. 4 depicts in accordance with various embodiment of the invention the microscopic evaluation of AAV1-P0-ICE- and AAV1-P0-EGFP-injected HEI-193FC schwannomas. (A) Hematoxylin and eosin (H&E) staining of a transverse section of (i) a representative sciatic nerve with abundant hematoxylin-positive tumor cells (darkly staining cells) 11 weeks after AAV1-P0-EGFP control vector injections (two injections spaced 1 week apart, $1\times10^{10}$ GC in 1 µl) into an experimental schwannoma; and (iii) a representative sciatic nerve of normal diameter with only a few hema-toxylin-positive cells 11 weeks after AAV1-P0-ICE vector injections (two injections spaced 1 week apart, $1\times10^{10}$ GC in 1 µl) into an experimental schwannoma. Higher power (original magnification, ×40) images of H&E-stained, longitudinal sections of sciatic nerves 11 weeks after vector injection of experimental schwannomas shows the presence of abundant, mitotically active tumor cells after AAV1-P0-EGFP injection (ii), but scant numbers of tumor cells after AAV1-P0-ICE injection (iv). Naive nerve (v) is shown for comparison. (B) H&E histology is shown for transverse sections. (i). Uninjected sciatic nerve. (ii). Sciatic nerve with HEI-193FC schwannoma 5 weeks after cell implantation in nu/nu mice, just prior to vector injection. (iii). Sciatic nerve with schwannoma 11 weeks after injection of AAV1-P0-GFP vector ($1 \times 1010$ g.c. in 1 μl) showing abundant hematoxylin-positive tumor cells (darkly staining). (iv) Sciatic nerve with experimental schwannoma injected 11 weeks prior with AAV1-P0-ICE vector (same dose) showing normal nerve diameter and only a few dark hematoxylin-positive cells. e-g. H&E histology for longitudinal sections corresponding to panels (ii)-(iv), respectively. Magnification=10×.
Figure 4:
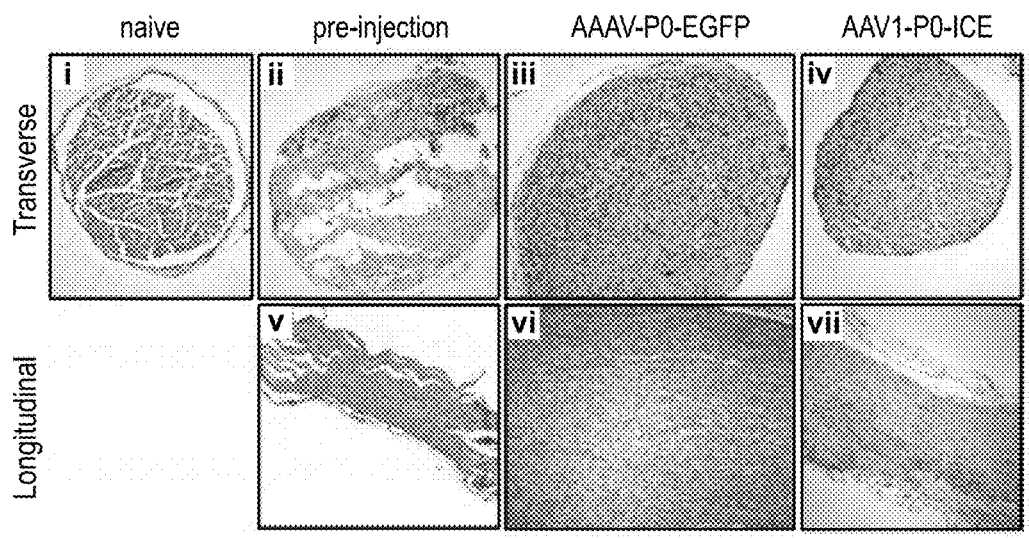

Postmortem histological evaluation of formalin-fixed, paraffin-embedded sections stained with H&E was performed on animals from both experiments shown in FIGS. 3A and B. This revealed substantial tumor burden in nerves injected with control AAV vector (AAV1-P0-EGFP) (FIG. 4Ai and 4Aii), but only scant tumor cells in nerves injected with the AAV1-P0-ICE vector at 11 weeks after vector injection (FIG. 4Aiii and 4Aiv), as compared with normal nerve (FIG. 4Av). Control animals implanted with HEI-193FC cells, but not injected with vector, also demonstrated significant tumor burden by H&E staining at this time point.

FIG. 4B shows the growth of tumors and regression after vector treatment by histopathologic analysis.

Example 4

AAV1-P0-ICE Vector is not Neurotoxic

Figure 5:
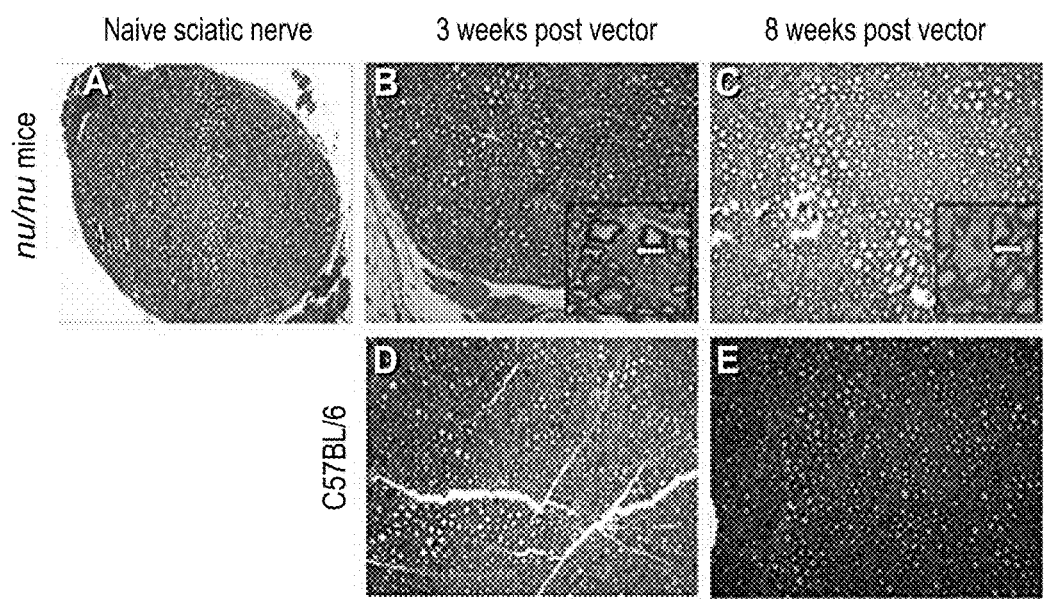
FIG. 5 depicts in accordance with various embodiments of the invention, the neuropathological evaluation of sciatic nerve after AAV1-P0-ICE injection. Shown is toluidine blue staining of myelin in Epon-embedded sciatic nerve of nude mice (A-C) and immunocompetent C57BL/6 mice (D and E). Cross-sections of naive sciatic nerve (A), and 3 weeks (B and D), and 8 weeks (C and E) after the first of two weekly injection of AAV1-P0-ICE, show essentially normal nerves with rare axonal degeneration [(B), inset] and occasional macrophage infiltration [(C), inset] marked by arrows. Sciatic nerves of C57BL/6 mice (D and E) showed normal myelination and axonal integrity. Original magnification: (A) ×20; (B-E): ×40; insets: ×100.

Major concerns in using a vector encoding a proapoptotic protein under a Schwann cell-specific promoter are the potential toxicity to normal Schwann cells and consequent axonal injury of neurons. Neuropathological evaluation of sciatic nerve sections from nude mice collected 3 and 8 weeks after two injections of the AAV1-P0-ICE vector ($10^{10}$ GC in 1 µl, 1 week apart) into non-tumor-bearing sciatic nerves revealed normal density of axons and no evidence of demyelination (FIGS. 5B and C), as compared with normal uninjected nerve (FIG. 5A). Degenerating axons (FIG. 5B, inset) and macrophages (FIG. 5C, inset) were observed only rarely. H&E and toluidine staining of myelin failed to reveal evidence of acute or chronic inflammation. Identical findings were obtained with immunocompetent C57BL/6 mice, that is there was no significant neuropathology in AAV1-P0-ICE-injected sciatic nerves (FIGS. 5D and E).

Figure 6:
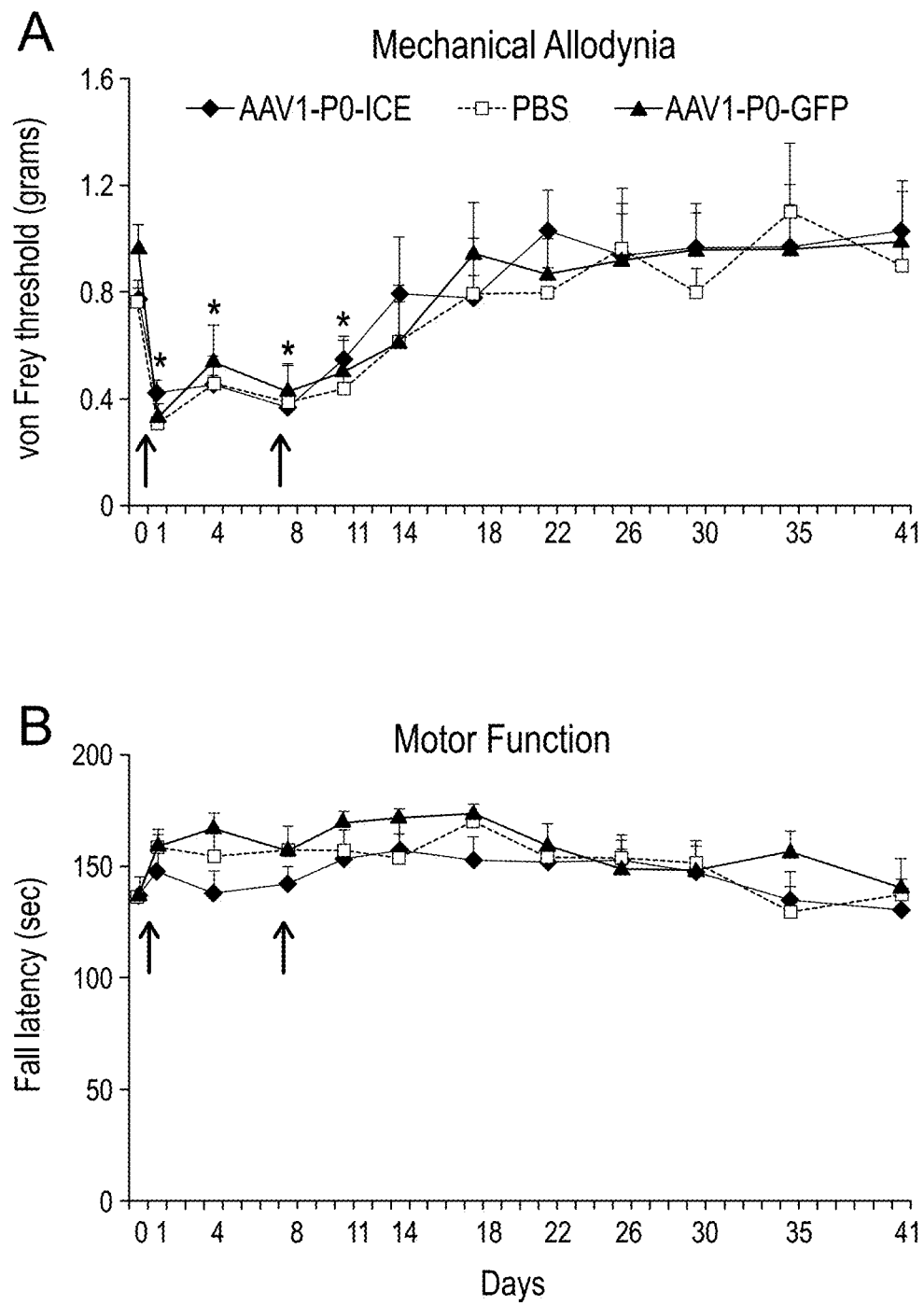
FIG. 6 depicts in accordance with various embodiments of the invention the effects of AAV1-P0-ICE nerve injection on pain behavior and motor function. Normal sciatic nerves in immune-competent (C57BL/6) mice were injected with AAV1-P0-GFP vector or AAV1-P0-ICE vector ($1 \times 10^{10}$ GC in 1 μl) or PBS two times over a 1-week period (4 and 10 days, arrows). Pain (von Frey method) and motor control (rotarod) were evaluated at 4-day intervals for 41 days. Results are represented as the mean-SEM of n=12 mice per group. Arrows indicate times of vector injection. *Significantly different from baseline for all groups ($p \leq 0.001$).

Sensory/pain and motor function tests were used to assess possible phenotypic alterations in C57BL/6 (immunocompetent) and nude (immunodeficient) mice resulting from intrasciatic nerve injections of AAV1-P0-ICE, AAV1-P0-GFP (both vectors at $10^{10}$ GC in 1 iil, two injections 1 week apart), or PBS (1 µl, two injections 1 week apart). Mechanical ("pain") sensitivity (allodynia) was tested with von Frey filaments to establish withdrawal threshold of the hind paw ipsilateral to the injected sciatic nerve (FIG. 6A). Gross motor performance was assayed by the accelerating rotarod test (FIG. 6B). Although there was an expected temporary decrease in the von Frey withdrawal threshold (i.e., mechanical hyperalgesia interpreted as a painlike behavior) after the surgical manipulation required for injection, mechanical sensitivity did not differ between the AAV1-P0-ICE, AAV1-P0-GFP, and PBS groups over 5 weeks after injections, and the threshold for all groups returned to preinjection baseline within 2 weeks of vector injection. Thus, there was no sustained change in sensory function associated with vector injection. Further, there was no decrease in rotarod performance in any group at any time during the study. The data in FIG. 6 were obtained from C57BL/6 mice; statistically identical results were obtained with nude mice.

Biodistribution studies were carried out after injection of AAV1-P0-ICE or AAV1-P0-GFP vector ($10^{10}$ GC in 1 µl, 1 week apart) or PBS (1 µl, 1 week apart) into the sciatic nerve of nude mice (n=2 animals per group; AAV1-P0-ICE, AAV1-P0-GFP, or PBS). Sciatic nerve and DRG, both ipsilateral and contralateral to injection, as well as spinal cord were collected 3 weeks later and evaluated for the presence of vector by qPCR Vector was found in the sciatic nerve and DRG in all samples ipsilateral, but not contralateral, to vector injections, as well as in all spinal cord samples (Table 1). Although vector was detectable in the DRG and spinal cord, immunohistological analysis of these tissues 8 weeks after a series of two intrasciatic AAV1-P0-GFP injections into adult mice (same method as described previously) failed to reveal any GFP fluorescence, suggesting that protein expression in these tissues is negligible.

TABLE 1

AAV BIODISTRIBUTION AS DETERMINED BY qPCR

| | AAV1-P0-ICE | | AAV1-P0-GFP | |
|---|---|---|---|---|
| | Ipsilateral | Contralateral | Ipsilateral | Contralateral |
| Sciatic nerve | + | − | + | − |
| DRG | + | − | + | − |
| Spinal cord | | + | | + |

DRG, dorsal root ganglia.

The observed absence of AAV-P0-ICE mediated neuronal and Schwann cell toxicity can be accounted for by P0 control of transgene expression. We hypothesized that the relatively low expression of P0 in the Schwann cells of adult mice would limit transgene expression after intrasciatic injection of our AAV vectors. P0 promoter expression in Schwann cells is greater in young than in adult mice, with expression peaking at 1 month of age and decreasing to about 50% of peak by 2 months (Shen et al., 2011). Further, neurotoxicity would not be expected to occur because the P0 promoter is not expressed in neurons (Prabhakar et al., 2010).

To test this hypothesis, we injected the sciatic nerves of young (postnatal day 21 [P21]) and adult (14-week-old) immune-competent C57BL/6 mice with AAV1-P0-GFP and collected sciatic nerves and DRG 10 days later for histological analysis of GFP expression (FIG. 7A, top four panels; and FIG. 7B, top two panels). In the sciatic nerve there was greater GFP expression after AAV1-P0-GFP injection in P21 mice compared with 14-week-old animals, consistent with lower P0 expression in adult mice. In DRG, there was no detectable GFP expression in either young or adult mice after AAV1-P0-GFP injection (FIG. 7B, top panels), consistent with constitutively low P0 expression in neurons. These results suggest that use of the P0 promoter in the AAV1-P0-ICE vector limits expression in Schwann cells and neurons after vector injection into the sciatic nerve of adult animals. This may explain the lack of observed vector-associated toxicity.

To further validate our results, we compared GFP expression after intrasciatic injection of AAV-P0-GFP with injection of AAV1-CBA-GFP. The CBA promoter is ubiquitously expressed (Gray et al., 2011). We found greater GFP expression when under CBA promoter control compared with P0 in both sciatic nerve (FIG. 7A) and DRG (FIG. 7B). Interestingly, we also found some indication that there was greater GFP expression in the sciatic nerve of young mice compared with adult mice after AAV1-CBA-GFP injection, suggesting that myelination, which is incomplete in young but complete in adult mice, may protect against adenoviral vector infection (FIG. 7A). However, given the high level of GFP transgene expression in both young and adult mice when GFP is under CBA control, we conclude that use of the P0 promoter is more important than degree of myelination in protection from AAV1-P0-ICE toxicity.

Example 5

Figure 8:
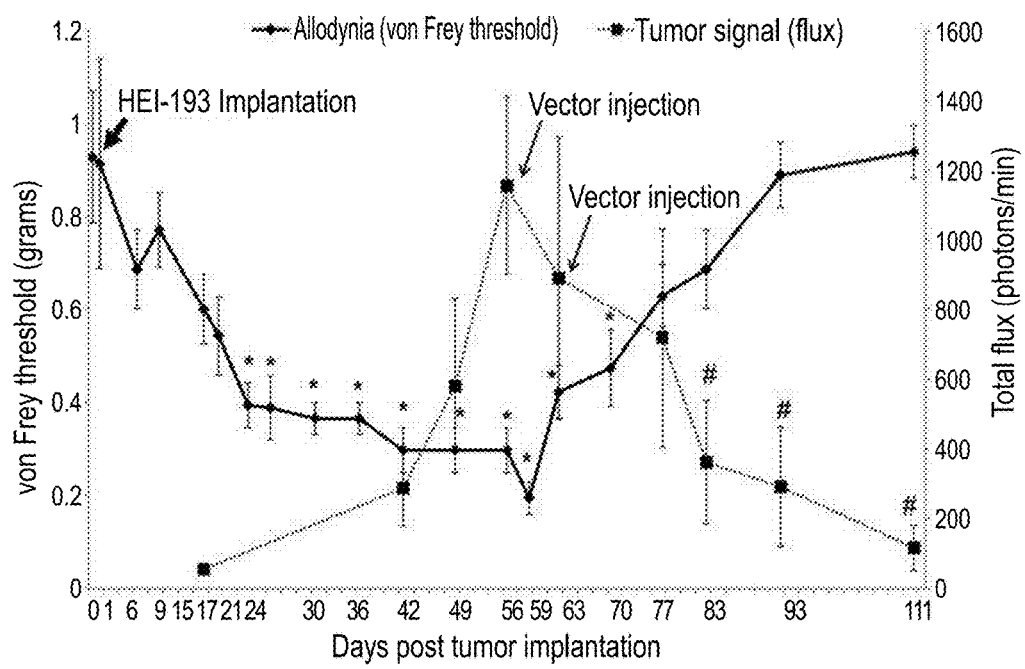
FIG. 8 depicts in accordance with various embodiments of the invention the effect of AAV1-P0-ICE-mediated tumor regression on pain behaviors in proximally implanted sciatic nerve HEI-193FC schwannomas. Sixty thousand HEI-193FC cells were implanted into the sciatic nerve, at the level of the pelvis, in nude mice and tumor-associated bioluminescence was monitored at weekly intervals by in vivo bioluminescence imaging. Eight weeks after tumor implantation, at a time when painlike nocifensive behavior (i.e., decreased von Frey threshold in the plantar surface in foot ipsilateral to tumor) was well established, tumors were injected twice, 1 week apart, with AAV1-P0-ICE or AAV1-P0-GFP vector ($1 \times 10^{10}$ GC in 1 μl per injection). Arrows indicate times of vector injection. The solid line shows the von Frey threshold and the dotted line shows total flux, the former a measure of mechanical sensitivity and the latter a measure of tumor volume. As evident in the graph, AAV1-P0-ICE-mediated tumor regression is correlated with a return of the von Frey threshold to normal baseline. *Significantly different ($p<0.05$) from preimplantation baseline for von Frey threshold; #significantly different ($p<0.05$) from maximal total flux corresponding to tumor volume.

Proximal Sciatic Nerve Implantation of Schwannoma Cells Leads to Pain Like Behavior that is Relieved by AAV1-P0-ICE Treatment As persistent pain can be a major clinical issue in patients with schwannomatosis and NF2, and HEI-193FC tumors implanted in the distal sciatic nerve of mice did not produce painlike behavior (i.e., no decreased von Frey threshold), we endeavored to generate an experimental schwannoma model that would mimic clinical schwannoma-related pain. We hypothesized that more proximal implantation of HEI-193FC cells would lead to mechanical sensitization due to nerve compression, because in the proximal sciatic nerve expansion of tumors is limited by pelvic structures. As shown in FIG. 8, growth of proximal schwannomas was associated with a significant decrease in the von Frey threshold in the hind paw ipsilateral to tumor site starting at 3 weeks post-implantation. This mechanical sensitization persisted until approximately 3 weeks after initial AAV1-P0-ICE injection. As is evident in FIG. 8, AAV1-P0-ICE injection led to a statistically significant regression of tumors [one-way ANOVA: $F(8,54)=2.80$, $p=0.01$] and an associated return of von Frey threshold values to baseline (i.e., normalization of pain sensitivity) as indicated by one-way ANOVA [$F(19,120)=7.8$, $p<0.0001$].

Example 6

Figure 9:
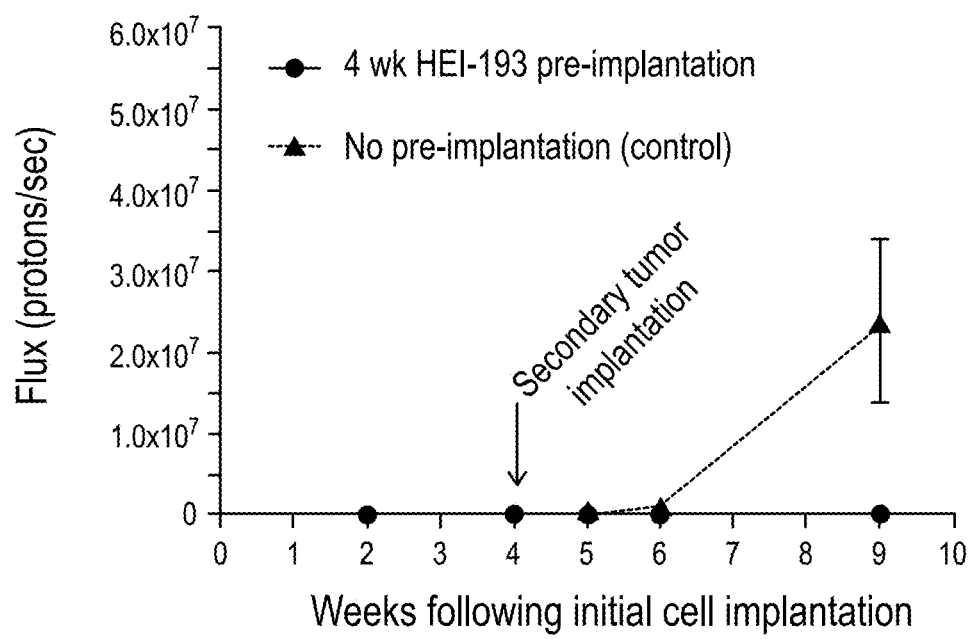
FIG. 9 depicts in accordance with various embodiments of the invention that intra-sciatic implantation of HEI-193 cells transfected in vitro with AAV-P0-ICE plasmid does not lead to tumor formation (weeks 0-4) in nude mice. At week 4 non-transfected HEI-193 cells were implanted at the site of prior transfected-cells implantation (filled circles) or in naive control mice (filled triangles). N=6 animals/group. Tumor growth was assessed via bioluminescence imaging. There was a significant difference ($p=0.02$) in tumor size between pre-implanted and control mice.
Figure 10:
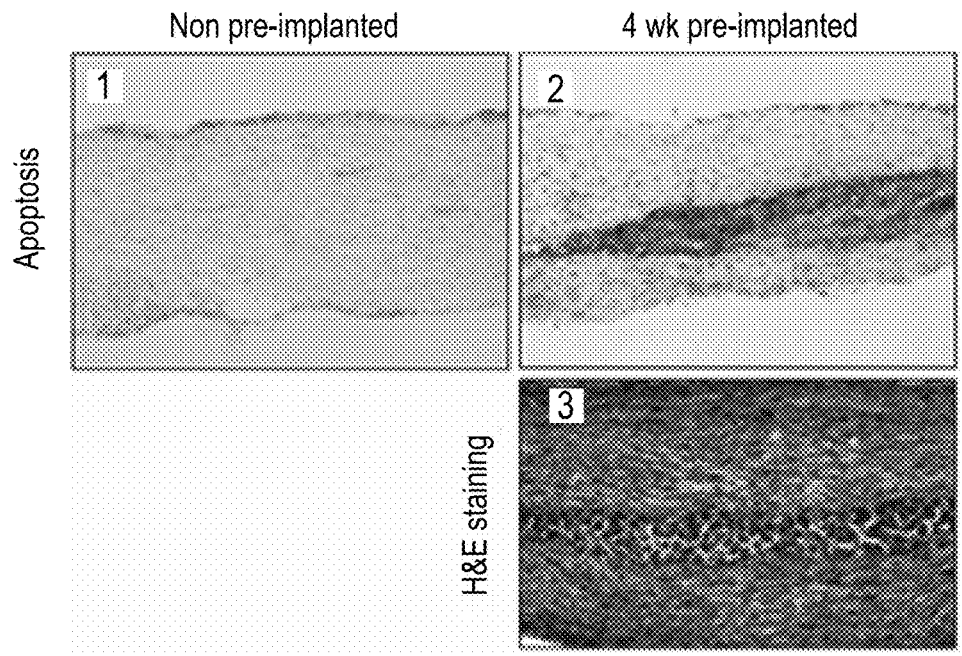
FIG. 10 depicts in accordance with various embodiments of the invention intra-sciatic implantation of HEI-193 cells transfected in vitro with AAV-P0-ICE plasmid does not lead to tumor formation. The upper rows show pyroptotic cell death (brown staining) observed 1 day (A) and 1 week (B) after implantation of non-transfected HEI-193 cells in pre-implanted (2) and control mice (1). The bottom two rows (3, 4) show H&E staining of the same tissues. No pyroptosis was observed in the control animals that were not pre-implanted with caspase-1 transfected HEI-193 cells (A1 and B1). Nerves from control mice at 1-week following HEI-193 cell implantation show disruption of nerve ultrastructure in area of tumor development (B3). Nerves that were pre-implanted with caspase-1 transfected HEI-193 cells showed extensive pyroptosis in the area of non-transfected HEI-193 tumor cells implantation (A2). By week 1, the pyroptosis in pre-implanted nerves was much diminished compared with day-1 (B2) (suggesting that tumor cell death occurs prior to the 1-week time point), and the structure of the nerve at 1-week was intact (B4).
Figure 10:
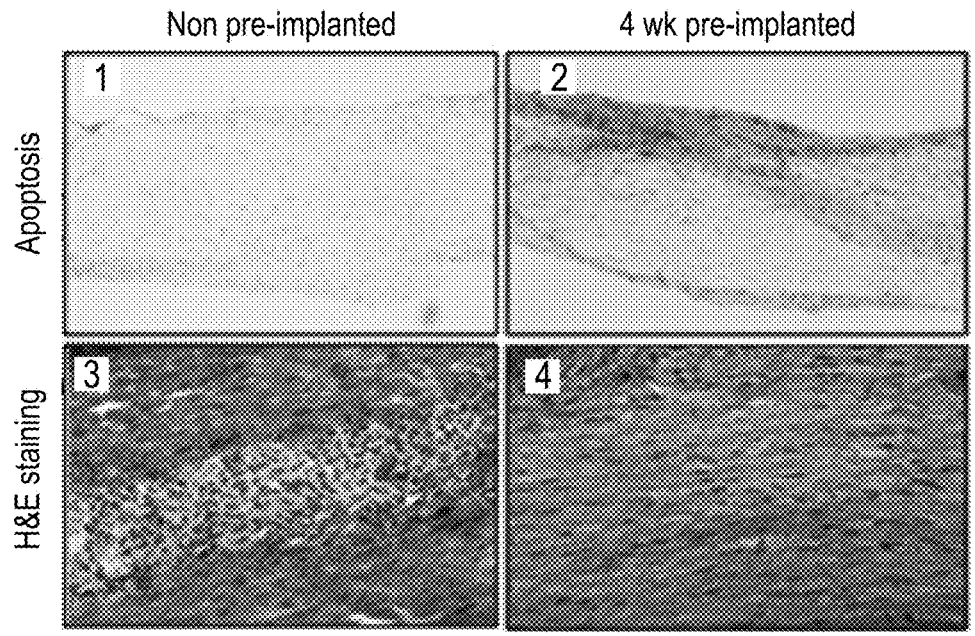

Generation of an Anti-Tumor Micro-Environment Following Implantation of Caspase-1 Transfected Schwannoma Cells The data shown in FIG. 9 demonstrate that pre-implantation of the sciatic nerve with AAV-P0-ICE transfected HEI-192 cells leads to generation of an anti-tumor microenvironment. In FIG. 10, we present histo-pathological analysis of nerves that were pre-implanted with AAV-P0-ICE transfected schwannoma cells prior to re-implantation with HEI-193 schwannoma cells. For data shown in FIG. 9, HEI-193 cells were transfected in vitro with AAV-P0-ICE plasmid and 24 hours later were implanted in nude mice. No tumors develop as all implanted caspase-1 expressing tumor cells die within 36 hours. Four weeks following pre-implantation, the same sciatic nerves were re-implanted with non-transfected HEI-193 cells; naïve control mice were implanted with HEI-193 cells in the sciatic nerve at that time (FIG. 9). Tumor growth was followed for 5 weeks after re-implantation of HEI-193 cells. Tumors development was significantly inhibited in animals pre-implanted with AAV-P0-ICE transfected cells compared to control mice (FIG. 9). Animals (n=2/group/time-point) from experimental and control groups shown in FIG. 9 (mice pre-implanted AAV-P0-ICE transfected HEI-193 cells and naïve control) were sacrificed 1 day and 1 week after implantation of non-transfected HEI-193 tumor cells and sciatic nerves were analyzed for pyroptosis and structural integrity of the nerve (FIG. 10)

Example 7

Figure 11:
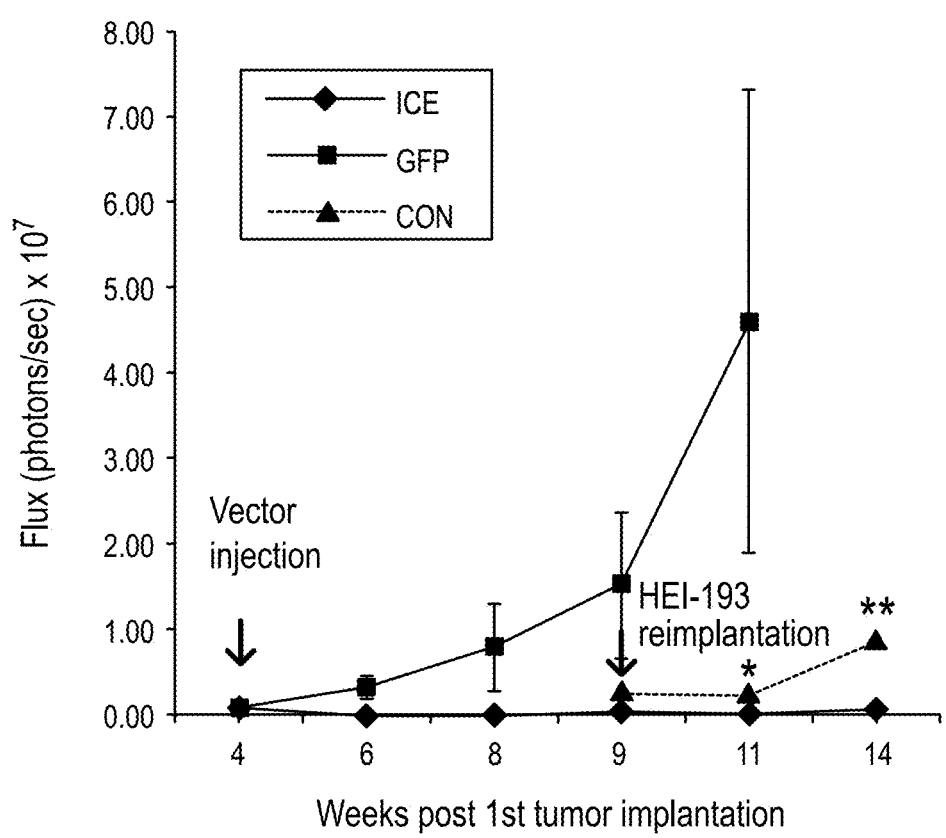
FIG. 11 depicts in accordance with various embodiments of the invention the generation of an anti-tumor microenvironment following AAV-P0-ICE treatment of an established ontra-sciatic HEI-193 schwannoma. Nude mice were implanted with HEI-193 cells and tumors allowed to develop for 4 weeks before injection of AAV-P0-ICE (ICE) or AAV-P0-GFP (GFP). 5 weeks later (week 9), tumors treated with AAV-P0-ICE had completely resolved, and HEI-193 cells were again implanted in the same location of the original tumors in the AAV-P0-ICE treated animals. In parallel, naive control mice (CON) were implanted in the sciatic nerve with HEI-193 cells. The asterisks indicate statistical difference between tumor signal in control (CON) and experimental groups (ICE weeks 9-14).

Generation of an Anti-Tumor Microenvironment Following AAV-P0-ICE Treatment of an Established Intra-Sciatic HEI-193 Schwannoma We obtained results corroborating the data shown above utilizing a model in which an established HIE-193 schwannoma is treated in vivo with the AAV-P0-ICE vector, the tumor resolves, and 4 weeks following tumor resolution HEI-193 cells are re-implanted at the site of the original schwannoma (FIG. 11). Age-matched naïve control mice were implanted with HEI-193 cells at the same time that experimental animals were re-implanted. Animals in the experimental group showed significantly diminished tumor growth compared with naïve controls (FIG. 11). Of note, a group of animals with HEI-193 tumors were injected with AAV-P0-GFP at the same time as the mice injected with AAV-P0-ICE as a second control group to demonstrate efficacy of the AAV-P0-ICE vector (FIG. 11).

Example 8

Figure 12:
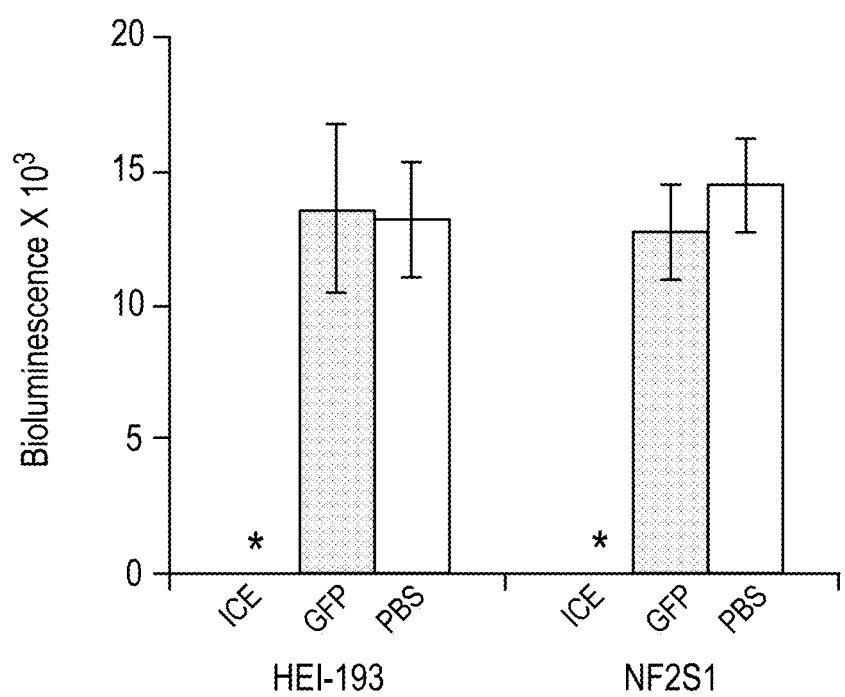
FIG. 12 depicts in accordance with various embodiments of the invention that in vitro AAV-P0-ICE transfection of schwannoma cell lines induce bystander killing of tumor cells. Supernatants conditioned with schwannoma cells (human HEI-193 and mouse NF2S1 cells) transfected in vitro with the AAV-P0-ICE (ICE), AAV-P0-GFP (GFP), or mock solution (PBS) for 48 hours were applied on non-transfected cells growing in vitro. Two days later cells viability was measured through a bioluminescence assay. Supernatants extracted from cells transfected with AAV-P0-ICE killed the non-transfected cells, but not those from AAV-P0-GFP or PBS transfected cells.
Figure 13:
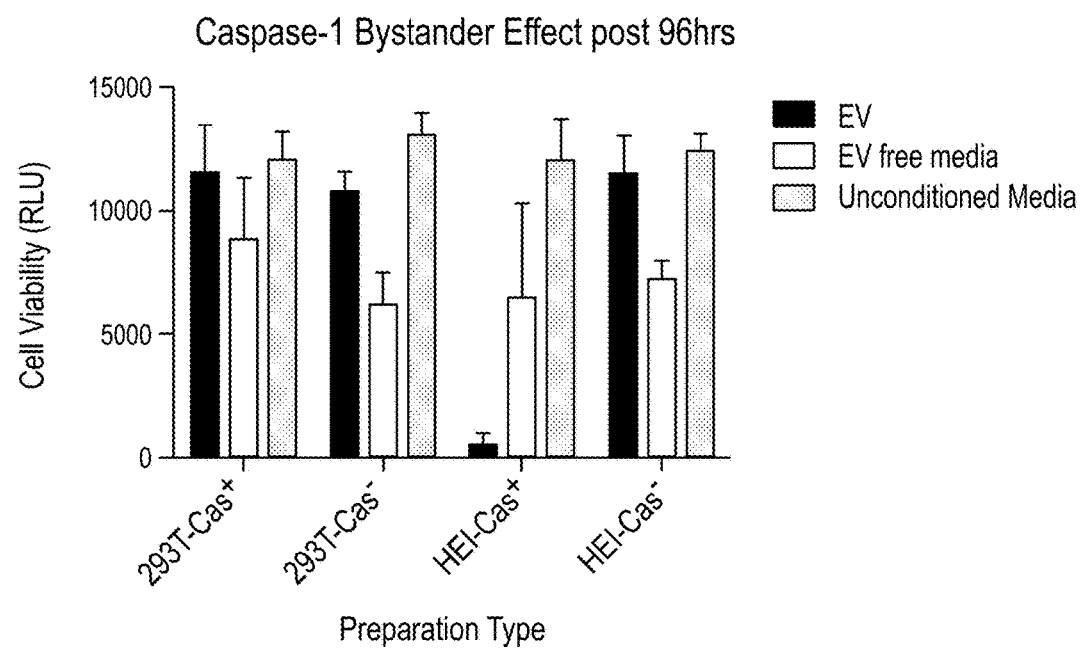
FIG. 13 depicts in accordance with various embodiments of the invention that in vitro AAV-P0-ICE infection of schwannoma cell lines induce bystander killing of tumor cells. Viability of cultured HEI-193 cells 96 hours after preparations of extracellular vesicles (EV) or EV-free cultured media were added to healthy recipient HEI-193 schwannoma cells or control 293T cells. Cas+ refers to EV's or EV-free cultured media from HEI-193 cells transfected with caspase-1, while Cas− refers to similar fraction derived from non-transfected cells.

In Vitro AAV-P0-ICE Infection of Schwannoma Cell Lines Induces Bystander Killing of Tumor Cells The existence of a bystander schwannoma killing mechanism was observed in experiments utilizing cultured schwannoma cells. Data in FIG. 12 demonstrate the existence of a death-signal secreted by tumor cells transfected with AAV-P0-ICE, but not from AAV-P0-GFP transfected control cells. We have gathered further data that this bystander cell killing may be mediated by extracellular vesicles (EVs) released from AAV-P0-ICE infected tumor cells (FIG. 13). Cells treated with unconditioned media (UM) showed no cell death. As shown in FIG. 13, cells treated with EV-free conditioned media showed less viability when compared to the unconditioned media controls, in both the Cas+ and Cas− groups; this likely represents decreased nutrient value of the conditioned media. Importantly, HEI-193 schwannoma cells exposed to EVs had significantly decreased (***P<0.0005) viability compared to HEI-193 cells exposed to EV free medium; this signifies specific EV-mediated toxicity. This effect was not observed in 293T cells suggesting specificity for schwannoma cells. RLU=relative light units (arbitrary units). EVs from affected individual (for example, dendritic cells or mesenchymal stem cells from bone marrow) are currently being used in clinical trials for vaccination purposes and could be adapted as the therapeutic vehicle, thereby avoiding immune reaction to the AAV capsids.

Example 9

In certain application, the product would be an AAV1 vector encoding human caspase-1 (ICE-1) followed by a bovine growth hormone polyadenylation signal under a rat Schwann cell specific promoter (AAV1-P0-hICE). The plasmid was derived from dsAAV-CBA-GFP-BGHpA (Broekman et al., 2007) and carries two AAV2 ITR elements, one wild-type and one in which the terminal resolution site was deleted, as described (McCarty et al., 2003), generating a vector that is packaged as a double-stranded molecule. The dsAAV-P0-ICE plasmids [encoding human (h) or mouse (m) ICE] were generated by replacing the chicken beta actin promoter (CBA)-GFP cassette in the parent plasmid with PCR amplified rat P0 promoter and cDNA for hICE or mICE (Prabhakar et al., 2010). These vector constructs will have been fully sequenced to validate composition. Vector will be packaged under GMP conditions by the NHLBI Gene Therapy Resource Program AAV Clinical Vector Laboratory at Children's Hospital of Philadelphia (CHOP) under the direction of Dr. Wright. Vector batches will be prepared in compliance with current Good Manufacturing Practices appropriate for their intended use (21CFR, parts 210, 211, 600, 610; FDA Guidance for Industry, 2006), and quality control (QC) tested in accordance with federal regulatory guidelines and industry standards for biologics to ensure optimal product safety, consistency, purity and potency. Vector will be stored in 100 µl aliquots of 1013 genome copies (g.c.) per ml in PBS with 5% sorbitol stored at −80° C. and thawed just prior to use with the consistency across the clinical trial.

The target patient population may consist of adults with 1-3 cm (diameter) schwannomas along peripheral nerves causing severe, essentially untreatable pain. The target population may be patients with schwannomatosis, NF1, NF2, and/or schwannomas of unspecified origin. Exclusion criteria would include a malignancy in the last 3 years prior to start of study treatment, pregnant or nursing (lactating) females, the presence of any co-morbid medical conditions that would contraindicate participation in the trial, as well as an antibody titer to AAV1 of >1:5-1:10 by neutralizing antibody assay. In any patient for whom resection of the tumor is planned, we will obtain tissue for analysis of vector genomes and pathology.

Based on: 1) our mouse experiments in which 0.3 cm diameter tumors regress following two injections of $10^{10}$ g.c. AAV1-P0-hICE in 1 µl: and 2) that the size of treated tumors in humans (or animals) will be 1-3 cm in diameter (with an average volume ~100 times that of the mouse tumors), we envision a dose escalation curve in which we will inject $3\times10^{11}$ g.c. in 30 µl, followed by $10^{12}$ g.c. in 100 µl, and $3\times10^{12}$ g.c in 300 µl. Vector will be injected directly into tumors using a 25 gauge spinal needle (length to depend upon site of injection) under ultrasound guidance and with 1% lidocaine under local anesthesia.

We have validated a treatment strategy for schwannomas in which an AAV vector delivers an apoptotic protein, ICE, under the control of the Schwann-cell specific promoter P0, causing selective death of tumor cells. Using a xenograft model in which human NF2 schwannoma tumors form in the distal sciatic nerve of nude mice, we both prevented development of early schwannomas and caused regression of well-established tumors with minimal to no nerve damage through direct intratumoral injection of this AAV1-P0-ICE vector. In a related paradigm devised to model tumor-associated pain, the same human schwannoma cells were implanted more proximally in the sciatic nerve of mice with tumor development leading to mechanical hypersensitivity (i.e., pain behavior). Treatment of these tumors with AAV1-P0-ICE resulted in concurrent tumor regression and normalization of mechanical sensitivity. We have also shown that injection of the AAV1-P0-ICE vector into the sciatic nerve of both nude (nonimmune-competent) and immune-competent mice is not associated with any apparent neuropathology as indicated by histological evaluation and behavioral testing.

Several aspects of this study were surprising. The first was the selective killing of schwannoma cells by AAV1-P0-ICE while leaving resident Schwann cells (and neuronal axons) intact. ICE was the first mammalian caspase identified (Miura et al., 1993) and expression causes rapid lysis of cells associated with inflammatory activity (Miao et al., 2011). In some models ICE expression has been associated with neurodegeneration (Friedlander, 2000) and demyelination (Furlan et al., 1999). However, extensive evaluation of peripheral nerve integrity and function, including neuropathology, nerve conduction velocity, and behavior (pain sensitization and rotarod performance), revealed minimal to no damage after direct injection of AAV1-P0-mICE into the sciatic nerve (present study) (Prabhakar et al., 2010).

Protection of normal nerve may be attributed to the use of the P0 promoter, which normally regulates expression of a major myelin glycoprotein that is at its highest levels in Schwann cells during myelination, occurring at 1 month of age during normal development (Lee et al., 1997; Shen et al., 2011). Expression of P0 decreases by about 50% at 2 months of age (Shen et al., 2011) the time of vector injection in our studies. Accordingly, our results indicate decreased GFP expression in the sciatic nerve when AAV-P0-GFP was injected into the nerve of 2-month-old mice compared with P21 mice. This decrease in transgene expression in older mice after AAV-CBA-GFP injection raises the possibility that degree of Schwann cell myelination reduces vector infectivity.

A second surprising finding was the extensive remission of tumors after injection of the AAV1-P0-ICE vector (two intratumoral injections of $10^{10}$ GC vector in 1 µl). On the basis of other tumor injection studies it is unlikely that all the tumor cells were infected with the vector, albeit infection efficiency varies with serotype and tumor type (Teschendorf et al., 2010). Although we estimate, based on the rate of growth as monitored by bioluminescence imaging (Saydam et al., 2011), that the MOI of tumor cells was about 3000

GC/cell, it is unlikely that the vector inoculum dispersed uniformly throughout the tumor. The high extent of tumor killing observed may be explained by the finding that ICE can be delivered from one cell to another via microvesicles, resulting in death of recipient cells (Sarkar et al., 2009), and the likelihood that schwannoma cells, like other tumor cells, are highly active in microvesicle release (Taylor and Gercel-Taylor, 2008; Balaj et al., 2011). The myelin sheath on Schwann cells may also block uptake of microvesicles. A third surprising finding was that we saw little to no sign of macrophage cell invasion into the nerve after AAV1-P0-ICE injection in nude and immune-competent mice, considering that ICE is a central component of the inflammasome complex (Lamkanfi and Dixit, 2009). It remains possible that some macrophages moved in and out quickly after AAV1-P0-ICE vector injection and were no longer present at the earliest time point we evaluated (3 weeks after the second of two vector injections).

Complete assessment of our AAV-P0-ICE therapeutic strategy for the treatment of schwannoma requires testing in immune-competent animals. We expect that in immune-competent mice we will observe a stronger inflammatory response compared with nude mice, and this may lead to greater neurotoxicity. However, AAV-P0-ICE tumor treatment in immune-competent mice also has the potential to establish both innate and adaptive antitumor immunity. If the latter host immune responses do occur, AAV-P0-ICE treatment of a single lesion may lead to systemic changes that cause regression of distal NF2 lesions and vaccinate animals from the development of tumors after implantation at a later time. This is a crucial issue in the treatment of patients with NF2 given the typical presence of multiple lesions in a given individual and the development of tumors over long time periods. We are currently testing this, using the NF2S-1 mouse schwannoma line (Prabhakar et al., 2007) implanted in the sciatic nerve of Swiss mice and the 08031-9 muse NF2 primary cells implanted in the sciatic nerve of FVB/N mice (Tanaka et al., Clinical Cancer Research, 2013).

Current therapy for NF2 and schwannomatosis tumors involves surgical resection or radiosurgery of symptomatic lesions and symptomatic management of pain. There are several significant limitations to these available treatments. The location of tumors can make surgical resection infeasible because of the unacceptable risk of morbidity (e.g., lesioning of cervical nerve roots) or mortality (e.g., damage to the brainstem). Even when resection is possible, significant morbidity may be associated with the operation. Further, schwannomas especially in schwannomatosis can be associated with excruciating, persistent pain for which surgical resection may not be an option because of the number of tumors. Even if it is assumed that not all tumor cells would be destroyed by the vector, because schwannomas are slow growing and benign, a reduction in tumor mass would be expected to confer meaningful and prolonged symptomatic improvement.

These preclinical studies provide support for further progression toward phase 1 clinical trial evaluation of the AAV-P0-ICE vector for the treatment of schwannomas. AAV vectors have been shown to be safe for use in the human nervous system in a number of gene therapy trials (McPhee et al., 2006; Kaplitt et al., 2007; Eberling et al., 2008; Worgall et al., 2008; Bowers et al., 2011; McCown, 2011; Lentz et al., 2012). These vectors have also proven effective in treating malignant tumors in preclinical trials, although tumor cells that survive the initial infection continue to divide and thus lose AAV-delivered trans-genes (Meijer et al., 2009; Maitituoheti et al., 2011; Tamai et al., 2012). Further, conditional expression of another caspase, caspase-9, has proven safe and effective in preventing graft-versus-host disease in patients with leukemia treated with genetically modified T cells in clinical trials (Di Stasi et al., 2011).

Our preclinical findings in an orthotopic mouse model demonstrate the efficacy and safety of treatment of schwannomas with an AAV1-P0-ICE vector. These studies will help form the basis of translational studies in support of transition to phase 1 human trials as well vet trials. The use of AAV1-P0-ICE vectors for the treatment of neurofibromatosis holds the promise of preventing and reversing the substantial disability and suffering associated with schwannomatosis and NF2 tumors. This would reduce the need for surgical resection, which is invasive and can have substantial associated morbidity. On the basis of the ease of vector injection as compared with surgery, we anticipate that vector treatment would be more frequently sought out by patients, thereby potentially improving prognosis (through early treatment), as many of these benign tumors undergo malignant transformation over time.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

REFERENCES

1. Agarwal, N., Pacher, P., Tegeder, I., et al. (2007). Cannabinoids mediate analgesia largely via peripheral type 1 cannabinoid receptors in nociceptors. Nat. Neurosci. 10, 870-879.
2. Antinheimo, J., Sankila, R., Carpén, O., et al. (2000). Population-based analysis of sporadic and type 2 neurofibromatosis-associated meningiomas and schwannomas. Neurology 54, 71-76.
3. Balaj, L., Lessard, R., Dai, L., et al. (2011). Tumour microvesicles contain retrotransposon elements and amplified oncogene sequences. Nat. Commun. 2, 180.
4. Baser, M. E., Friedman, J. M., and Evans, D. G. (2006). Increasing the specificity of diagnostic criteria for schwannomatosis. Neurology 66, 730-732.
5. Bowers, W. J., Breakefield, X. O., and Sena-Esteves, M. (2011). Genetic therapy for the nervous system. Hum. Mol. Genet. 20, R28-R41.
6. Broekman, M. L., Comer, L. A., Hyman, B. T., and Sena-Esteves, M. (2006). Adeno-associated virus vectors serotyped with AAV8 capsid are more efficient than AAV-1 or -2 serotypes for widespread gene delivery to the neonatal mouse brain. Neuroscience 138, 501-510.
7. Brown, A. M., and Lemke, G. (1997). Multiple regulatory elements control transcription of the peripheral myelin protein zero gene. J. Biol. Chem. 272, 28939-28947.
8. Chen, Q., Peto, C. A., Shelton, G. D., et al. (2009). Loss of modifier of cell adhesion reveals a pathway leading to axonal degeneration. J. Neurosci. 29, 118-130.
9. Di Stasi, A., Tey, S. K., Dotti, G., et al. (2011). Inducible apoptosis as a safety switch for adoptive cell therapy. N. Engl. J. Med. 365, 1673-1683.
10. Eberling, J. L., Jagust, W. J., Christine, C. W., et al. (2008). Results from a phase I safety trial of hAADC gene therapy for Parkinson disease. Neurology 70, 1980-1983.
11. Eichler, F. S., Hornemann, T., McCampbell, A., et al. (2009). Overexpression of the wild-type SPT1 subunit lowers deso-xysphingolipid levels and rescues the phenotype of HSAN1. J. Neurosci. 29, 14646-14651.
12. Friedlander, R. M. (2000). Role of caspase 1 in neurologic disease. Arch. Neurol. 57, 1273-1276.
13. Furlan, R., Martino, G., Galbiati, F., et al. (1999). Caspase-1 regulates the inflammatory process leading to autoimmune de-myelination. J. Immunol. 163, 2403-2409.
14. Gray, S. J., Foti, S. B., Schwartz, J. W., et al. (2011). Optimizing promoters for recombinant adeno-associated virus-mediated gene expression in the peripheral and central nervous system using self-complementary vectors. Hum. Gene Ther. 22, 1143-1151
15. Hadfield, K. D., Newman, W. G., Bowers, N. L., et al. (2008). Molecular characterisation of SMARCB1 and NF2 in familial and sporadic schwannomatosis. J. Med. Genet. 45, 332-339.
16. Harris, J. E., Sheean, P. M., Gleason, P. M., et al. (2012). Publishing nutrition research: A review of multivariate techniques. 2. Analysis of variance. J. Acad. Nutr. Diet. 112, 90-98.
17. Huang, J. H., Simon, S. L., Nagpal, S., et al. (2004). Management of patients with schwannomatosis: Report of six cases and review of the literature. Surg. Neurol. 62, 353-361.
18. Hulsebos, T. J., Plomp, A. S., Wolterman, R. A., et al. (2007). Germline mutation of IN11/SMARCB1 in familial schwanno-matosis. Am. J. Hum. Genet. 80, 805-810.
19. Hung, G., Li, X., Faudoa, R., et al. (2002). Establishment and characterization of a schwannoma cell line from a patient with neurofibromatosis 2. Int. J. Oncol. 20, 475-482.
20. Jacoby, L. B., Jones, D., Davis, K., et al. (1997). Molecular analysis of the NF2 tumor-suppressor gene in schwannomatosis. Am. J. Hum. Genet. 61, 1293-1302.

21. Jessen, K. R., and Mirsky, R. (2005). The origin and development of glial cells in peripheral nerves. Nat. Rev. Neurosci. 6, 671-682.
22. Juan, T. S., McNiece, L K., Jenkins, N. A., et al. (1996). Molecular characterization of mouse and rat CPP32 f3 gene encoding a cysteine protease resembling interleukin-1f3 converting enzyme and CED-3. Oncogene 13, 749-755.
23. Kaplitt, M. G., Feigin, A., Tang, C., et al. (2007). Safety and tolerability of gene therapy with an adeno-associated virus (AAV) borne GAD gene for Parkinson's disease: An open label, phase I trial. Lancet 369, 2097-2105.
24. Kirschbaum, K. M., Hiemke, C., and Schmitt, U. (2009). Rotarod impairment: Catalepsy-like screening test for antipsychotic side effects. Int. J. Neurosci. 119, 1509-1522.
25. Lamkanfi, M., and Dixit, V. M. (2009). Inflammasomes: Guardians of cytosolic sanctity. Immunol. Rev. 227, 95-105.
26. Lee, M., Brennan, A., Blanchard, A., et al. (1997). P0 is constitutively expressed in the rat neural crest and embryonic nerves and is negatively and positively regulated by axons to generate non-myelin-forming and myelin-forming Schwann cells, respectively. Mol. Cell. Neurosci. 8, 336-350.
27. Lentz, T. B., Gray, S. J., and Samulski, R. J. (2012). Viral vectors for gene delivery to the central nervous system. Neurobiol. Dis. 48, 179-188.
28. Lu-Emerson, C., and Plotkin, S. R. (2009). The neurofibromatosis. NF2 and schwannomatosis. Rev. Neurol. Dis. 6, E81-E86.
29. Maitituoheti, M., Li, Y., Wang, W., et al. (2011). Adeno-associated virus-mediated local delivery of LIGHT suppresses tumori-genesis in a murine cervical cancer model. J. Immunother. 34, 581-587.
30. McCarty, D. M., Fu, H Monahan, P. E., et al. (2003). Adeno-associated virus terminal repeat (TR) mutant generates self-complementary vectors to overcome the rate-limiting step to transduction in vivO. Gene Ther. 10, 2112-2118.
31. McClatchey, A. I., and Giovannini, M. (2005). Membrane organization and tumorigenesis—the NF2 tumor suppressor, Merlin. Genes Dev. 19, 2265-2277.
32. McCown, T. J. (2011). Adeno-associated virus (AAV) vectors in the CNS. Curr. Gene Ther. H, 181-188.
33. McPhee, S. W., Janson, C. G., Li, C., et al. (2006). Immune responses to AAV in a phase I study for Canavan disease. J. Gene Med. 8, 577-588.
34. Meijer, D. H., Maguire, C. A., LeRoy, S. G., and Sena-Esteves, M. (2009). Controlling brain tumor growth by intraventricular administration of an AAV vector encoding IFN-f3. Cancer Gene Ther. 16, 664-671.
35. Messerli, S. M., Tang, Y., Giovannini, M., et al. (2002). Detection of spontaneous schwannomas by MRI in a transgenic murine model of neurofibromatosis type 2. Neoplasia 4, 501-509.
36. Miao, E. A., Rajan, J. V., and Aderem, A. (2011). Caspase-1-induced pyroptotic cell death. Immunol. Rev. 243, 206-214.
37. Miura, M., Zhu, H., Rotello, R., et al. (1993). Induction of apo-ptosis in fibroblasts by IL-1 f3-converting enzyme, a mammalian homolog of the C. elegans cell death gene ced-3. Cell 75, 653-660.
38. Prabhakar, S., Messerli, S. M., Stemmer-Rachamimov, A. O., et al. (2007). Treatment of implantable NF2 schwannoma tumor models with oncolytic herpes simplex virus G47D. Cancer Gene Ther. 14, 460-467.
39. Prabhakar, S., Brennan, G. J., Messerli, S. M., et al. (2010). Imaging and therapy of experimental schwannomas using HSV am-plicon vector-encoding apoptotic protein under Schwann cell promoter. Cancer Gene Ther. 17, 266-274.
40. Rouleau, G. A., Merel, P., Lutchman, M., et al. (1993). Alteration in a new gene encoding a putative membrane-organizing protein causes neuro-fibromatosis type 2. Nature 363, 515-521.
41. Sarkar, A., Mitra, S., Mehta, S., et al. (2009). Monocyte derived microvesicles deliver a cell death message via encapsulated caspase-1. PLoS One 4, e7140.
42. Saydam, O., Ozdener, G. B., Senol, O., et al. (2011). A novel imaging-compatible sciatic nerve schwannoma model. J. Neurosci. Methods 195, 75-77.
43. Shen, D., Zhang, Q., Gao, X., et al. (2011). Age-related changes in myelin morphology, electrophysiological property and myelin-associated protein expression of mouse sciatic nerves. Neurosci. Lett. 502, 162-167.
44. Tamai, H Miyake, K., Yamaguchi, H., et al. (2012). AAV-8 vector expressing IL-24 efficiently suppresses tumor growth mediated by specific mechanisms in MLL/AF4-positive ALL model mice. Blood 119, 64-71.
45. Taylor, D. D., and Gercel-Taylor, C. (2008). MicroRNA signatures of tumor-derived exosomes as diagnostic biomarkers of ovarian cancer. Gynecol. Oncol. 110, 13-21.
46. Teschendorf, C., Emons, B., Muzyczka, N., et al. (2010). Efficacy of recombinant adeno-associated viral vectors serotypes 1, 2, and 5 for the transduction of pancreatic and colon carcinoma cells. Anticancer Res. 30, 1931-1935.
47. Worgall, S., Sondhi, D., Hackett, N. R., et al. (2008). Treatment of late infantile neuronal ceroid lipofuscinosis by CNS administration of a serotype 2 adeno-associated virus expressing CLN2 cDNA. Hum. Gene Ther. 19, 463-474.

The invention claimed is:

1. A recombinant adeno-associated virus (rAAV) vector of serotype AAV1 comprising a caspase-1 gene and a Schwann cell specific promoter.

2. The rAAV vector of claim 1, wherein the caspase-1 gene is a human, mouse, or rat caspase-1 gene.

3. The rAAV vector of claim 1, wherein the Schwann cell specific promoter comprises a P0 promoter or a peripheral myelin protein 22 (PMP22) promoter.

4. The rAAV vector of claim 1, wherein the Schwann cell specific promoter is upstream of the caspase-1 gene.

5. The rAAV vector of claim 1, further comprising a polyadenylation signal.

6. The rAAV vector of claim 5, wherein the polyadenylation signal is downstream of the caspase-1 gene.

7. The rAAV vector of claim 5, wherein the polyadenylation signal comprises a bovine growth hormone polyadenylation signal (BGHpA), a SV40 polyadenylation signal or a rabbit beta-globin polyadenylation signal.

8. The rAAV vector of claim 1, comprising a sequence as set forth in SEQ ID NO.: 4, or a sequence as set forth in SEQ ID NO.: 5.

9. The rAAV vector of claim 1, comprising a sequence as set forth in SEQ ID NO.: 6, or a sequence as set forth in SEQ ID NO.: 7.

10. The rAAV vector of claim 1, wherein the rAAV vector is a polynucleotide.

11. The rAAV vector of claim 1, wherein the rAAV vector is a single-stranded or double-stranded AAV.

12. The rAAV vector of claim 1, wherein the rAAV vector is a self-complementary AAV (scAAV).

13. The rAAV vector of claim 5, further comprising a first AAV inverted terminal repeat (ITR) located upstream of the Schwann cell specific promoter and a second AAV ITR located downstream of the polyadenylation signal.

14. The rAAV vector of claim 13, wherein the first or second AAV inverted terminal repeat comprises a deletion of the terminal resolution site.

15. The rAAV vector of claim 1, wherein the rAAV vector is a virus particle.

16. A method of treating, inhibiting, reducing the severity of and/or reducing the progression of a schwanoma related disease-state in a subject, comprising
    directly administering a therapeutically effective amount of a composition comprising an rAAV vector of serotype AAV1 comprising a caspase-1 gene and a Schwann cell specific promoter to a schwanoma in the subject, thereby treating, inhibiting, reducing the severity of and/or reducing the progression of the disease-state in the subject.

17. A pharmaceutical composition comprising:
    an rAAV vector of serotype AAV1 comprising a caspase-1 gene and a Schwann cell specific promoter; and
    a pharmaceutically acceptable carrier.

18. The method of claim 16, wherein the schwanoma related disease-state is nerve sheath tumor, schwannoma, vestibular schwannoma, sporadic schwannoma, neurofibrosarcoma, neurofibroma, neurofibromatosis (NF), neurofibromatosis type 1 (NF1), neurofibromatosis type 2 (NF2), or schwannomatosis, or a combination thereof.

19. The method of claim 16, wherein administering is intranervously, intracranially, intratumorally, intramuscularly, intravenously, intradermally, or subcutaneously, or a combination thereof.

20. A kit comprising a composition comprising an rAAV vector of serotype AAV1 comprising a caspase-1 gene and a Schwann cell specific promoter contained within packaging materials.

* * * * *

SEQUENCE LISTING

<160> NUMBER OF SEQ ID NOS: 17

<210> SEQ ID NO 1
<211> LENGTH: 1330
<212> TYPE: DNA
<213> ORGANISM: Artificial Sequence
<220> FEATURE:
<223> OTHER INFORMATION: Description of Artificial Sequence: Human Caspase-1 cDNA

<400> SEQUENCE: 1
atactttcag tttcagtcac acaagaaggg aggagagaaa agccatggcc gacaaggtcc     60

```
tgaaggagaa gagaaagctg tttatccgtt ccatgggtga aggtacaata aatggcttac    120
tggatgaatt attacagaca agggtgctga acaaggaaga gatggagaaa gtaaaacgtg    180
aaaatgctac agttatggat aagacccgag ctttgattga ctccgttatt ccgaaagggg    240
cacaggcatg ccaaatttgc atcacataca tttgtgaaga agacagttac ctggcaggga    300
cgctgggact ctcagcagct cctcaggcag tgcaggacaa cccagctatg cccacatcct    360
caggctcaga agggaatgtc aagctttgct ccctagaaga agctcaaagg atatggaaac    420
aaaagtcggc agagatttat ccaataatgg acaagtcaag ccgcacacgt cttgctctca    480
ttatctgcaa tgaagaattt gacagtattc ctagaagaac tggagctgag gttgacatca    540
caggcatgac aatgctgcta caaaatctgg ggtacagcgt agatgtgaaa aaaaatctca    600
ctgcttcgga catgactaca gagctggagg catttgcaca ccgcccagag cacaagacct    660
ctgacagcac gttcctggtg ttcatgtctc atggtattcg ggaaggcatt tgtgggaaga    720
aacactctga gcaagtccca gatatactac aactcaatgc aatctttaac atgttgaata    780
ccaagaactg cccaagtttg aaggacaaac cgaaggtgat catcatccag gcctgccgtg    840
gtgacagccc tggtgtggtg tggtttaaag attcagtagg agtttctgga aacctatctt    900
taccaactac agaagagttt gaggatgatg ctattaagaa agcccacata gagaaggatt    960
ttatcgcttt ctgctcttcc acaccagata atgtttcttg gagacatccc acaatgggct   1020
ctgtttttat tggaagactc attgaacata tgcaagaata tgcctgttcc tgtgatgtgg   1080
aggaaatttt ccgcaaggtt cgattttcat ttgagcagcc agatggtaga gcgcagatgc   1140
ccaccactga aagagtgact ttgacaagat gtttctacct cttcccagga cattaaaata   1200
aggaaactgt atgaatgtct gtgggcagga agtgaagaga tccttctgta aaggtttttg   1260
gaattatgtc tgctgaataa taaacttttt tgaaataata aatctggtag aaaaatgaaa   1320
aaaaaaaaaa                                                          1330
```

<210> SEQ ID NO 2
<211> LENGTH: 1533
<212> TYPE: DNA
<213> ORGANISM: Artificial Sequence
<220> FEATURE:
<223> OTHER INFORMATION: Description of Artificial Sequence: Mouse Caspase-1 cDNA

<400> SEQUENCE: 2

```
cttccaagtg ttgaagaaga atcatttccg cggttgaatc cttttcagac ttgagcattt     60
aaacctaact ttaattaggg aaagaaacat gcgcacacag caattgtggt tatttctcaa    120
tctgtattca cgccctgttg gaaaggaact aacaatatgc tttcagtttc agtagctctg    180
cggtgtagaa aagaaacgcc atggctgaca agatcctgag ggcaaagagg aagcaattta    240
tcaactcagt gagtataggg acaataaatg gattgttgga tgaacttttta gagaagagag    300 tgctgaatca ggaagaaatg gataaaataa aacttgcaaa cattactgct atggacaagg    360
cacgggacct atgtgatcat gtctctaaaa aagggcccca ggcaagccaa atctttatca    420
cttacatttg taatgaagac tgctacctgg caggaattct ggagcttcaa tcagctccat    480
cagctgaaac atttgttgct acagaagatt ctaaggagg acatccttca tcctcagaaa    540
caaaggaaga acagaacaaa gaagatggca catttccagg actgactggg accctcaagt    600
tttgcccttt agaaaaagcc cagaagttat ggaaagaaaa tccttcagag atttatccaa    660
taatgaatac aaccactcgt acacgtcttg ccctcattat ctgcaacaca gagtttcaac    720
```

```
atctttctcc gagggttgga gctcaagttg acctcagaga aatgaagttg ctgctggagg    780
atctggggta taccgtgaaa gtgaaagaaa atctcacagc tctggagatg gtgaaagagg    840
tgaaagaatt tgctgcctgc ccagagcaca agacttctga cagtactttc cttgtattca    900
tgtctcatgg tatccaggag ggaatatgtg ggaccacata ctctaatgaa gtttcagata    960
ttttaaaggt tgacacaatc tttcagatga tgaacacttt gaagtgccca agcttgaaag   1020
acaagcccaa ggtgatcatt attcaggcat gccgtggaga gaaacaagga gtggtgttgt   1080
taaaagattc agtaagagac tctgaagagg atttcttaac ggatgcaatt tttgaagatg   1140
atggcattaa gaaggcccat atagagaaag attttattgc tttctgctct tcaacaccag   1200
ataatgtgtc ttggagacat cctgtcaggg gctcactttt cattgagtca ctcatcaaac   1260
acatgaaaga atatgcctgg tcttgtgact tggaggacat tttcagaaag gttcgatttt   1320
catttgaaca accagaattt aggctacaga tgcccactgc tgatagggtg accctgacaa   1380
aacgtttcta cctcttcccg ggacattaaa cgaagaatcc agttcattct tatgtaccta   1440
tgctgagaat cgtgccaata agaagccaat acttccttag atgatgcaat aaatattaaa   1500
ataaaacaaa acaaaaaaaa aaaaaaaaaa aaa                                1533
```

<210> SEQ ID NO 3
<211> LENGTH: 1325
<212> TYPE: DNA
<213> ORGANISM: Artificial Sequence
<220> FEATURE:
<223> OTHER INFORMATION: Description of Artificial Sequence: Rat
      Caspase-1 cDNA

<400> SEQUENCE: 3

```
atggccgaca aggtcctgag ggcaaagagg aagcaattta tcaactcagt gagtgtaggg     60
acaataaatg gattgctgga tgaacttttta gagaagagag tcctgaacca ggaagagatg    120
gatacaatca aacttgcaaa tatcactgtt atggaaaagg cacgagacct gtgcgatcat    180
gtcactaaaa aaggaccccg ggcaagccag atgtttatca cttacatttg taatgaagac    240
tgctacctgg cagaaattct ggagcttcag tcaggtccat cagctgaaac tgttttttgtt    300
acagaagatt ctaagggagg acatcctttc tcctcagaaa caaagaaaa actgaacaaa     360
gaaggtggcg catttcctgg accgagtggt tccctcaagt tttgccctt agaaatagcc     420
cagaagttat ggaaagaaaa tcattcagag atttatccaa taatgaaaac acccactcgt    480
acacgtcttg ccctcattat ctgcagcaca gactttcaac atctttctcg gagagtcgga    540
gctgatgttg acctcagaga aatgaagttg ctgctgcagg atctggggta tactgtgaaa    600
gtcaaagaaa atctcacagc tctggagatg acaaaagaat tgaaagaatt tgctgcctgc    660
ccagagcaca agacttctga cagtaccttc cttgtattca tgtctcatgg tctccaggag    720
ggaatatgtg ggatcacata ctctaatgaa gttgcagata ttttaaaggt tgacacaatc    780
tttcaaatga tgaacacatt gaagtgccca agcttgaaag acaagcccaa ggttatcatt    840
attcaggcat gccgtggaga gaaacaagga gtggtgttgt taaaagattc agtaggaaac    900
tccgaagagg gattcttaac agatgcaatt tttgaagatg atggcattaa gaaggcccat    960
atagagaaag attttattgc tttctgctct tcaacaccag ataatgtgtc ctggagacat   1020
cctgtccggg gatccctctt cattgagtca ctcatcaaac acatgaaaga atatgcctgg   1080
tcttgtgact tggaggacat tttcagaaag gttcgatttt ctttcgaaca accagactct   1140
agactacaga tgccaaccac tgaaagggtg accctgacaa aacgtttcta cctcttccca   1200
```

```
ggacattaaa gaatccaaga cttcattctt atgtacctgt gttgggaatc atgccaataa    1260
gaagccaata atccccaaaa tgatacaata aatttcaaaa caaaacaaaa aaaaaaaaaa    1320
aaaaa                                                                1325
```

<210> SEQ ID NO 4
<211> LENGTH: 1978
<212> TYPE: DNA
<213> ORGANISM: Artificial Sequence
<220> FEATURE:
<223> OTHER INFORMATION: Description of Artificial Sequence: P0-humanICE

<400> SEQUENCE: 4

```
acgagcattc tcgaactctc caaatagcca ccaagcagga caataggcag tcttgatcat      60
ttaaactgct gcatggcaaa aggaatcgaa ggatttctta acagaagtgg ggggggggga     120
gatctgggct tcttcctgga agtttcctga tagagaaaat cttctgcctg ggtagaatct     180
cccaggatgc agggagatgg aaaaagttgt tccccagagg actttgtagt ctacagtgtt     240
gtcgtagcca tcggaacaac gagacaccct taatttggga gtgctctgaa agaaacttgc     300
ctctaggccc tagggctctc aggcaaggag gctaagaagg aatcctttgc tgtagccttt     360
tggatttagg tttctcagct tatctatccc tcagagaagt gtgtctatgt cccttttctg     420
tccctctgcc tcaccccacc caacattcc aacctaggt aggggaggt cagtatacac        480 aaagccctct gtgtaagggg tggtatgtgt ccccccaccc cctacccag agtatacaat     540 gccccttcct gctccatgcc cctgccaccc tccccaccaa cctctcaatt gcacatgcca     600
ggctgcaatt ggtccactgg ctcaggacag cccctcatg ctggggatcc aggggatttt      660
taagcaggtt ccagaaaaca ccactcagtt ccttgtcccc ccgctctctc caccccacag    720
acgctctgcc aagcttgata tcgaattctg cagaactagt gccaccatgg ccgacaaggt    780
cctgaaggag aagagaaagc tgtttatccg ttccatgggt gaaggtacaa taaatggctt    840
actggatgaa ttattacaga caagggtgct gaacaaggaa gagatggaga agtaaaacg     900 tgaaaatgct acagttatgg ataagacccg agctttgatt gactccgtta ttccgaaagg    960
ggcacaggca tgccaaattt gcatcacata catttgtgaa aagacagtt acctggcagg    1020 gacgctggga ctctcagcag atcaaacatc tggaaattac cttaatatgc aagactctca   1080
aggagtactt tcttccttc cagctcctca ggcagtgcag acaacccag ctatgcccac    1140 atcctcaggc tcagaaggga atgtcaagct ttgctcccta agaagctc aaaggatatg     1200 gaaacaaaag tcggcagaga tttatccaat aatggacaag tcaagccgca cacgtcttgc   1260
tctcattatc tgcaatgaag aatttgacag tattcctaga agaactggag ctgaggttga   1320
catcacaggc atgacaatgc tgctacaaaa tctggggtac agcgtagatg tgaaaaaaa    1380 tctcactgct tcggacatga ctacagagct ggaggcattt gcacaccgcc cagagcacaa   1440
gacctctgac agcacgttcc tggtgttcat gtctcatggt attcgggaag catttgtgg    1500 gaagaaacac tctgagcaag tcccagatat actacaactc aatgcaatct ttaacatgtt   1560
gaataccaag aactgcccaa gtttgaagga caaaccgaag gtgatcatca tccaggcctg   1620
ccgtggtgac agccctggtg tggtgtggtt taaagattca gtaggagttt ctggaaacct   1680
atctttacca actacagaag agtttgagga tgatgctatt aagaaagccc acatagagaa   1740
ggattttatc gctttctgct cttccacacc agataatgtt tcttggagac atcccacaat   1800
gggctctgtt tttattggaa gactcattga acatatgcaa gaatatgcct gttcctgtga   1860
```

```
tgtggaggaa attttccgca aggttcgatt ttcatttgag cagccagatg gtagagcgca    1920
gatgcccacc actgaaagag tgactttgac aagatgtttc tacctcttcc caggacat     1978

<210> SEQ ID NO 5
<211> LENGTH: 1963
<212> TYPE: DNA
<213> ORGANISM: Artificial Sequence
<220> FEATURE:
<223> OTHER INFORMATION: Description of Artificial Sequence:
      P0-mouseICE

<400> SEQUENCE: 5
acgagcattc tcgaactctc caaatagcca ccaagcagga caataggcag tcttgatcat      60
ttaaactgct gcatggcaaa aggaatcgaa ggatttctta acagaagtgg ggggggggga    120
gatctgggct tcttcctgga agtttcctga tagagaaaat cttctgcctg ggtagaatct    180
cccaggatgc agggagatgg aaaaagttgt tccccagagg actttgtagt ctacagtgtt    240
gtcgtagcca tcgaacaac gagacaccct taatttggga gtgctctgaa agaaacttgc    300
ctctaggccc tagggctctc aggcaaggag gctaagaagg aatcctttgc tgtagccttt    360
tggatttagg tttctcagct tatctatccc tcagagaagt gtgtctatgt ccctttcctg    420
tccctctgcc tcaccccacc ccaacattcc aacctagggt aggggaggt cagtatacac    480 aaagccctct gtgtaagggg tggtatgtgt cccccacccc cctacccag agtatacaat    540 gccccttct gctccatgcc cctgccaccc tccccaccaa cctctcaatt gcacatgcca    600
ggctgcaatt ggtccactgg ctcaggacag cccctcatg ctggggatcc aggggatttt    660
taagcaggtt ccagaaaaca ccactcagtt ccttgtcccc ccgctctctc caccccacag    720
acgctctgcc aagcttgata tcgaattctg cagaactagt gccaccatgg ctgtgagggc    780
aaagaggaag caatttatca actcagtgag tatagggaca ataaatggat tgttggatga    840
acttttagag aagagagtgc tgaatcagga agaaatggat aaaataaaac ttgcaaacat    900
tactgctatg gacaaggcac gggacctatg tgatcatgtc tctaaaaaag gccccaggc    960 aagccaaatc tttatcactt acatttgtaa tgaagactgc tacctggcag gaattctgga   1020
gcttcaatca gctccatcag ctgaaacatt tgttgctaca gaagattcta aggaggaca    1080 tccttcatcc tcagaaacaa aggaagaaca gaacaaagaa gatggcacat tccaggact    1140 gactgggacc ctcaagttt gccctttaga aaaagcccag aagttatgga agaaaatcc    1200 ttcagagatt tatccaataa tgaatacaac cactcgtaca cgtcttgccc tcattatctg    1260
caacacagag tttcaacatc tttctccgag ggttggagct caagttgacc tcagagaaat    1320
gaagttgctg ctggaggatc tggggtatac cgtgaaagtg aaagaaaatc tcacagctct    1380
ggagatggtg aaagaggtga aagaatttgc tgcctgccca gagcacaaga cttctgacag    1440
tactttcctt gtattcatgt ctcatggtat ccaggaggga atatgtggga ccacatactc    1500
taatgaagtt tcagatattt taaaggttga cacaatcttt cagatgatga acactttgaa    1560
gtgcccaagc ttgaaagaca agcccaaggt gatcattatt caggcatgcc gtggagagaa    1620
acaaggagtg gtgttgttaa aagattcagt aagagactct gaagaggatt tcttaacgga    1680 tgcaatttt gaagatgatg gcattaagaa ggcccatata gagaaagatt ttattgcttt    1740
ctgctcttca acaccagata atgtgtcttg gagacatcct gtcagggct cacttttcat    1800 tgagtcactc atcaaacaca tgaaagaata tgcctggtct tgtgacttgg aggacatttt    1860
cagaaaggtt cgatttttcat ttgaacaacc agaatttagg ctacagatgc ccactgctga   1920
```

```
tagggtgacc ctgacaaaac gtttctacct cttcccggga cat            1963
```

<210> SEQ ID NO 6
<211> LENGTH: 5379
<212> TYPE: DNA
<213> ORGANISM: Artificial Sequence
<220> FEATURE:
<223> OTHER INFORMATION: Description of Artificial Sequence: AAV-P0-
      human(h)ICE plasmid

<400> SEQUENCE: 6

```
ttggccactc cctctctgcg cgctcgctcg ctcactgagg ccgggcgacc aaaggtcgcc     60
cgacgcccgg gctttgcccg gcggcctca gtgagcgagc gagcgcgcag agagggagtg    120
ggggagatct ggtaccacga gcattctcga actctccaaa tagccaccaa gcaggacaat   180
aggcagtctt gatcatttaa actgctgcat ggcaaaagga atcgaaggat ttcttaacag   240
aagtgggggg gggggagatc tgggcttctt cctggaagtt tcctgataga gaaaatcttc   300
tgcctgggta gaatctccca ggatgcaggg agatggaaaa agttgttccc cagaggactt   360
tgtagtctac agtgttgtcg tagccatcgg aacaacgaga caccttaat ttgggagtgc    420
tctgaaagaa acttgcctct aggccctagg gctctcaggc aaggaggcta agaaggaatc   480
ctttgctgta gccttttgga tttaggtttc tcagcttatc tatccctcag agaagtgtgt   540
ctatgtccct tttctgtccc tctgcctcac cccaccccaa cattccaacc tagggtaggg   600
ggaggtcagt atacacaaag ccctctgtgt aaggggtggt atgtgtcccc ccacccccct   660
acccagagta tacaatgccc ctttctgctc catgcccctg ccaccctccc caccaacctc    720
tcaattgcac atgccaggct gcaattggtc cactggctca ggacagcccc ctcatgctgg   780
ggatccaggg gatttttaag caggttccag aaaacaccac tcagttcctt gtccccccgc   840
tctctccacc ccacagacgc tctgccaagc ttgatatcga attctgcaga actagtgcca   900
ccatggccga caaggtcctg aaggagaaga gaaagctgtt tatccgttcc atgggtgaag   960
gtacaataaa tggcttactg gatgaattat tacagacaag ggtgctgaac aaggaagaga  1020
tggagaaagt aaaacgtgaa aatgctacag ttatggataa gacccgagct ttgattgact  1080
ccgttattcc gaaaggggca caggcatgcc aaatttgcat cacatacatt tgtgaagaag  1140
acagttacct ggcagggacg ctgggactct cagcagatca aacatctgga aattaccta   1200
atatgcaaga ctctcaagga gtactttctt cctttccagc tcctcaggca gtgcaggaca  1260
acccagctat gcccacatcc tcaggctcag aagggaatgt caagctttgc tccctagaag  1320
aagctcaaag gatatggaaa caaaagtcgg cagagattta tccaataatg gacaagtcaa  1380
gccgcacacg tcttgctctc attatctgca atgaagaatt tgacagtatt cctagaagaa  1440
ctggagctga ggttgacatc acaggcatga acatgctgct acaaaatctg ggtacagcg   1500
tagatgtgaa aaaaaatctc actgcttcgg acatgactac agagctggag gcatttgcac  1560
accgccagag gcacaagacc tctgacagca cgttcctggt gttcatgtct catggtattc  1620
gggaaggcat ttgtgggaag aaacactctg agcaagtccc agatatacta caactcaatg  1680
caatctttaa catgttgaat accaagaact gcccaagttt gaaggacaaa ccgaaggtga  1740
tcatcatcca ggcctgccgt ggtgacagcc tggtgtggt gtggtttaaa gattcagtag  1800
gagtttctgg aaacctatct ttaccaacta cagaagagtt tgaggatgat gctattaaga  1860
aagcccacat agagaaggat tttatcgctt tctgctcttc cacaccagat aatgtttctt  1920
ggagacatcc cacaatgggc tctgttttta ttggaagact cattgaacat atgcaagaat  1980
```

```
atgcctgttc ctgtgatgtg gaggaaattt tccgcaaggt tcgattttca tttgagcagc    2040
cagatggtag agcgcagatg cccaccactg aaagagtgac tttgacaaga tgtttctacc    2100
tcttcccagg acattaagcg gccgctctag atgatcagcc tcgactgtgc cttctagttg    2160
ccagccatct gttgtttgcc cctcccccgt gccttccttg acctggaag gtgccactcc     2220 cactgtcctt tcctaataaa atgaggaaat tgcatcgcat tgtctgagta ggtgtcattc    2280
tattctgggg gtggggtgg ggcaggacag caagggggag gattgggaag acaatagcag     2340
gcatgcgggg agagatctag gaacccctag tgatggagtt ggccactccc tctctgcgcg    2400
ctcgctcgct cactgaggcc gcccgggcaa agcccgggcg tcgggcgacc tttggtcgcc    2460
cggcctcagt gagcgagcga gcgcgcagag agggagtggc catgcagcca gctggcgtaa    2520
tagcgaagag gcccgcaccg atcgcccttc ccaacagttg cgtagcctga atggcgaatg    2580
gcgcgacgcg cctgtagcg gcgcattaag cgcggcgggt gtggtggtta cgcgcagcgt    2640
gaccgctaca cttgccagcg ccctagcgcc cgctccttc gctttcttcc cttcctttct     2700
cgccacgttc gccggctttc cccgtcaagc tctaaatcgg gggctccctt tagggttccg    2760
atttagtgct ttacggcacc tcgacccca aaaacttgat tagggtgatg gttcacgtag     2820
tgggccatcg ccctgataga cggttttttcg ccctttgacg ttggagtcca cgttctttaa   2880
tagtggactc ttgttccaaa ctggaacaac actcaaccct atctcggtct attcttttga    2940
tttataaggg attttgccga tttcggccta ttggttaaaa aatgagctga tttaacaaaa    3000
atttaacgcg aattttaaca aaatattaac gtttacaatt tcctgatgcg gtattttctc    3060
cttacgcatc tgtgcggtat ttcacaccgc atatggtgca ctctcagtac aatctgctct    3120
gatgccgcat agttaagcca gccccgacac ccgccaacac ccgctgacgc gccctgacgg    3180
gcttgtctgc tcccggcatc cgcttacaga caagctgtga ccgtctccgg gagctgcatg    3240
tgtcagaggt tttcaccgtc atcaccgaaa cgcgcgagac gaaagggcct cgtgatacgc    3300
ctatttttat aggttaatgt catgataata atggtttctt agacgtcagg tggcactttt    3360
cggggaaatg tgcgcggaac ccctatttgt ttatttttct aaatacattc aaatatgtat    3420
ccgctcatga caataaacc ctgataaatg cttcaataat attgaaaaag gaagagtatg     3480
agtattcaac atttccgtgt cgcccttatt ccctttttg cggcattttg ccttcctgtt     3540
tttgctcacc cagaaacgct ggtgaaagta aaagatgctg aagatcagtt gggtgcacga    3600
gtgggttaca tcgaactgga tctcaacagc ggtaagatcc ttgagagttt tcgccccgaa    3660
gaacgttttc caatgatgag cacttttaaa gttctgctat gtggcgcggt attatcccgt    3720
attgacgccg ggcaagagca actcggtcgc cgcatacact attctcagaa tgacttggtt    3780
gagtactcac cagtcacaga aaagcatctt acgatggca tgacagtaag agaattatgc     3840
agtgctgcca taaccatgag tgataacact gcggccaact tacttctgac aacgatcgga    3900
ggaccgaagg agctaaccgc ttttttgcac aacatggggg atcatgtaac tcgccttgat    3960
cgttgggaac cggagctgaa tgaagccata ccaaacgacg agcgtgacac cacgatgcct    4020
gtagcaatgg caacaacgtt gcgcaaacta ttaactggcg aactacttac tctagcttcc    4080
cggcaacaat taatagactg gatggaggcg gataaagttg caggacccct ctgcgctcgg    4140
cccttccggc tggctggttt attgctgata aatctggagc cggtgagcgt gggtctcgcg    4200
gtatcattgc agcactgggg ccagatggta agccctcccg tatcgtagtt atctacacga    4260
cggggagtca gcaactatg gatgaacgaa atagacagat cgctgagata ggtgcctcac     4320
tgattaagca ttggtaactg tcagaccaag tttactcata tatactttag attgatttaa    4380
```

```
aacttcattt ttaatttaaa aggatctagg tgaagatcct ttttgataat ctcatgacca    4440 aaatcccttta acgtgagttt tcgttccact gagcgtcaga ccccgtagaa agatcaaag    4500 gatcttcttg agatccttt tttctgcgcg taatctgctg cttgcaaaca aaaaaaccac    4560
cgctaccagc ggtggtttgt ttgccggatc aagagctacc aactcttttt ccgaaggtaa    4620
ctggcttcag cagagcgcag ataccaaata ctgtccttct agtgtagccg tagttaggcc    4680
accacttcaa gaactctgta gcaccgccta catacctcgc tctgctaatc ctgttaccag    4740
tggctgctgc cagtggcgat aagtcgtgtc ttaccgggtt ggactcaaga cgatagttac    4800
cggataaggc gcagcggtcg ggctgaacgg ggggttcgtg cacacagccc agcttggagc    4860
gaacgaccta caccgaactg agatacctac agcgtgagca ttgagaaagc gccacgcttc    4920
ccgaagggag aaaggcggac aggtatccgg taagcggcag ggtcggaaca ggagagcgca    4980
cgagggagct tccaggggga aacgcctggt atctttatag tcctgtcggg tttcgccacc    5040
tctgacttga gcgtcgattt ttgtgatgct cgtcaggggg gcggagccta tggaaaaacg    5100
ccagcaacgc ggccttttta cggttcctgg ccttttgctg gccttttgct cacatgttct    5160
ttcctgcgtt atcccctgat tctgtggata accgtattac cgccttttgag tgagctgata    5220 ccgctcgccg cagccgaacg accgagcgca gcgagtcagt gagcgaggaa gcggaagagc    5280
gcccaatacg caaaccgcct ctccccgcgc gttggccgat tcattaatgc agctgggctg    5340 caggggggggg ggggggggggg tggggggggg ggggggggg                        5379

<210> SEQ ID NO 7
<211> LENGTH: 5366
<212> TYPE: DNA
<213> ORGANISM: Artificial Sequence
<220> FEATURE:
<223> OTHER INFORMATION: Description of Artificial Sequence: AAV-P0-
      mouse(m)ICE plasmid

<400> SEQUENCE: 7
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
ggggagatct ggtaccacga gcattctcga actctccaaa tagccaccaa gcaggacaat     180
aggcagtctt gatcatttaa actgctgcat ggcaaaagga atcgaaggat ttcttaacag     240
aagtgggggg gggggagatc tgggcttctt cctggaagtt tcctgataga gaaaatcttc     300
tgcctgggta gaatctccca ggatgcaggg agatggaaaa agttgttccc cagaggactt     360
tgtagtctac agtgttgtcg tagccatcgg aacaacgaga caccttaat ttgggagtgc     420 tctgaaagaa acttgcctct aggccctagg gctctcaggc aaggaggcta agaaggaatc     480
ctttgctgta gccttttgga tttaggtttc tcagcttatc tatccctcag agaagtgtgt     540
ctatgtccct tttctgtccc tctgcctcac cccacccca cattccaacc tagggtaggg     600
ggaggtcagt atacacaaag ccctctgtgt aaggggtggt atgtgtcccc ccaccccct     660 acccagagta tacaatgccc ctttctgctc catgcccctg ccaccctccc caccaacctc     720
tcaattgcac atgccaggct gcaattggtc cactggctca ggacagcccc ctcatgctgg     780
ggatccaggg gattttttaag caggttccag aaaacaccac tcagttcctt gtcccccgc     840 tctctccacc ccacagacgc tctgccaagc ttgatatcga attctgcaga actagtgcca     900
ccatggctgt gagggcaaag aggaagcaat ttatcaactc agtgagtata gggacaataa     960
atggattgtt ggatgaactt ttagagaaga gagtgctgaa tcaggaagaa atggataaaa    1020
```

```
taaaacttgc aaacattact gctatggaca aggcacggga cctatgtgat catgtctcta   1080
aaaaagggcc ccaggcaagc caaatcttta tcacttacat ttgtaatgaa gactgctacc   1140
tggcaggaat tctggagctt caatcagctc catcagctga acatttgtt gctacagaag    1200
attctaaagg aggacatcct tcatcctcag aaacaaagga agaacagaac aaagaagatg   1260
gcacatttcc aggactgact gggaccctca agttttgccc tttagaaaaa gcccagaagt   1320
tatgaaaga aaatccttca gagatttatc caataatgaa tacaaccact cgtacacgtc    1380
ttgccctcat tatctgcaac acagagtttc aacatctttc tccgagggtt ggagctcaag   1440
ttgacctcag agaaatgaag ttgctgctgg aggatctggg gtataccgtg aaagtgaaag   1500
aaaatctcac agctctggag atggtgaaag aggtgaaaga atttgctgcc tgcccagagc   1560
acaagacttc tgacagtact ttccttgtat tcatgtctca tggtatccag gagggaatat   1620
gtgggaccac atactctaat gaagtttcag atattttaaa ggttgacaca atctttcaga   1680
tgatgaaacac tttgaagtgc ccaagcttga aagacaagcc caaggtgatc attattcagg   1740
catgccgtgg agagaaacaa ggagtggtgt tgttaaaaga ttcagtaaga gactctgaag   1800
aggatttctt aacggatgca attttttgaag atgatggcat taagaaggcc catatagaga   1860
aagattttat tgctttctgc tcttcaacac cagataatgt gtcttggaga catcctgtca    1920
gggctcact tttcattgag tcactcatca aacacatgaa agaatatgcc tggtcttgtg     1980
acttggagga cattttcaga aaggttcgat tttcatttga caaccagaa tttaggctac    2040
agatgcccac tgctgatagg gtgaccctga caaaacgttt ctacctcttc ccgggacatt   2100
aagcggccgc tctagatgat cagcctcgac tgtgccttct agttgccagc catctgttgt   2160
ttgcccctcc cccgtgcctt ccttgaccct ggaaggtgcc actcccactg tcctttccta   2220
ataaaatgag gaaattgcat cgcattgtct gagtaggtgt cattctattc tggggggtgg   2280
ggtggggcag gacagcaagg gggaggattg gaagacaat agcaggcatg ctggggagag    2340
atctaggaac ccctagtgat ggagttggcc actccctctc tgcgcgctcg ctcgctcact   2400
gaggccgccc gggcaaagcc cgggcgtcgg gcgacctttg gtcgcccggc ctcagtgagc   2460
gagcgagcgc gcagagaggg agtggccatg cagccagctg gcgtaatagc gaagaggccc   2520
gcaccgatcg cccttcccaa cagttgcgta gcctgaatgg cgaatggcgc gacgcgccct   2580
gtagcggcgc attaagcgcg gcgggtgtgg tggttacgcg cagcgtgacc gctacacttg   2640
ccagcgccct agcgcccgct cctttcgctt tcttcccttc ctttctcgcc acgttcgccg   2700
gctttccccg tcaagctcta aatcgggggc tccctttagg gttccgattt agtgctttac   2760
ggcacctcga ccccaaaaaa cttgattagg gtgatggttc acgtagtggg ccatcgccct   2820
gatagacggt ttttcgccct ttgacgttgg agtccacgtt ctttaatagt ggactcttgt   2880
tccaaactgg aacaacactc aaccctatct cggtctattc ttttgattta agggatttt    2940
tgccgatttc ggcctattgg ttaaaaaatg agctgattta caaaaatttt aacgcgaatt   3000
ttaacaaaat attaacgttt acaatttcct gatgcggtat tttctcctta cgcatctgtg   3060
cggtatttca caccgcatat ggtgcactct cagtacaatc tgctctgatg ccgcatagtt   3120
aagccagccc cgacacccgc caacacccgc tgacgcgccc tgacgggctt gtctgctccc   3180
ggcatccgct tacagacaag ctgtgaccgt ctccgggagc tgcatgtgtc agaggttttc   3240
accgtcatca ccgaaacgcg cgagacgaaa gggcctcgtg atacgcctat ttttataggt   3300
taatgtcatg ataataatgg tttcttagac gtcaggtggc acttttcggg gaaatgtgcg   3360
```

```
cggaacccct atttgtttat ttttctaaat acattcaaat atgtatccgc tcatgagaca      3420
ataaccctga taaatgcttc aataatattg aaaaaggaag agtatgagta ttcaacattt      3480
ccgtgtcgcc cttattccct tttttgcggc attttgcctt cctgttttg ctcacccaga       3540 aacgctggtg aaagtaaaag atgctgaaga tcagttgggt gcacgagtgg gttacatcga      3600
actggatctc aacagcggta agatccttga gagttttcgc cccgaagaac gttttccaat      3660
gatgagcact tttaaagttc tgctatgtgg cgcggtatta tcccgtattg acgccgggca      3720
agagcaactc ggtcgccgca tacactattc tcagaatgac ttggttgagt actcaccagt     3780
cacagaaaag catcttacgg atggcatgac agtaagagaa ttatgcagtg ctgccataac     3840
catgagtgat aacactgcgg ccaacttact tctgacaacg atcggaggac cgaaggagct     3900
aaccgctttt ttgcacaaca tgggggatca tgtaactcgc cttgatcgtt gggaaccgga    3960
gctgaatgaa gccataccaa acgacgagcg tgacaccacg atgcctgtag caatggcaac   4020
aacgttgcgc aaactattaa ctggcgaact acttactcta gcttcccggc aacaattaat    4080
agactggatg gaggcggata aagttgcagg accacttctg cgctcggccc ttccggctgg    4140
ctggtttatt gctgataaat ctggagccgg tgagcgtggg tctcgcggta tcattgcagc    4200
actggggcca gatggtaagc cctcccgtat cgtagttatc tacacgacgg ggagtcaggc    4260
aactatggat gaacgaaata gacagatcgc tgagataggt gcctcactga ttaagcattg    4320
gtaactgtca gaccaagttt actcatatat actttagatt gatttaaaac ttcatttta     4380 atttaaaagg atctaggtga agatcctttt tgataatctc atgaccaaaa tcccttaacg   4440
tgagttttcg ttccactgag cgtcagaccc cgtagaaaag atcaaggat cttcttgaga    4500 tccttttttt ctgcgcgtaa tctgctgctt gcaaacaaaa aaaccaccgc taccagcggt    4560
ggtttgtttg ccggatcaag agctaccaac tcttttccg aagtaactg gcttcagcag     4620 agcgcagata ccaaatactg tccttctagt gtagccgtag ttaggccacc acttcaagaa    4680
ctctgtagca ccgcctacat acctcgctct gctaatcctg ttaccagtgg ctgctgccag    4740
tggcgataag tcgtgtctta ccgggttgga ctcaagacga tagttaccgg ataaggcgca    4800
gcggtcgggc tgaacggggg gttcgtgcac acagcccagc ttggagcgaa cgacctacac   4860
cgaactgaga tacctacagc gtgagcattg agaaagcgcc acgcttcccg aagggagaaa   4920
ggcggacagg tatccggtaa gcggcagggt cggaacagga gagcgcacga gggagcttcc    4980
agggggaaac gcctggtatc tttatagtcc tgtcgggttt cgccacctct gacttgagcg    5040
tcgatttttg tgatgctcgt cagggggggcg gagcctatgg aaaaacgcca gcaacgcggc   5100 cttttacgg ttcctggcct tttgctggcc ttttgctcac atgttctttc ctgcgttatc     5160
ccctgattct gtggataacc gtattaccgc ctttgagtga gctgataccg ctcgccgcag    5220
ccgaacgacc gagcgcagcg agtcagtgag cgaggaagcg gaagagcgcc caatacgcaa    5280
accgcctctc cccgcgcgtt ggccgattca ttaatgcagc tgggctgcag gggggggggg    5340 ggggggtgg ggggggggg ggggg                                               5366
```

<210> SEQ ID NO 8
<211> LENGTH: 736
<212> TYPE: DNA
<213> ORGANISM: Artificial Sequence
<220> FEATURE:
<223> OTHER INFORMATION: Description of Artificial Sequence: Rat P0 VNTI

<400> SEQUENCE: 8

```
acgagcattc tcgaactctc caaatagcca ccaagcagga caataggcag tcttgatcat       60
```

```
ttaaactgct gcatggcaaa aggaatcgaa ggatttctta acagaagtgg ggggggggga      120
gatctgggct tcttcctgga agtttcctga tagagaaaat cttctgcctg ggtagaatct      180
cccaggatgc agggagatgg aaaaagttgt tccccagagg actttgtagt ctacagtgtt      240
gtcgtagcca tcggaacaac gagacaccct taatttggga gtgctctgaa agaaacttgc      300
ctctaggccc tagggctctc aggcaaggag gctaagaagg aatccttttgc tgtagccttt     360 tggatttagg tttctcagct tatctatccc tcagagaagt gtgtctatgt cccttttctg      420
tccctctgcc tcaccccacc ccaacattcc aacctagggt aggggaggt cagtatacac        480 aaagccctct gtgtaagggg tggtatgtgt cccccccacc ccctacccag agtatacaat      540 gccccttttct gctccatgcc cctgccaccc tccccaccaa cctctcaatt gcacatgcca     600
ggctgcaatt ggtccactgg ctcaggacag ccccctcatg ctggggatcc aggggatttt      660
taagcaggtt ccagaaaaca ccactcagtt ccttgtcccc ccgctctctc caccccacag      720
acgctctgcc aagctt                                                      736
```

<210> SEQ ID NO 9
<211> LENGTH: 1980
<212> TYPE: DNA
<213> ORGANISM: Artificial Sequence
<220> FEATURE:
<223> OTHER INFORMATION: Description of Artificial Sequence: Homo
      sapiens myelin protein zero (P0) or (MPZ) cDNA

<400> SEQUENCE: 9

```
gttcagttcc tggtccccca ctttctcaac cccacagatg ctccgggccc ctgcccctgc       60
cccagctatg gctcctgggg ctccctcatc cagccccagc cctatcctgg ctgtgctgct      120
cttctcttct ttggtgctgt ccccggccca ggccatcgtg gtttacaccg acagggaggt      180
ccatggtgct gtgggctccc gggtgaccct gcactgctcc ttctggtcca gtgagtgggt      240
ctcagatgac atctccttca cctggcgcta ccagcccgaa gggggcagag atgccatttc      300
gatcttccac tatgccaagg acaaccccta cattgacgag gtggggacct tcaaagagcg      360
catccagtgg gtaggggacc ctcgctgaa ggatggctcc attgtcatac acaacctaga       420
ctacagtgac aatggcacgt tcacttgtga cgtcaaaaac cctccagaca tagtgggcaa      480
gacctctcag gtcacgctgt atgtctttga aaaagtgcca actaggtacg gggtcgttct      540
gggagctgtg atcggggggtg tcctcggggt ggtgctgttg ctgctgctgc ttttctacgt    600
ggttcggtac tgctggctac gcaggcaggc ggccctgcag aggaggctca gtgctatgga      660 gaagggaaa ttgcacaagc aggaaagga cgcgtcgaag cgcggggcgg agacgccagt        720
gctgtatgca atgctggacc acagcagaag caccaaagct gtcagtgaga agaaggccaa      780
ggggctgggg gagtctcgca aggataagaa atagcggtta gcgggccggg cggggatcg       840 ggggttaggg gtggagtccg ccaaaggccc aaaggtgatg gtcatcgaga tggagctacg      900
aaaggatgag cagagcccgg agctccggcc tgctgtcaag tccccccagca gaaccagcct    960 caaaaacgcc ctcaagaaca tgatgggcct gaactcggac aagtgatcgc cacccccca      1020 ccccaggccc tgccagagca gggggaccta ggctcctctt accccgtct aggtgctttc     1080 cctcttttgct ccccgccct gccctgccct cacctcctt tgagatgtaa gtttcattcc    1140
agaattcatt ccccaggcaa ttgtattctc ccccaccttc accctggct ttctgggagc      1200 ccaggagcta atcctacccc tcacctgccc cgggggctgt gtgtttggtg cctgtccacc     1260
tgagcactga gaagaaaggg actttgatac cctctgcctc aagtccaggc cacctggcat      1320
```

| | | | | |
|---|---|---|---|---|
| tcccatctcc | tgcatccccc | agcctgtccc | cctggctgtt | tcctctcccg | tccctccctc | 1380 |
| ccctctacca | ggtggcccag | ctccatactc | tgtcccccca | gctaataccc | agagcaccca | 1440 |
| gatcagactc | tccttcaggg | tttatttagg | ttattatttt | ttatttttta | atccattctt | 1500 |
| tgtttgttta | cctgtgctca | tcctctgccc | ttacacccat | gactgaggac | caatgacgtc | 1560 |
| atgtggcttt | tgcaattcac | gcccccctta | agtccttaat | gaagagccag | cccaagtaga | 1620 |
| ggggcccctg | atcctcacac | ttcagtatag | cattggttcc | ccctgaccac | tttggagcac | 1680 |
| tgttctggga | ctccaggtct | tgaggagaga | gacagagaga | gagaatggat | cctcataggt | 1740 |
| cagggagtgg | gggaggggggc | aaatgagcct | taagaaatgg | ttttttaaaca | accaaacaaa | 1800 |
| aagcaggaaa | aacaaatggg | aaatgggggg | gcggggggga | ggaagaggct | gcactgcagc | 1860 |
| cacaggggat | tcttaggatt | tttctacatt | ctgtatattt | cttctcaaac | ctccaaatgt | 1920 |
| ccttaaatgt | ttaataaaca | ctgacatttc | cagaaaaaaa | aaaaaaaaaa | aaaaaaaaa | 1980 |

<210> SEQ ID NO 10
<211> LENGTH: 1993
<212> TYPE: DNA
<213> ORGANISM: Artificial Sequence
<220> FEATURE:
<223> OTHER INFORMATION: Description of Artificial Sequence: Mus
      musculus myelin protein zero  (P0) or (Mpz)  cDNA

<400> SEQUENCE: 10

| | | | | | | |
|---|---|---|---|---|---|---|
| tgtgttccgg | gcttggtgga | tgtgtttctt | gatcttcaag | atggacgcga | cacaattcag | 60 |
| tgccagctac | ctcaaaacat | aagtttcatg | ttggtagcag | tggctgtgcc | tatagtccca | 120 |
| gcactgtgga | ggctgagaca | ctctgggcct | tgccctaccc | ccagctatgg | ctcccggggc | 180 |
| tccctcctcc | agccccagcc | ctatcctggc | tgccctgctc | ttctcttctt | tggtgctctc | 240 |
| tccagccctg | gccattgtgg | tttacacgga | cagggaaatc | tatggtgccg | tgggctccca | 300 |
| ggtgaccctg | cactgctcct | tctggtccag | tgaatgggtc | tcagatgaca | tctctttttac | 360 |
| ctggcgctac | cagcctgaag | ggggccgaga | tgccatttcg | atcttccact | atgccaaggg | 420 |
| acaaccttac | atcgatgagg | tggggacctt | caaagagcgc | atccagtggg | taggggaccc | 480 |
| tcgctggaag | gatggctcca | ttgtcataca | caacctagac | tacagtgaca | acggcacttt | 540 |
| cacatgtgat | gtcaaaaacc | caccggacat | agtgggcaag | acctctcagg | tcacgctcta | 600 |
| tgtctttgaa | aaagtgccca | ctaggtatgg | ggtggtgttg | ggagcagtga | tcgggggcat | 660 |
| cctcggggtg | tgctgttgc | tgctgttgct | cttctacctg | attcggtact | gctggctgcg | 720 |
| caggcaggct | gccctgcaga | aaggctcag | tgccatggag | aaggggagat | tcacaaaatc | 780 |
| ttcgaaggac | tcctcgaagc | gagggcggca | gacgccagtg | ctgtatgcca | tgctggacca | 840 |
| cagccgaagc | accaaagctg | ccagtgagaa | gaaatcaaaa | gggctggggg | agtctcgcaa | 900 |
| ggataagaaa | tagcggttag | cgggccgggc | gggggtcgg | gggtctgcga | cggagtcctc | 960 |
| caaaggctct | caggtggtgg | tcatcgagat | ggagcttcgc | aaagatgagc | agagctcgga | 1020 |
| gctccggcct | gcagtcaagt | cccccagtag | aaccagcctc | aagaacgccc | tcaagaacat | 1080 |
| gatgggcctg | gactcggaca | agtgaccgtc | acatccaggc | cctgtcagag | caggggacct | 1140 |
| aggctcctct | tttttcccggg | tctaggtgct | ttcctcttgc | cctcagccc | tgccctgccc | 1200 |
| ttacctccca | atgagatgta | aagtttcatt | ccaaccttcc | tttccaagtc | ttgtactcct | 1260 |
| ccttcgcctt | taccctcgg | cttttccagga | gcctaggac | taacccttact | cctcgcctgc | 1320 |
| cccaagggct | gtgtgtttgg | tgcctgtctc | tcagacaccg | agaagaaagg | gaccttgata | 1380 |

```
gcctctgccc aactccaggc cacttggcct tcccatctct ccccccccg ccccccccc     1440 cagctgatcc cctggctcct tcctgctctc cctttcctac cttctggtgg cccagctcca     1500
cactctgtcc tcgggctcaa atccacatcg tgcagagcag actctccatc agggtttatt     1560
taggttgctg agtattttt atttgccat ccattctttc gtttgtttac ctgagcccac       1620
ggccccatga ccgaggacca atgacgtcat gtggcttttg cagttcccca ctaagtcttt     1680
actggagagc caggcaggca agcagcgcat aatcgatgcc ctctgaccac tacgagcac      1740 agttctggga ctccgagatt tggggaagga agaaaaaaa aatggatcct cacaggtcag      1800
gggtgcagta gggggcttta agaaatgtct tcaaaataaa taatcagaac aggaaacgcc     1860
agcgagaatg ggaaggaaag gaagtggcta caccccgggg cacagtggac tgttaggact    1920
tttctacatt ctgtatattt ctcctaccat ctccaaatgt ccttaaatgt ttaataaaca     1980
ctgacatttc cag                                                        1993

<210> SEQ ID NO 11
<211> LENGTH: 1029
<212> TYPE: DNA
<213> ORGANISM: Artificial Sequence
<220> FEATURE:
<223> OTHER INFORMATION: Description of Artificial Sequence: Rattus
      norvegicus myelin protein zero (P0) or (Mpz)  cDNA

<400> SEQUENCE: 11
attcggctgg gcccttgccc ctaccccagc tatggctcct ggggctccct catccagccc      60
cagccctatc ctggctgccc tgctcttctc ttctttggtg ctgtcccaa ccctggccat       120 tgtggtttac acggacaggg aagtctatgg tgctgtgcgc tcccaggtca ccctgcactg     180
ctccttctgg tccagtgaat gggtctcaga tgacatctct tttacctggc gctaccagcc     240
tgaaggaggc cgagatgcca tttcaatctt ccactatgcc aagggtcaac cttacatcga     300
tgaggtgggg accttcaagg agcgcatcca gtgggtaggg gaccctagct ggaaggatgg    360
ctccattgtc atacacaacc tagactacag tgacaacggc actttcacat gtgatgtcaa     420
aaacccaccg gacatagtgg gcaagacgtc tcaggtcacg ctctatgtct ttgaaaaagt    480
gcccactagg tatggggtgg tgttgggagc cgtgatcggt ggcatcctcg ggtggtgct      540 gttgctgctg ttgctcttct acctgatccg gtactgctgg ctgcgcaggc aggctgccct    600
gcagaggagg ctcagtgcca tggagaaggg gaaatttcac aagtcttcta aggactcctc    660
gaagcgcggg cggcagacgc cagtgctgta tgccatgctg accacagcc gaagcaccaa     720 agctgccagt gagaagaaat ctaaagggct gggggagtct cgcaaggata agaaatagcg     780
gttagcgggc cgggcggggg gtcggggtc tgcgatggag tcttccaaag gctctcaggt    840
ggtggtcatc gagatggagc ttcgcaaaga tgagcagagc tcggagcccc ggcctgcagt    900
caaatccccc agtagaacca gcctcaagaa cgccctcaag aacatgatgg gcctggactc      960
gaacaagtga ccgtcacctc caggctctgt cagagcaggg gacctaggct cctcttttc       1020 ccagtctag                                                             1029

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence:  primer -
      P0-1
```

```
<400> SEQUENCE: 12
aaaggtacca cgagcattct cgaactctcc aaa                                33

<210> SEQ ID NO 13
<211> LENGTH: 35
<212> TYPE: DNA
<213> ORGANISM: Artificial Sequence
<220> FEATURE:
<223> OTHER INFORMATION: Description of Artificial Sequence:  primer -
      P0-2

<400> SEQUENCE: 13
aaaactagtt ctgcagaatt cgatatcaag cttgg                              35

<210> SEQ ID NO 14
<211> LENGTH: 39
<212> TYPE: DNA
<213> ORGANISM: Artificial Sequence
<220> FEATURE:
<223> OTHER INFORMATION: Description of Artificial Sequence:  primer -
      mCaspase-1.1

<400> SEQUENCE: 14
aaaactagtg ccaccatggc tgtgagggca agaggaag                           39

<210> SEQ ID NO 15
<211> LENGTH: 36
<212> TYPE: DNA
<213> ORGANISM: Artificial Sequence
<220> FEATURE:
<223> OTHER INFORMATION: Description of Artificial Sequence: primer -
      mCaspase-1.2

<400> SEQUENCE: 15
aaagcggccg cttaatgtcc cgggaagagg tagaaa                             36

<210> SEQ ID NO 16
<211> LENGTH: 1350
<212> TYPE: DNA
<213> ORGANISM: Artificial Sequence
<220> FEATURE:
<223> OTHER INFORMATION: Description of Artificial Sequence: Mus
      musculus myelin protein zero (P0) or (Mpz)

<400> SEQUENCE: 16
aagcttaact ctggttatgt agacattcca aacatctccc tttgtttgtt gagatggtct    60
ctgatagccc aggctagctt tgaactcctg accttcctgc ttcctgcttc cacctcccaa   120
gcactagaaa gagaggcata aaccacagtt gactttctag ttcttcccca caattcttca   180
ggagatgctt acagcacacg agattaactt caccctcttc agtcatctaa gaccttcaca   240
cttcctgttc agacttcttt cctagtgaac cctttcaaga gccacaccaa atcaaacatg   300
gatggcacaa acatggatgc tctaaatcta cacagagctt cacaaatgtc acacgtgcac   360
acactttcac ctcagctctt acctttgctg ttccatctag ccattgcccc tcccgttccc   420
tttttcaaaa tggctgctcc ttcaaggtct ctagacaaca ctgcttccta gacctgattc   480
ctctttcctc tgaacttcct gtattaagtg gcattccac cgttctgtgc attggcagtt    540
gatgagtttc cctctgtttc tcccctctgc ctcctccaac tagatcttga gcttgtagaa   600
agaacggaat taccattcta atatgagcat tcgcattccc caatgtttca aatagccacc   660
aggcaggcca atacgcagtc ttgatcattt aaactgctgc attgcataag gtaccctaac   720
agacgggaga aatttgggct tcttcctgga agtttcctgg tagagaaaat cttctatctg   780
```

```
ggtagaatct cccagataca gggaggtgga aaaagttgtt ccaagggct ttatagtcta        840 cagtgttgcc ttagcaatca gaacaacaga caccctaatt tgggagtgct ctgaaagaaa       900
cttgcctcta ggtcctaggg ctctcaggca aggagaccaa gaaggattcc tttgccatgg      960
ccttttggat ttaggtttct cagcttgtct attcctcaga gaagtgtgtc tatgcccctt     1020
ttctgtccct ctgcctcacc ctaccccaac attccaacct agggtagggg gaggtcagta     1080
tacacaaagc cctctgtgta aggggtggta tgtgtccccc caccctcca cccaccgtat      1140 acaatgcccc ttctgctcca tgcccctgc caccctcccc accacctctc cattgcacat     1200
gccaggctgc aattggtcac tggctcagga cagcccctc atgctgggga tccaggggat     1260
tttaagcagg ttccagaaaa cacagctcag ttccttgtcc cccgctctct ccaccccaca     1320
gacactctgg gcctttgccc taccccagct                                      1350

<210> SEQ ID NO 17
<211> LENGTH: 982
<212> TYPE: DNA
<213> ORGANISM: Artificial Sequence
<220> FEATURE:
<223> OTHER INFORMATION: Description of Artificial Sequence: Homo
      sapiens myelin protein zero (P0) or (MPZ)

<400> SEQUENCE: 17
gttcagttcc tggtccccca ctttctcaac cccacagatg ctccgggccc ctgcccctgc        60
cccagctatg gctcctgggg ctccctcatc cagccccagc cctatcctgg ctgtgctgct      120
cttctcttct ttggtgctgt ccccggccca ggccatcgtg gtttacaccg acagggaggt      180
ccatggtgct gtgggctccc gggtgaccct gcactgctcc ttctggtcca gtgagtgggt      240
ctcagatgac atctccttca cctggcgcta ccagcccgaa gggggcagag atgccatttc      300
gatcttccac tatgccaagg acaaccctag cattgacgag gtggggacct tcaaagagcg      360
catccagtgg gtagggggacc ctcgctgaa ggatggctcc attgtcatac acaacctaga      420
ctacagtgac aatggcacgt tcacttgtga cgtcaaaaac cctccagaca tagtgggcaa      480
gacctctcag gtcacgctgt atgtctttga aaaagtgcca actaggtacg gggtcgttct      540
gggagctgtg atcgggggtg tcctcgggt ggtgctgttg ctgctgctgc ttttctacgt       600
ggttcggtac tgctggctac gcaggcaggc ggccctgcag aggaggctca gtgctatgga      660 gaagggggaaa ttgcacaagc caggaaagga cgcgtcgaag cgcggcggc agacgccagt     720 gctgtatgca atgctggacc acagcagaag caccaaagct gtcagtgaga agaaggccaa      780
ggggctgggg gagtctcgca aggataagaa atagcggtta gcgggccggg cgggggatcg      840
ggggttaggg gtggagtccg ccaaaggccc aaaggtgatg gtcatcgaga tggagctacg      900
aaaggatgag cagagcccgg agctccggcc tgctgtcaag tccccagca gaaccagcct      960 caaaacgcc ctcaagaaca tg                                               982
```